United States Patent
Rajagopal et al.

(10) Patent No.: US 11,337,685 B2
(45) Date of Patent: May 24, 2022

(54) TRANSCATHETER ANCHORING ASSEMBLY FOR A MITRAL VALVE, A MITRAL VALVE, AND RELATED METHODS

(71) Applicant: Opus Medical Therapies, LLC, Atlanta, GA (US)

(72) Inventors: Vivek Rajagopal, Atlanta, GA (US); Jaime Eduardo Sarabia, Mableton, GA (US); Yenchin Liao, Cary, NC (US)

(73) Assignee: Opus Medical Therapies, LLC, Atlanta, GA (US)

( * ) Notice: Subject to any disclaimer, the term of this patent is extended or adjusted under 35 U.S.C. 154(b) by 268 days.

(21) Appl. No.: 16/658,404

(22) Filed: Oct. 21, 2019

(65) Prior Publication Data
US 2020/0078000 A1 Mar. 12, 2020

Related U.S. Application Data

(63) Continuation-in-part of application No. 16/136,506, filed on Sep. 20, 2018, now Pat. No. 11,123,187, and
(Continued)

(51) Int. Cl.
*A61B 17/04* (2006.01)
*A61F 2/24* (2006.01)
*A61B 17/00* (2006.01)

(52) U.S. Cl.
CPC ........ *A61B 17/0401* (2013.01); *A61F 2/2409* (2013.01); *A61F 2/2412* (2013.01);
(Continued)

(58) Field of Classification Search
CPC ...... A61B 17/0401; A61B 2017/00247; A61B 2017/00477; A61B 2017/0409;
(Continued)

(56) References Cited

U.S. PATENT DOCUMENTS 4,242,715 A 12/1980 Laird
4,337,496 A 6/1982 Laird
(Continued)

FOREIGN PATENT DOCUMENTS

AU 2016202264 A1 11/2016
CA 3 059 102 A1 10/2018
(Continued)

OTHER PUBLICATIONS

International Search Report and Written Opinion in corresponding International application No. PCT/US2018/025971 dated Jul. 10, 2018.
(Continued)

*Primary Examiner* — Tan-Uyen T Ho
*Assistant Examiner* — Charles M Wei
(74) *Attorney, Agent, or Firm* — FisherBroyles, LLP; Rachel H. Huffstetler

(57) ABSTRACT

A medical assembly implanting a transcatheter heart valve in the heart at a valve deployment site and related methods of implantation and delivery. An anchor is endovascularly introduced into the heart and implanted to a cardiac wall with an anchor delivery system and delivery cable. A second delivery system introduces a tether which coupled to the implanted anchor and a transcatheter heart valve. The transcatheter heart valve includes either a top or bottom brim which is positioned to conform to the atrial floor at the deployment site.

11 Claims, 31 Drawing Sheets

Related U.S. Application Data a continuation-in-part of application No. 15/974,696, filed on May 9, 2018, now Pat. No. 11,103,351, and a continuation-in-part of application No. 15/943,792, filed on Apr. 3, 2018, now Pat. No. 10,820,991, and a continuation-in-part of application No. 15/943,971, filed on Apr. 3, 2018, now Pat. No. 10,820,992.

(60) Provisional application No. 62/748,563, filed on Oct. 22, 2018, provisional application No. 62/558,315, filed on Sep. 13, 2017, provisional application No. 62/509,587, filed on May 22, 2017, provisional application No. 62/481,846, filed on Apr. 5, 2017.

(52) U.S. Cl.
CPC .. *A61F 2/2427* (2013.01); *A61B 2017/00247* (2013.01); *A61B 2017/00477* (2013.01); *A61B 2017/0409* (2013.01); *A61B 2017/0419* (2013.01); *A61B 2017/0464* (2013.01)

(58) Field of Classification Search
CPC .... A61B 2017/0412; A61B 2017/0419; A61B 2017/0464; A61F 2/24–2496
See application file for complete search history.

(56) References Cited

U.S. PATENT DOCUMENTS

| | | | |
|---|---|---|---|
| 4,746,057 A | 5/1988 | Wagner | |
| 4,830,360 A | 5/1989 | Carr, Jr. | |
| 5,079,776 A | 1/1992 | Crawford | |
| 5,312,438 A * | 5/1994 | Johnson | A61B 17/0401 606/104 |
| 5,569,306 A * | 10/1996 | Thal | A61F 2/0811 606/232 |
| 5,662,704 A * | 9/1997 | Gross | A61F 2/2412 623/2.1 |
| 5,683,451 A * | 11/1997 | Lenker | A61F 2/91 623/1.11 |
| 5,706,520 A | 1/1998 | Thornton et al. | |
| 5,849,004 A * | 12/1998 | Bramlet | A61B 17/0401 606/232 |
| 6,042,583 A * | 3/2000 | Thompson | A61B 17/06109 606/232 |
| 6,093,162 A | 7/2000 | Fairleigh et al. | |
| 7,431,725 B2 * | 10/2008 | Stack | A61B 17/0469 606/151 |
| 7,530,995 B2 | 5/2009 | Quijano et al. | |
| 7,780,725 B2 | 8/2010 | Haug et al. | |
| 8,147,542 B2 * | 4/2012 | Maisano | A61B 17/0401 623/2.11 |
| 8,236,049 B2 | 8/2012 | Rowe et al. | |
| 8,252,050 B2 * | 8/2012 | Maisano | A61B 17/0401 623/2.11 |
| 8,273,973 B2 | 9/2012 | Kimmons et al. | |
| 8,333,155 B2 | 12/2012 | Cylvick | |
| 8,382,829 B1 * | 2/2013 | Call | A61F 2/2487 623/2.37 |
| 8,403,938 B2 * | 3/2013 | Aeschlimann | A61C 1/07 606/93 |
| 8,403,983 B2 | 3/2013 | Quadri et al. | |
| 8,449,599 B2 | 5/2013 | Chau et al. | |
| 8,489,165 B2 | 7/2013 | Segman | |
| 8,545,553 B2 * | 10/2013 | Zipory | A61F 2/2457 623/2.37 |
| 8,549,175 B2 | 10/2013 | Krishna | |
| 8,690,939 B2 * | 4/2014 | Miller | A61F 2/2457 623/2.11 |
| 8,728,155 B2 | 5/2014 | Montorfano et al. | |
| 8,790,394 B2 * | 7/2014 | Miller | A61B 17/0401 623/2.1 |
| 8,888,843 B2 | 11/2014 | Khairkhahan et al. | |
| 8,900,295 B2 * | 12/2014 | Migliazza | A61B 17/0401 623/2.19 |
| 8,932,348 B2 | 1/2015 | Solem et al. | |
| 8,998,976 B2 | 4/2015 | Gregg et al. | |
| 9,005,084 B2 | 4/2015 | Silagy et al. | |
| 9,033,383 B2 | 5/2015 | Rampersad | |
| 9,034,033 B2 * | 5/2015 | McLean | A61F 2/2445 623/2.12 |
| 9,078,749 B2 | 7/2015 | Lutter et al. | |
| 9,375,312 B2 | 6/2016 | Weber | |
| 9,439,763 B2 | 9/2016 | Geist et al. | |
| 9,441,832 B2 | 9/2016 | Bushee | |
| 9,474,605 B2 | 10/2016 | Rowe et al. | |
| 9,480,559 B2 * | 11/2016 | Vidlund | A61F 2/2409 |
| 9,486,306 B2 | 11/2016 | Fegels et al. | |
| 9,578,982 B2 | 2/2017 | Rampersad | |
| 9,827,092 B2 * | 11/2017 | Vidlund | A61F 2/2439 |
| 9,849,001 B2 | 12/2017 | Thompson, Jr. et al. | |
| 9,895,221 B2 * | 2/2018 | Vidlund | A61F 2/2418 |
| 9,986,993 B2 * | 6/2018 | Vidlund | A61F 2/2412 |
| 10,039,639 B2 | 8/2018 | Marchand et al. | |
| 10,420,645 B2 * | 9/2019 | Del Nido | A61B 17/0401 |
| 2002/0013571 A1 * | 1/2002 | Goldfarb | A61B 17/0469 606/1 |
| 2004/0138707 A1 * | 7/2004 | Greenhalgh | A61B 17/0401 606/232 |
| 2004/0190383 A1 | 9/2004 | Marcucelli et al. | |
| 2005/0075727 A1 * | 4/2005 | Wheatley | A61F 2/2457 623/2.17 |
| 2005/0119734 A1 * | 6/2005 | Spence | A61B 17/0482 623/2.11 |
| 2005/0137697 A1 * | 6/2005 | Salahieh | A61F 2/2439 623/2.11 |
| 2006/0106279 A1 * | 5/2006 | Machold | A61B 17/00234 600/37 |
| 2006/0235509 A1 * | 10/2006 | Lafontaine | A61F 2/2436 623/2.11 |
| 2006/0241656 A1 | 10/2006 | Starksen et al. | |
| 2006/0241745 A1 | 10/2006 | Solem | |
| 2007/0118151 A1 * | 5/2007 | Davidson | A61B 17/0469 606/144 |
| 2007/0142838 A1 * | 6/2007 | Jordan | A61B 17/0401 606/75 |
| 2007/0277279 A1 | 12/2007 | Battat | |
| 2008/0125860 A1 | 5/2008 | Webler et al. | |
| 2008/0228165 A1 * | 9/2008 | Spence | A61F 2/2466 604/510 |
| 2009/0276040 A1 * | 11/2009 | Rowe | A61F 2/90 623/2.18 |
| 2010/0016655 A1 * | 1/2010 | Annest | A61B 17/00234 600/37 |
| 2011/0004296 A1 * | 1/2011 | Lutter | A61F 2/2445 623/1.26 |
| 2011/0011917 A1 * | 1/2011 | Loulmet | A61B 17/0401 227/181.1 |
| 2011/0112737 A1 | 5/2011 | Neelakantan et al. | |
| 2011/0312018 A1 | 12/2011 | Shusta et al. | |
| 2012/0078360 A1 | 3/2012 | Rafiee | |
| 2012/0136430 A1 | 5/2012 | Sochman et al. | |
| 2013/0023985 A1 * | 1/2013 | Khairkhahan | A61L 27/042 623/2.38 |
| 2013/0116780 A1 * | 5/2013 | Miller | A61F 2/2448 623/2.36 |
| 2013/0172978 A1 * | 7/2013 | Vidlund | A61F 2/2418 623/1.12 |
| 2013/0184811 A1 * | 7/2013 | Rowe | A61F 2/2418 623/2.11 |
| 2013/0190861 A1 | 7/2013 | Chau et al. | |
| 2013/0211508 A1 | 8/2013 | Lane et al. | |
| 2013/0304197 A1 | 11/2013 | Buchbinder et al. | |
| 2013/0331929 A1 | 12/2013 | Mitra et al. | |
| 2014/0005778 A1 | 1/2014 | Buchbinder et al. | |
| 2014/0031928 A1 * | 1/2014 | Murphy | A61F 2/2418 623/2.18 |
| 2014/0163668 A1 | 6/2014 | Rafiee | |
| 2014/0296972 A1 | 10/2014 | Tegels et al. | |
| 2014/0316516 A1 | 10/2014 | Vidlund et al. | |

(56) References Cited

U.S. PATENT DOCUMENTS

| | | | |
|---|---|---|---|
| 2014/0379076 A1 | 12/2014 | Vidlund et al. | |
| 2015/0025553 A1* | 1/2015 | Del Nido | A61F 2/2487 606/151 |
| 2015/0142103 A1* | 5/2015 | Vidlund | A61F 2/2439 623/2.17 |
| 2015/0250590 A1* | 9/2015 | Gries | A61B 17/0401 623/2.11 |
| 2015/0313620 A1* | 11/2015 | Suri | A61B 17/29 606/205 |
| 2015/0366556 A1* | 12/2015 | Khairkhahan | A61B 17/0401 606/232 |
| 2015/0366666 A1 | 12/2015 | Khairkhahan et al. | |
| 2016/0022501 A1 | 1/2016 | Schultz et al. | |
| 2016/0120646 A1 | 5/2016 | Dwork et al. | |
| 2016/0213467 A1 | 7/2016 | Backus et al. | |
| 2016/0262878 A1 | 9/2016 | Backus et al. | |
| 2016/0262881 A1* | 9/2016 | Schankereli | A61F 2/2436 |
| 2016/0310268 A1* | 10/2016 | Oba | A61F 2/2436 |
| 2016/0317305 A1 | 11/2016 | Pelled et al. | |
| 2016/0324635 A1 | 11/2016 | Vidlund et al. | |
| 2016/0367360 A1 | 12/2016 | Cartledge et al. | |
| 2017/0143478 A1 | 5/2017 | Schwartz et al. | |
| 2017/0209293 A1 | 7/2017 | Combs | |
| 2017/0227320 A1 | 8/2017 | Derousse | |
| 2017/0340443 A1* | 11/2017 | Stearns | A61B 17/0469 |
| 2018/0085215 A1 | 3/2018 | Vaturi et al. | |
| 2018/0289473 A1* | 10/2018 | Rajagopal | A61F 2/2427 |
| 2018/0289474 A1* | 10/2018 | Rajagopal | A61F 2/2418 |
| 2018/0289485 A1* | 10/2018 | Rajagopal | A61F 2/2457 |
| 2018/0318071 A1 | 11/2018 | Lozonschi et al. | |
| 2019/0015205 A1* | 1/2019 | Rajagopal | A61B 17/0401 |
| 2020/0001135 A1 | 1/2020 | Rajagopal | |

FOREIGN PATENT DOCUMENTS

| | | |
|---|---|---|
| CA | 3 059 106 A1 | 10/2018 |
| CN | 103826750 A | 5/2014 |
| CN | 106618798 A | 5/2017 |
| CN | 105658178 B | 5/2018 |
| DE | 10 2012 002 785 A1 | 8/2013 |
| EP | 1 462 880 A2 | 9/2004 |
| EP | 1 462 880 A3 | 4/2005 |
| EP | 3 311 754 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | 2014/021905 A1 | 2/2014 |
| WO | 2016/050751 A1 | 4/2016 |
| WO | 2016/179427 A1 | 11/2016 |
| WO | 2016/186909 A1 | 11/2016 |
| WO | DM/098 100 S | 6/2017 |
| WO | 2017117560 A1 | 7/2017 |
| WO | 2018/187390 A1 | 10/2018 |
| WO | 2018/187495 A1 | 10/2018 |
| WO | 2020/005527 A1 | 1/2020 |

OTHER PUBLICATIONS

International Search Report and Written Opinion in corresponding International application No. PCT/US2018/026118 dated Jun. 15, 2018.

Toyama et al. Mitral annular motion in patients after transcatheter MitraClip and mitral valve surgery; Echocardiography 2017; 34: 334-339.

Boudjemline Y, Agnoletti G, Bonnel D, et al. Steps toward the percutaneous replacement of atrioventricular valves an experimental study. Journal of the American College of Cardiology 2005; 46:360-5.

Bai Y, Chen HY, Zang GJ, et al. Percutaneous establishment of tricuspid regurgitation: an experimental model for transcatheler tricuspid valve replacement. Chinese medical journal 2010; 123:806-9.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013; 61:1929-31.

Lauten A, Doenst T, Hamadanchi A, Franz M, Figulla HR. Percutaneous bicaval valve implantation for transcatheler treatment of tricuspid regurgitation: clinical observations and 12-month follow-up. Circulation Cardiovascular Interventions 2014; 7:268-72.

Lauten A, Ferrari M, Hekmal K, et al. Heterotopic transcatheler tricuspid valve implantation: first-in-man application of a novel approach to tricuspid regurgitation. European heart journal 2011; 32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018; 11: e006061.

Lauten A, Figulla HR, Willich C, et al. Percutaneous caval stent valve implantation: investigation of an interventional approach for treatment of tricuspid regurgitation. European heart journal 2010; 31:1274-81.

Lauten A, Laube A, Schubert H, et al. Transcatheter treatment of tricuspid regurgitation by caval valve implantation—experimental evaluation of decellularized tissue valves in central venous position. Catheterization and cardiovascular interventions : official journal of the Society for Cardiac Angiography & Interventions 2014.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016; 12:Y116-8.

Barbanti M, Ye J, Pasupati S, El-Gamel A, Webb JG. The Helie transcatheter aortic dock for patients with aortic regurgitation. EuroIntervention : journal of EuroPCR in collaboration with the Working Group on Interventional Cardiology of the European Society of Cardiology 2013; 9 Suppl:S91-4.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017; 69:1795-806.

Rosser BA, Taramasso M, Maisano F. Transcatheter interventions fortricuspid regurgitation: TriCinch (4Tech). EuroIntervention : journal of EuroPCR in collaboration with the Working Group on Interventional Cardiology of the European Society of Cardiology 2016; 12:Y110-2.

Stephan van Bardeleben R, Tamm A, Emrich T, Munzel T, Schulz E. Percutaneous transvenous direct annuloplasty of a human tricuspid valve using the Valtech Cardioband. European heart journal 2017; 38:690.

Kuwata S, Taramasso M, Nietlispach F, Maisano F. Transcatheter tricuspid valve repair toward a surgical standard first-in-man report of direct annuloplasty with a cardioband device to treat severe functional tricuspid regurgitation. European heart journal 2017.

Rogers J. Transcatheter TR solution 6: Millipede. Transcatheter Cardiovascular Therapeutics; 2017 Nov. 1, 2017; Denver, Colorado.

Parada-Campelo F, Perlman G, Philippon F, et al. First-in-Man Experience of a Novel Transcatheter Repair System for Treating Severe Tricuspid Regurgitation Journal of the American College of Cardiology 2015; 66:2475-83.

Nickenig G, Kowalski M, Hausleiter J, et al. Transcatheter Treatment of Severe Tricuspid Regurgitation With the Edge-to-Edge MitraClip Technique. Circulation 2017; 135:1802-14.

Cao P. Catheter-Based Tricuspid Valve Replacement Via Right Atrium: An Animal Experimental Study. Transcatheter Cardiovascular Therapeutics; 2017; Denver, Colorado.

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017; 10.

(56) References Cited

OTHER PUBLICATIONS

Regueiro, et al. Transcatheter Mitral Valve Replacement: Insights From Early Clinical Experience and Future challenges; JACC vol. 69, No. 17, 2017; May 2, 2017: 2175-92.
Non-Final Office Action received for U.S. Appl. No. 15/943,792 dated Jan. 8, 2020, 50 pages.
International Search Report and Written Opinion of the International Searching Authority dated Aug. 30, 2019, in International Application No. PCT/US19/36428.
Non-Final Office Action received for U.S. Appl. No. 15/943,971 dated Jan. 8, 2020, 49 pages.
International Preliminary Report on Patentability received for PCT Application Serial No. PCT/US2018/025971 dated Oct. 17, 2019, 9 pages.
International Preliminary Report on Patentability received for PCT Application Serial No. PCT/US2018/026118 dated Oct. 17, 2019, 11 pages.
International Search Report and Written Opinion issued in corresponding international application No. PCT/US2019/057145 dated Dec. 31, 2019.

* cited by examiner

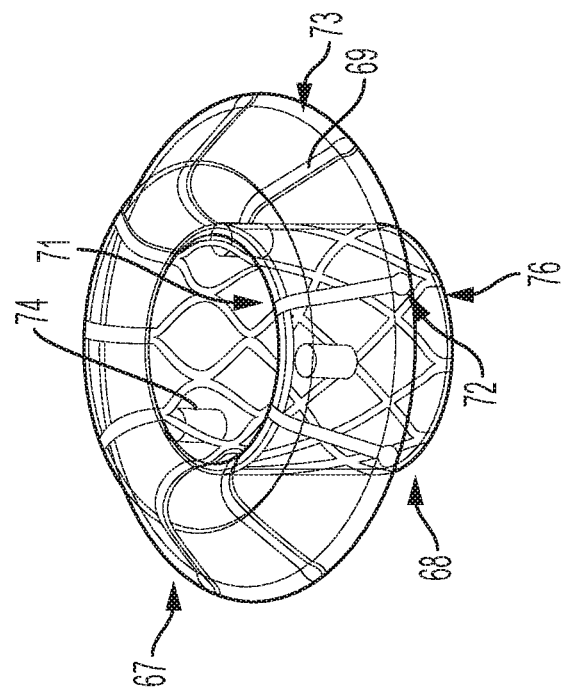
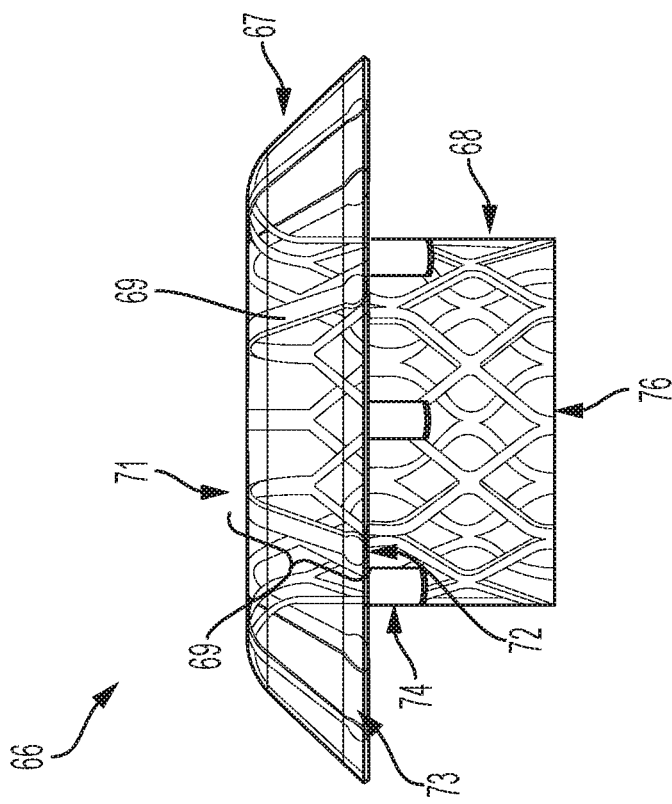
Fig. 10B
Fig. 10A

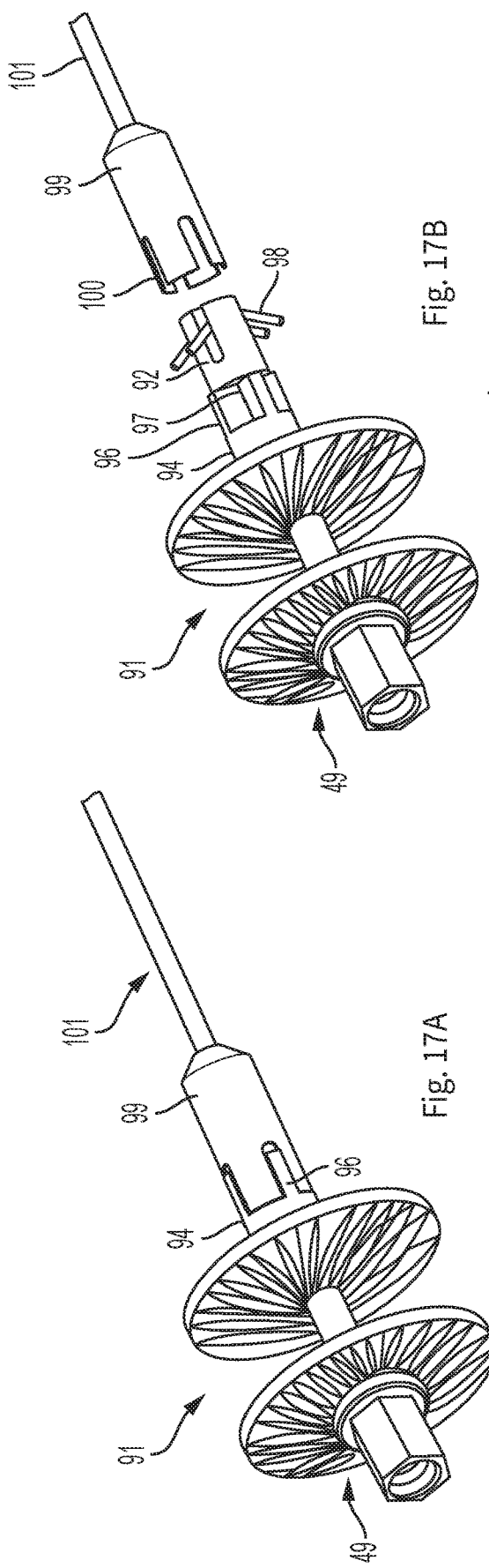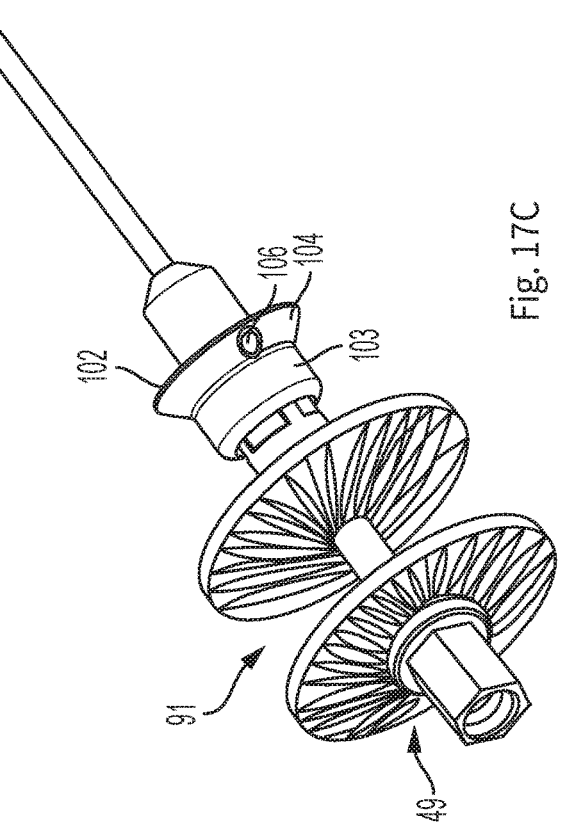

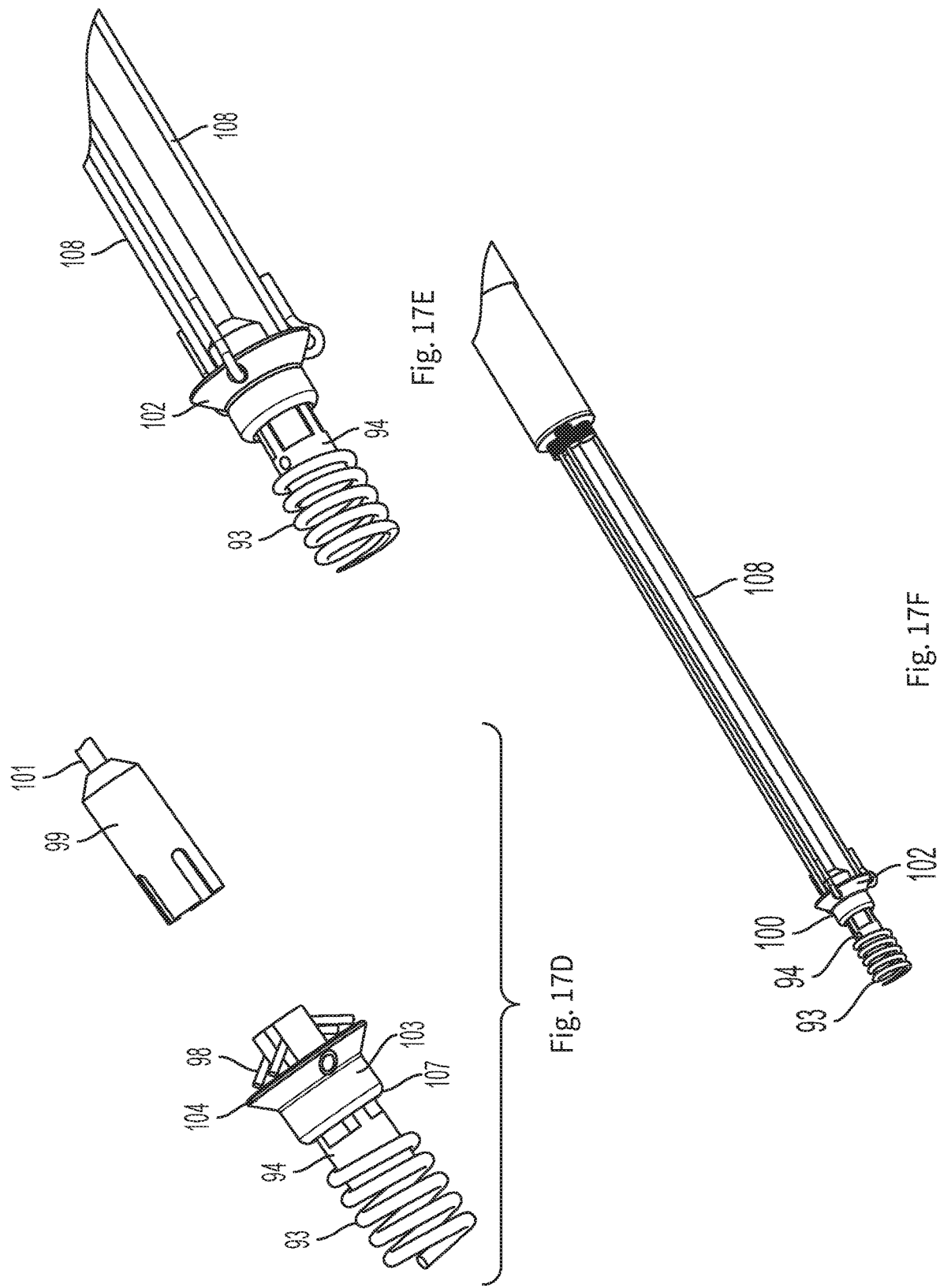

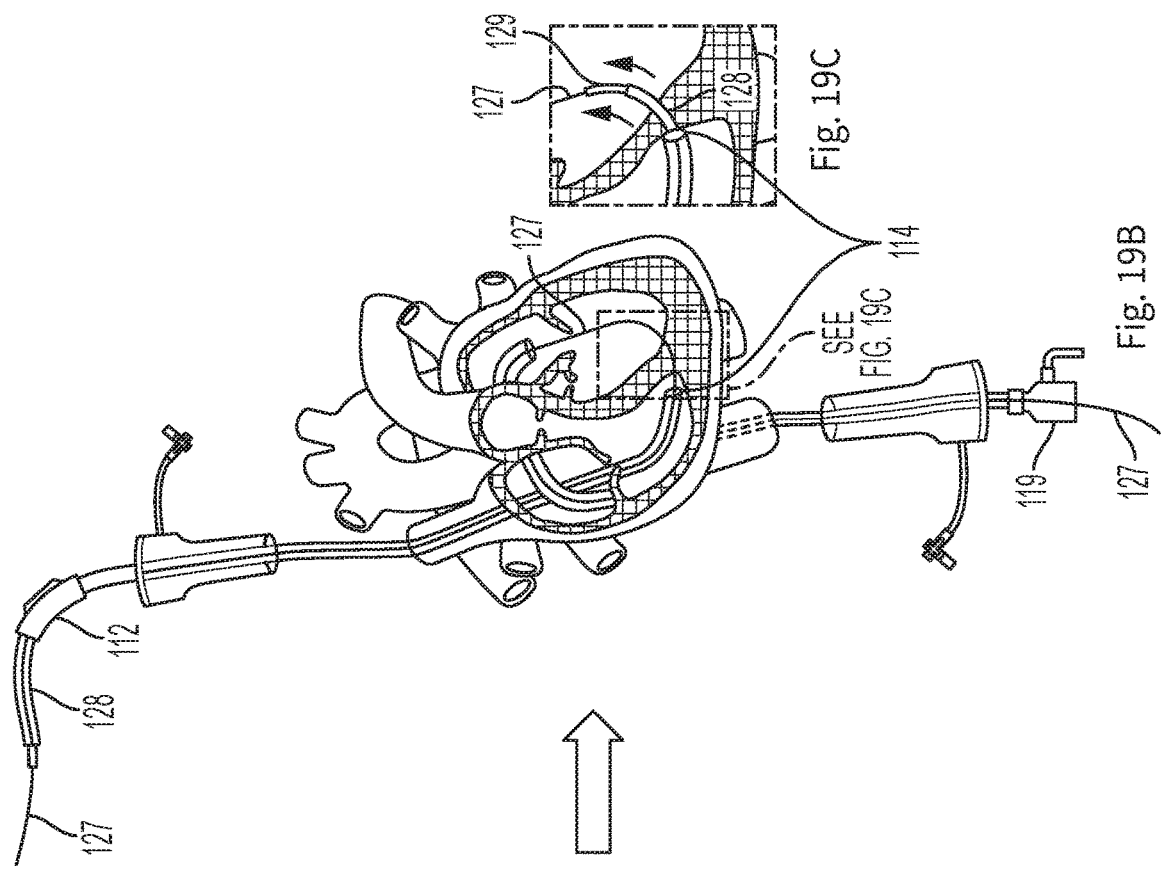
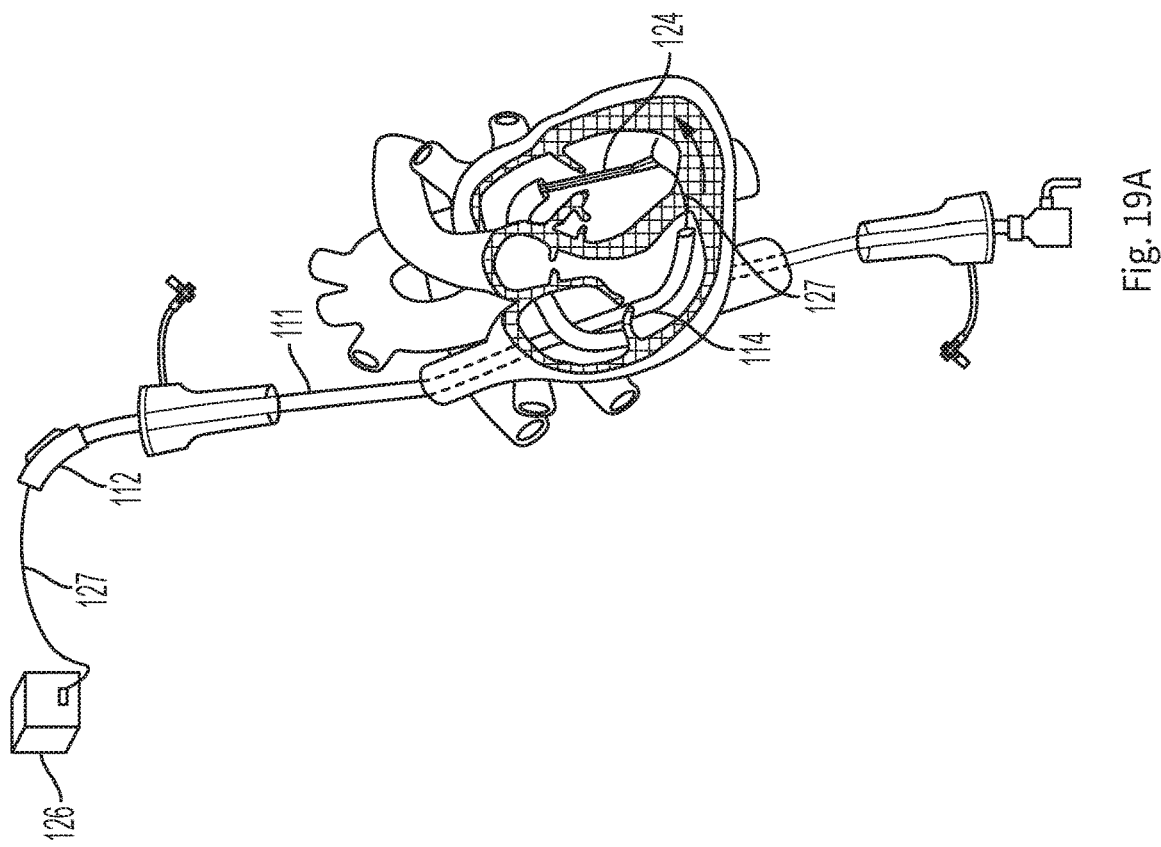

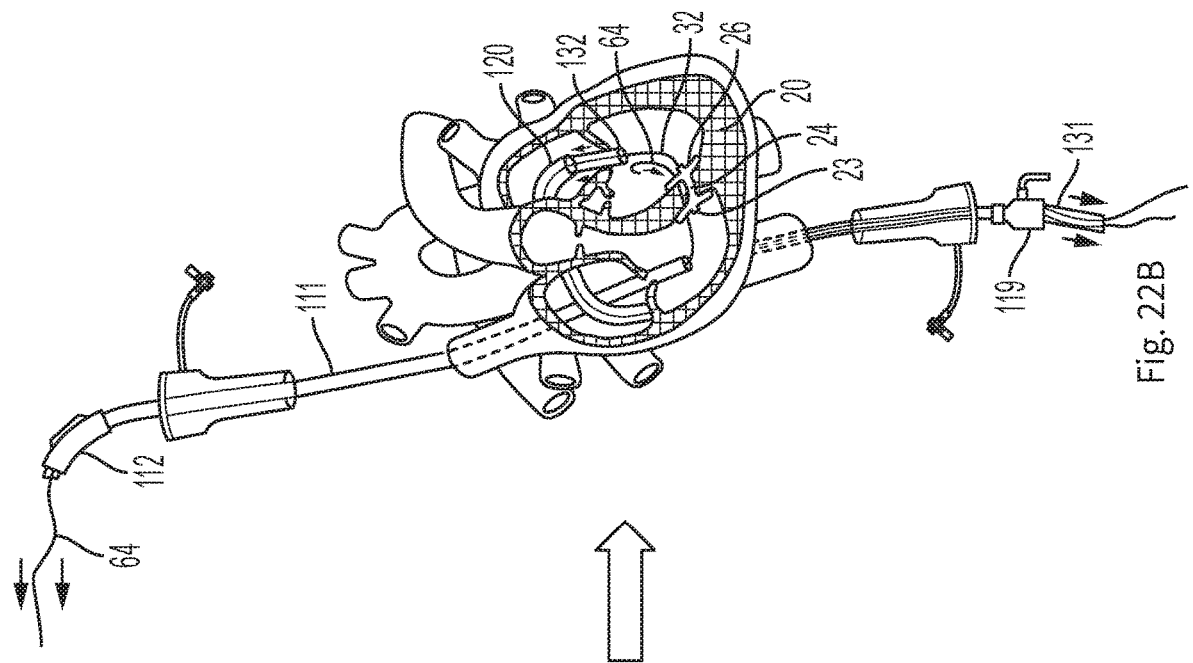
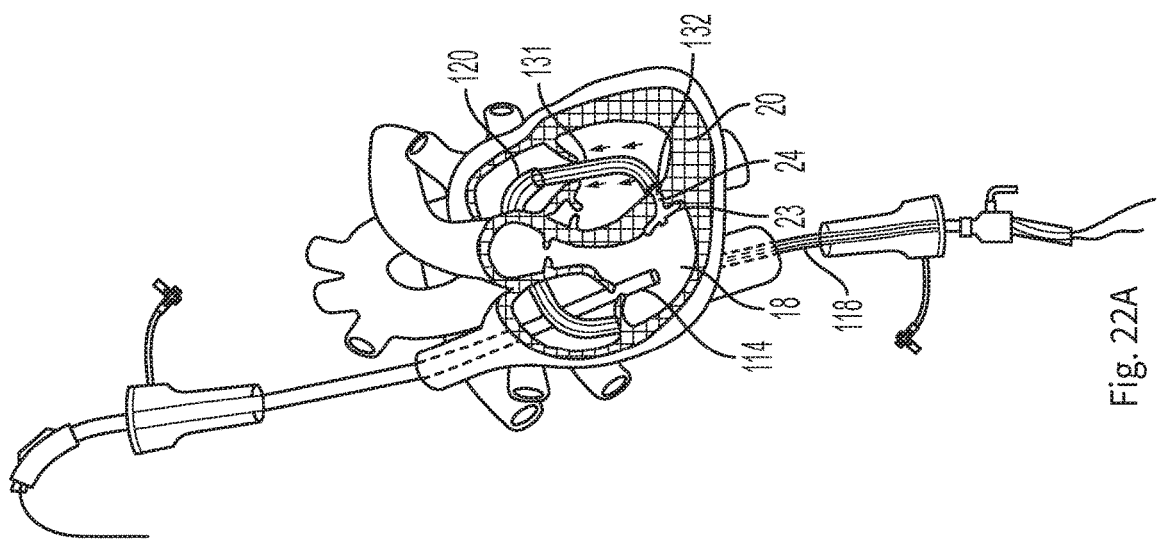
Fig. 22A
Fig. 22B

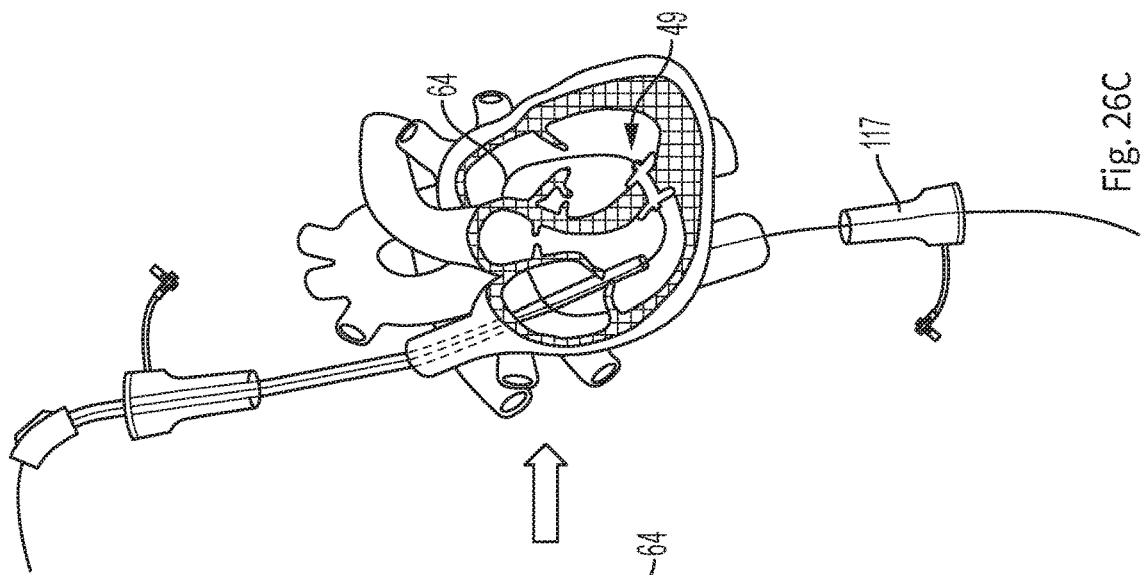
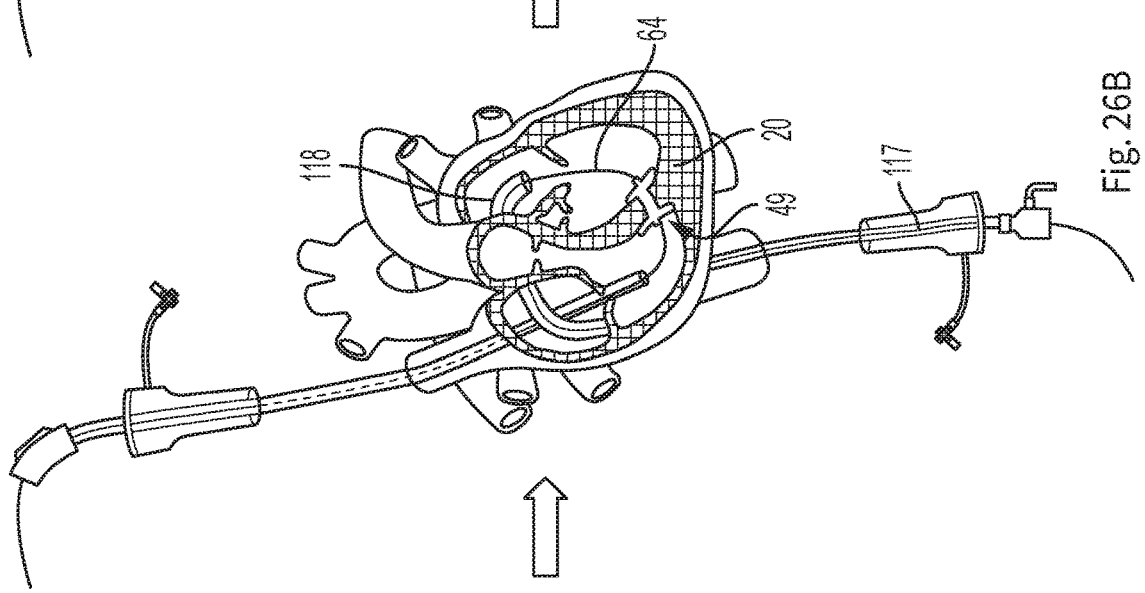
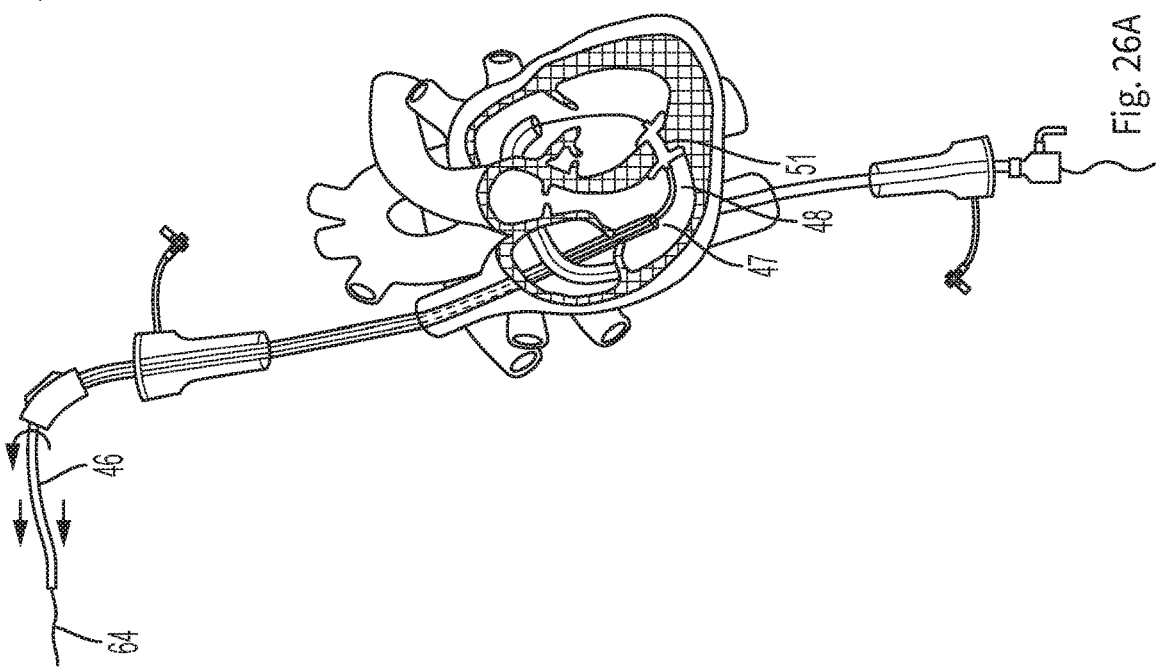

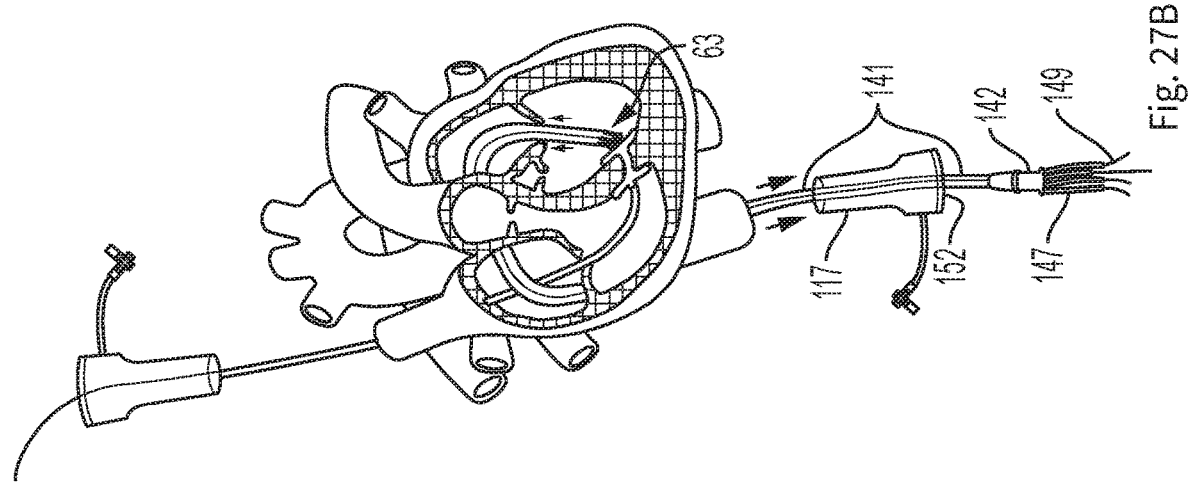
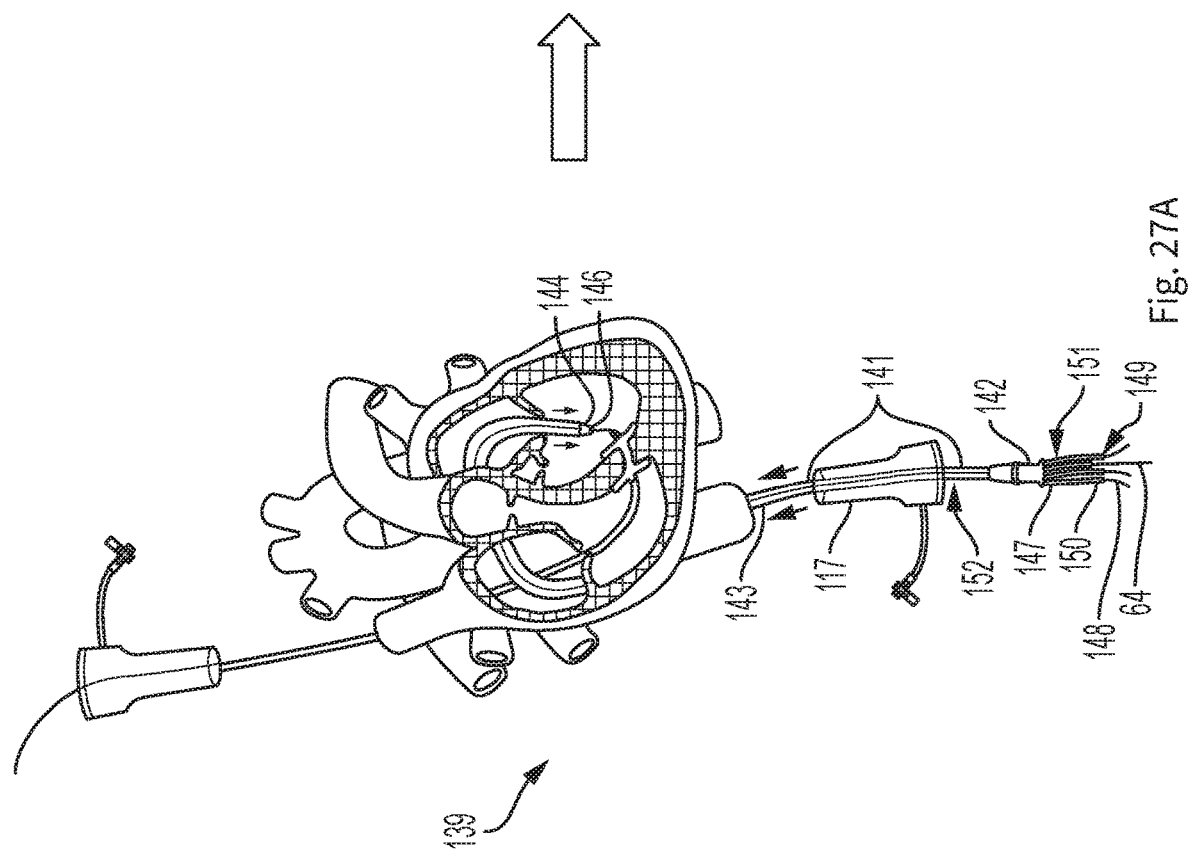

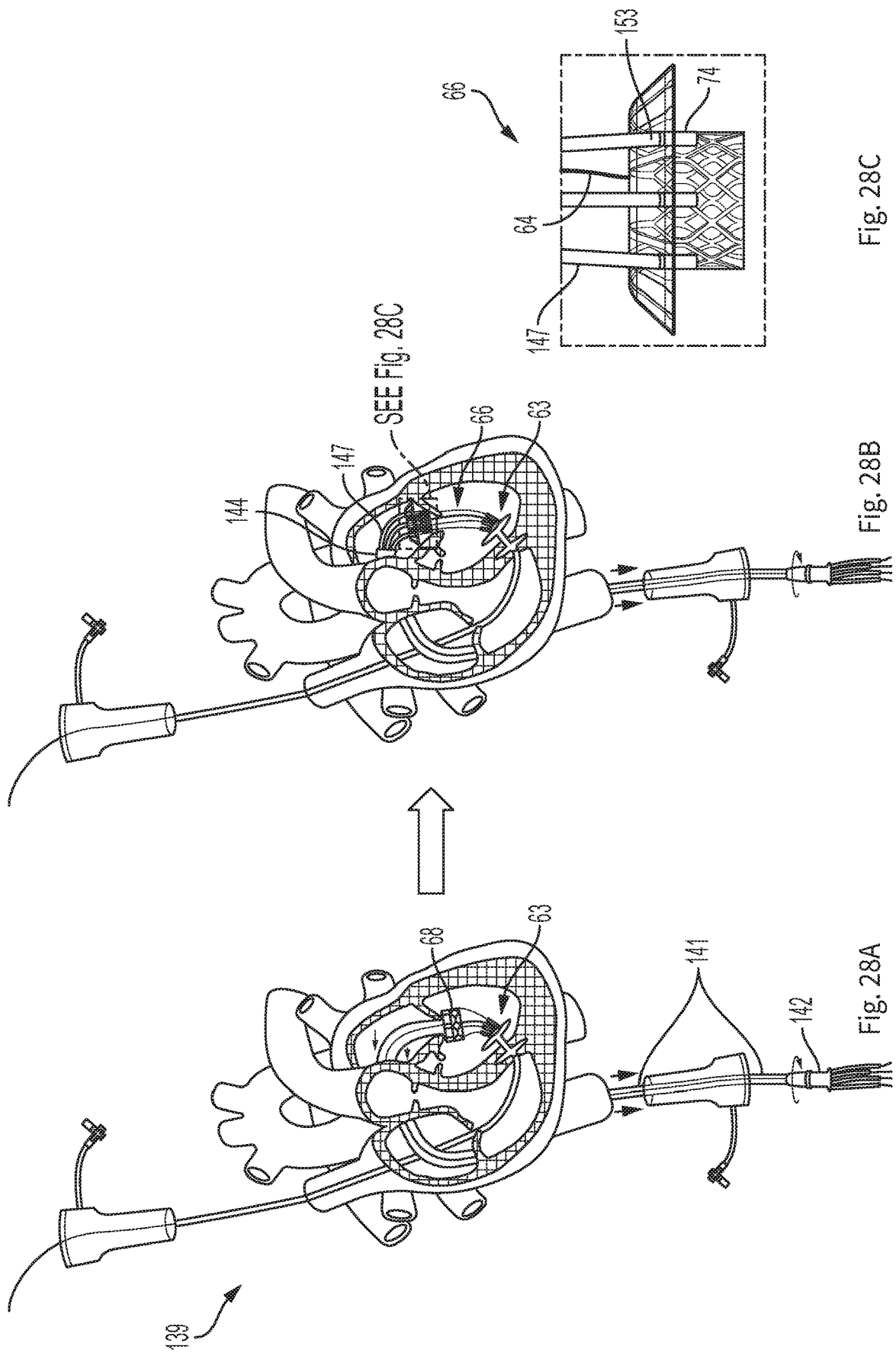

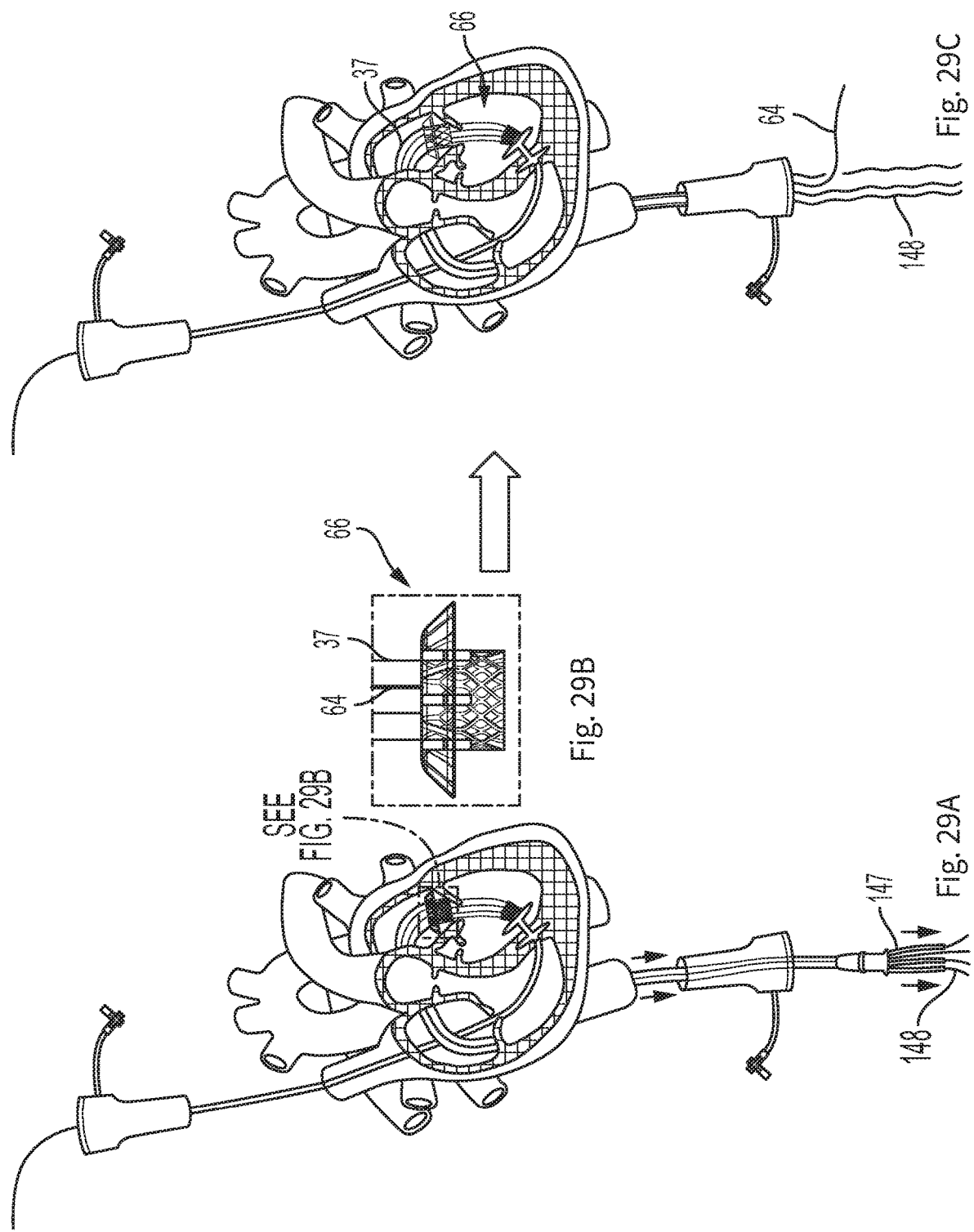

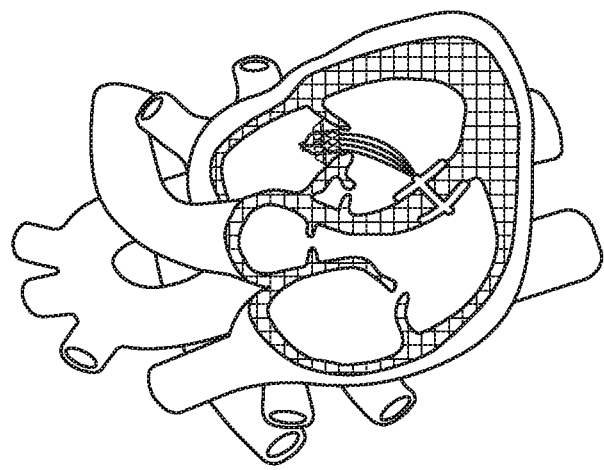
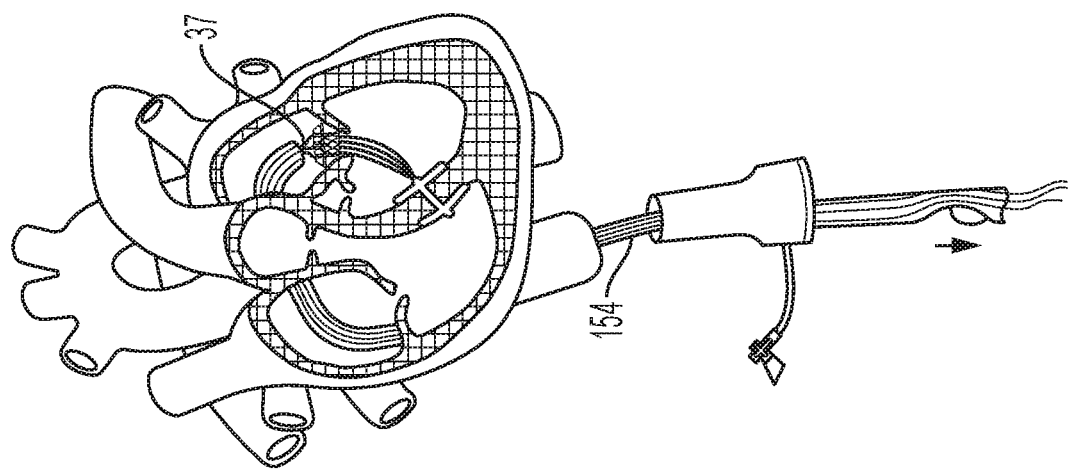
Fig. 30B
Fig. 30A

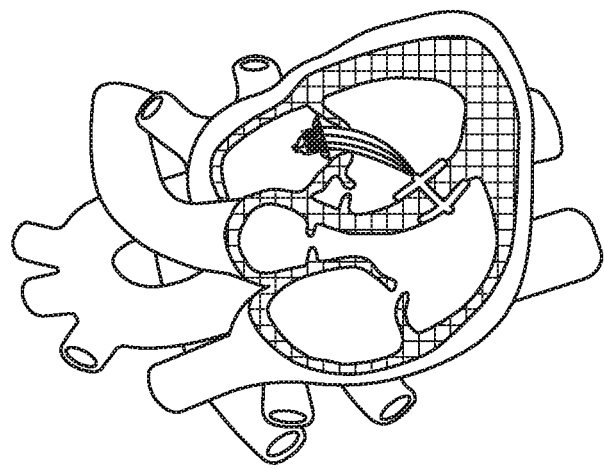
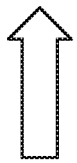
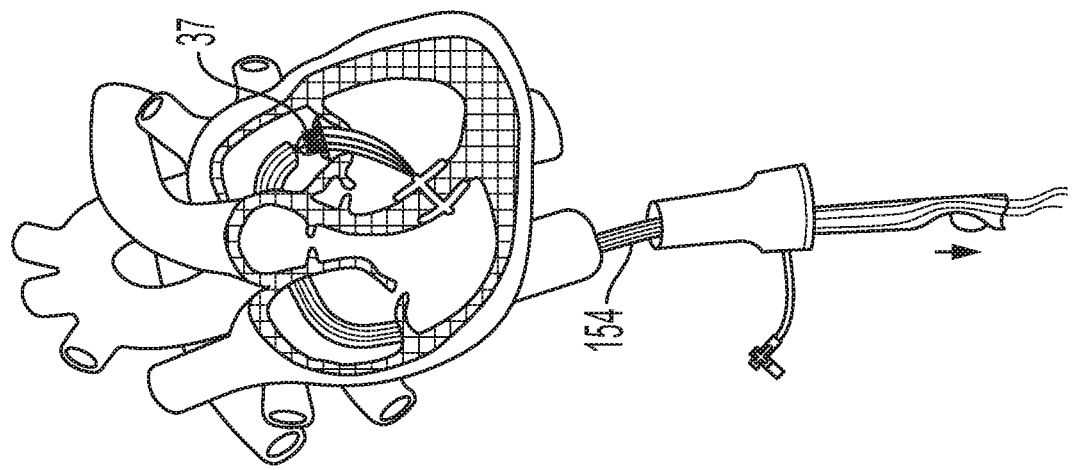
Fig. 30D
Fig. 30C

TRANSCATHETER ANCHORING ASSEMBLY FOR A MITRAL VALVE, A MITRAL VALVE, AND RELATED METHODS

CROSS-REFERENCE TO RELATED APPLICATIONS

This application claims the benefit of an priority to U.S. Provisional Patent Application Ser. No. 62/748,563 (filed Oct. 22, 2018) and is a continuation-in-part of Ser. No. 15/943,971 (filed Apr. 3, 2018), a continuation-in-part of U.S. patent application Ser. No. 15/943,792 (filed Apr. 3, 2018), a continuation-in-part of U.S. patent application Ser. No. 15/974,696 (filed May 9, 2018), and a continuation-in-part of U.S. patent application Ser. No. 16/136,506 (filed Sep. 20, 2018) all of which claim the benefit of and priority to Provisional Patent Application Ser. Nos. 62/481,846 (filed Apr. 5, 2017), 62/509,587 (filed May 22, 2017), and 62/558,315 (filed Sep. 13, 2017), the disclosures each of which are incorporated by reference herein in its entirety.

FIELD OF THE INVENTION

The present invention relates generally to a medical assembly for minimally invasively implanting a valve in the heart, a novel valve for replacing the native heart valve, and an anchor device for positioning and restraining the valve. The present invention also relates to methods of implantation of components of the medical assembly and the valve. More specifically, the invention pertains to a novel transcatheter valve, transcatheter valve skirt, anchor device, anchor delivery system, and a valve delivery device as well as methods related to such assembly for endovascularly implanting the valve across the mitral valve, for replacing the function of the native mitral valve.

BACKGROUND OF THE INVENTION

Transcatheter valves have proven safe and effective for the replacement of native cardiac valves such as aortic and pulmonic valves. Less certainty exists for the replacement of mitral valves, because initial clinical trials of transcatheter mitral valve replacement (TMVR) have faced significant challenges posed by the clinical and anatomical complexity of mitral valve disease.

Mitral valve disease, primarily causing mitral regurgitation (MR), results from either a primary degeneration of the valve (e.g. myxomatous degeneration, endocarditis, rheumatic disease, congenital disease, or other causes), or from incomplete leaflet coaptation (secondary or "functional" mitral regurgitation) that can occur from a combination of mitral annular dilation and/or mitral leaflet tethering secondary to left ventricular dilation and papillary muscle displacement. MR increases left atrial pressure, causing pulmonary congestion, thereby leading to signs and symptoms of congestive heart failure, namely peripheral edema, orthopnea, paroxysmal nocturnal dyspnea, and progressive dyspnea on exertion. Additionally, MR exacerbates left ventricular dysfunction, decreasing survival. Because many patients suffering MR have significant comorbidities and have high surgical risk, developing minimally invasive (i.e. transcatheter) methods to treat MR is important.

The initial transcatheter techniques developed have important limitations because they repair, but do not replace, the mitral valve. For example, transcatheter annuloplasty devices [Arto (MVRx, Inc., San Mateo, Calif., USA); Cardioband (Edwards Lifesciences, Irvine, Calif., USA); Carillon (Cardiac Dimensions, Kirkland, Wash., USA); Millipede (Boston Scientific, Marlborough, Mass., USA); Mitral Loop Cerclage (Tau-PNU Medical Co, Ltd. Pusan, Korean); Mitralign (Mitralign, Inc., Tewksbury, Mass., USA)] mimic surgical annuloplasty by directly or indirectly reducing the dimensions of the mitral annulus, allowing the mitral leaflets to coapt more completely. Nonetheless, these techniques are limited by uncertain reproducibility and by the inability to deal with leaflet tethering or abnormalities. Conversely, the MitraClip repair system (Abbott Vascular, Abbott Park, Ill., USA) or the Pascal system (Edwards Lifesciences) can treat leaflet abnormalities by plicating the leaflets together, replicating the surgical Alfieri stitch. Although the MitraClip system is FDA approved and effective for many patients, a significant number of patients (>10%) have recurrent MR after MitraClip and many patients cannot receive MitraClip because of anatomical restrictions. Similarly, artificial chordal therapies [NeoChord DS1000 (NeoChord, Inc., St. Louis Park, Minn., USA); Harpoon TSD-5 and V-chordal (Edwards LifeSciences)] are currently limited to very specific anatomy (e.g. isolated leaflet prolapse).

Transcatheter mitral valve replacements (TMVR) are not as limited by anatomical restrictions, and few patients have recurrent MR. Still, the current technologies have limitations and disadvantages based on the way they anchor to the mitral valve. Anchoring to the mitral valve leaflets, the Fortis valve (Edward Lifesciences) had an unacceptable rate of thrombosis. Also anchoring to the native leaflets, the Tiara valve (Neovasc, Richmond, BC, Canada) has been implanted successfully without the same thrombosis issues. Similarly, CardiAQ (Edwards Lifesciences), which engages the mitral annulus directly, NaviGate (NaviGate Cardiac Structures, Lake Forest, Calif., USA), which pierces annulus and leaflets with "winglets", Cephea (Abbott Vascular), which engages the annulus with its "hour-glass" shape, and the Intrepid valve (Medtronic, Minneapolis, Minn., USA), which engages the annulus via a "champagne cork-like" effect, have all been implanted without thrombotic issues.

Nevertheless, because these devices anchor directly to the mitral annulus, they constrain, to varying degrees, freedom of mitral annular motion. Constraining this freedom might contribute to left ventricular dysfunction. For example, a study comparing transcatheter mitral valve repair (using Abbott Vascular's MitraClip device) to open heart surgery showed that mitral annular motion was significantly lower with open heart surgery, which the authors suggested was a factor in the lower left ventricular ejection fraction (LVEF) after open heart surgery compared to transcatheter repair. Similarly, a study comparing flexible to rigid mitral annuloplasty rings found a significantly lower LVEF with rigid rings, which constrain mitral annular motion more than flexible rings. Thus, by constraining the mitral annulus, these devices could have deleterious effects on left ventricular function.

Similarly, TMVR devices that use docking systems might, by constraining mitral annular motion, decrease left ventricular function. In particular, Caisson (Livallova, PLC, London, England), HighLife (HighLife SAS, Paris, France), MValve (Boston Scientific), and Sapien M3 (Edwards Lifesciences) valves all use docking systems to anchor transcatheter prostheses to the mitral annulus.

In addition to constraining the mitral annulus, these devices also incur the risk of left ventricular outflow tract (LVOT) obstruction, which occurs when the valve props open the anterior mitral leaflet, thereby creating a fixed obstruction to flow out of the LVOT. This is a particular limitation for TMVR devices in patients with small, hypertrophied ventricles (more common in women), or in patients with significant mitral annular calcification.

Mitigating these concerns and limitations, the Tendyne valve (Abbott Vascular) has a lesser risk of LVOT obstruction and does not constrain the mitral annulus as much as other TMVR devices. Tendyne achieves this because the valve anchors via chords attached to an epicardial tether. Thus, it does not require rigid fixation to the mitral annulus, and the narrow intra-annular portion of this valve does not push the anterior mitral leaflet into the LVOT to the same degree as other valves. The problem with Tendyne is that it requires trans-apical access (incision in the left ventricle), which could be deleterious to left ventricular function in some patients.

Avoiding trans-apical access and not constraining the mitral annulus or inducing LVOT obstruction, the Alta valve (4C Medical Therapies) consists of a supra-annular valve held in position with a large, flexible ball cage in the left atrium. It is unclear, however, if this ball cage will induce atrial abnormalities, such as fibrosis, thereby causing atrial fibrillation and/or loss of atrial systolic function. Furthermore, the continued function of the native mitral leaflets might cause flow disturbances that alter prosthetic leaflet function.

Accordingly, it remains desirable in the pertinent art to provide a transcatheter valve for placement across the mitral annulus that can be delivered without trans-apical access, which has minimal risk of LVOT obstruction, allows normal atrial and mitral annular function by not anchoring to the atrium or to the mitral annulus, and is fully repositionable and retrievable during the procedure.

SUMMARY OF THE INVENTION

Presented herein is a medical assembly that is implanted minimally invasively across the mitral valve, for replacing the function of the native mitral valve. The method disclosed herein implants the mitral valve via trans-septal access, and the valve, which can be intra- or supra-annular, anchors to the interventricular septum, thus avoiding mitral annular anchoring and constraint, and at the same time minimizes risk of LVOT obstruction. Accordingly, and beneficially, no portion of the system requires surgical thoracotomy and trans-apical access for implantation.

In one aspect, the system comprises a transfemoral venous interatrial trans-septal guide and trans-septal crossing needle that allows crossing the interatrial septum for delivery of a snare sheath into the left ventricle, with delivery of the snare into the left ventricle adjacent to the inter-ventricular septum.

The system further comprises a transjugular venous interventricular trans-septal guide and radiofrequency crossing wire that allows crossing the interventricular septum, followed by snaring the wire into the snare sheath positioned in the left ventricle. With externalization of the wire out of the body via the interatrial trans-septal guide, a wire loop forms, with the wire extending from outside the transjugular guide to outside transfemoral guide. An exchange catheter is advanced over the wire loop, and the radiofrequency wire is exchanged for a larger and stiffer wire.

In one aspect, the system comprises an antegrade or retrograde anchor delivery sheath that advances over the wire loop, and an antegrade or retrograde interventricular septal anchor attached to an anchor cap configured to accept a tether. The tether is configured to attach to one or more cords, and the tether attaches to the transcatheter valve.

According to various aspects, the interventricular septal anchor may consist of a right ventricular and left ventricular disk, connected by an interventricular septal element, and each of these may be composed of any metal alloy, such as, but not limited to, nitinol, stainless steel, titanium, or cobalt-chromium. Each element of the anchor may be covered with either synthetic materials such as, but not limited to, polytetrafluoroethylene (PTFE) or polyethylene terephthalate (PET), or biological membranes, such as, but not limited to, bovine or porcine pericardial tissue.

The anchor cap is also composed of any metal alloy and is coupled to the left ventricular disk of the interventricular septal anchor. With a retrograde interventricular septal anchor (delivered from left ventricular side of the septum), the proximal end of the anchor cap defines an internal "female" thread, which accepts "male" of a distal end of a delivery cable. In one aspect, the delivery cable remains attached to the anchor cap and is used to guide the tether until the docking ring of the tether couples with the anchor. Finally, the delivery cable may be unscrewed from the anchor cap and removed.

With an antegrade interventricular septal anchor (delivered from the right ventricular side of the septum), the anchor cap is a conduit for the wire loop. The right ventricular disk has a cable connector which defines an internal "female" thread that accepts the "male" of a distal end of an antegrade delivery cable. The antegrade delivery cable also serves as a conduit for the wire loop so that the wire starts external to the transfemoral sheath, passes via the anchor cap of the interventricular septal anchor, through the delivery cable attached to the right ventricular side of the septal anchor, and exits the transjugular sheath. The wire loop extending through the anchor cap guides the tether until the docking ring of the tether couples with the anchor. After coupling, the wire loop may be removed, and the antegrade delivery cable may be unscrewed, fully deploying the interventricular septal anchor, with the tether coupled to the anchor cap.

In one aspect, the tether has a docking ring attached to at least one docking ring arm with an eyelet defined at the proximal end of the docking ring arm. Each eyelet connects to a distal end of a tether rod that attaches to the eyelet via a hook. The tether rod is composed of any metal alloy, and a proximal end of the tether rod is coupled to a cord. In one aspect, the docking ring of the tether is advanced over the anchor cap, depressing the protruding locking arms of the anchor cap. In another aspect, the docking ring reaches the end of the anchor cap, allowing the protruding locking arms to push out, thereby locking the docking ring, and therefore the tether, in place. In another aspect, even after being locked into place, the tether is free to rotate about the longitudinal axis of the anchor cap, without affecting the position of the anchor cap or the anchor screw. For retrieval, the valve delivery catheter reverts over the locking arms, thereby depressing them, and allowing the docking ring of the tether to be retracted.

In one aspect, the system comprises the tether configured to couple and/or secure the valve to the interventricular septum, and the transcatheter valve comprises a body housing valve leaflets integrated to a top or bottom brim.

In one aspect, the transcatheter valve is self-expanding and composed of nitinol and covered with either synthetic materials such as, but not limited to, polytetrafluoroethylene (PTFE) or polyethylene terephthalate (PET), or biological membranes such as, but not limited to, bovine or porcine pericardial tissue.

The leaflets of the transcatheter heart valve are composed of, but not limited to, bovine, equine, or porcine pericardial tissue, according to one aspect. In another aspect, the transcatheter heart valve is covered with a membrane having a diameter greater than the annulus at the site of deployment so that in use the membrane substantially covers the mitral annulus.

The frame of the transcatheter valve, in its intra-annular form, begins as a cylindrical shape, with the bottom of the cylinder at or below the valve annular level, and with the top of the cylinder extending into the atrium. From the top of the cylinder extends a top brim, composed of one or more wire extensions, made of laser-cut or formed nitinol. These extensions are fashioned as shapes such as, but not limited to, lines, arcs, hooks, circles, ellipses, sinusoidal curves, or of polygons of three or more sides. The extensions of the top brim, like the body of the valve, are covered and/or connected with synthetic or biological membranes. The top brim is perpendicular to the valve body or may bend toward the atrial floor as either as a convex or concave curve. To facilitate sealing as the top brim bends toward the atrial floor, the covering fabric consists of either a braided or knit fabric, which allows for "stretchability", improving the ability to conform to the topography of the atrial floor.

In the supra-annular form of the transcatheter valve, the frame begins with a bottom brim positioned at the floor of the left atrium. The bottom brim is composed of one or more wire extensions, made of laser-cut or formed nitinol. These extensions are fashioned as shapes such as, but not limited to, lines, arcs, hooks, circles, ellipses, sinusoidal curves, or of polygons of three or more sides. The extensions of the bottom brim, like the body of the valve, are covered and/or connected with synthetic or biological membranes. The bottom brim is perpendicular to the transcatheter valve body or may bend toward the atrial floor as either as a convex or concave curve. To facilitate sealing as the bottom brim bends toward the atrial floor, the covering fabric consists of either a braided or knit fabric, which allows for "stretchability", improving the ability to conform to the topography of the atrial floor. From the bottom brim, a cylinder, housing the valve leaflets, extends into the left atrium.

In one aspect, adjacent to the top of the cylinder of the valve, running longitudinally along the interior or exterior of valve body, are one or more conduits, which take the shape of a cylinder whose cross-section is any portion of a circle, ellipse, parabola, or hyperbola, or take the shape of a polyhedron with a flat base and top which assume the shape of a polygon with three or more sides. These conduits are constructed from the membrane covering the valve body, or may be made of, but not limited to, stainless steel, nitinol or other metal alloys. The one or more conduits are hollow and accommodate at least one cord attached to at least one tether, and each conduit attaches to a detachable lock near the atrial surface of the valve.

The detachable locks securely fix the transcatheter valve to the anchoring system, comprised of the tether coupled to the interventricular septal anchor, which is securely attached to the interventricular septum. In one aspect, a tether is coupled to the interventricular septal anchor via the anchor cap, and at least one cord extends from the tether through the at least one conduit of the skirt body. Thus, the transcatheter valve is threaded onto the cord via the conduit so that the transcatheter valve slidingly interacts with the cord. In another aspect, the proximal end of the cord attaches to a suture, which extends outside of the heart to be accessible by a user.

The system further comprises at least one atrial positioning rod whose proximal end is attached to the delivery system, and whose distal end is reversibly coupled to a detachable lock, which is attached to the proximal end of the conduit of the transcatheter valve body. Through the inner lumen of the positioning rod runs suture and/or cord, so that the positioning rod pushes or pulls the transcatheter valve body, thereby applying differential force and flexion to the associated top or bottom brim, allowing apposition to the atrial floor. In another aspect, rotation of the positioning rod and/or pushing or pulling of internal elements of the positioning rod causes the detachable lock to engage the cord and/or suture, securing the cord and/or suture to the transcatheter valve body, maintaining the force and flexion of the top or bottom brim to the atrial floor, and securing position of the transcatheter valve.

Related methods of implantation are also provided. Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical assembly that is implanted minimally invasively in the heart and be protected by the accompanying claims.

BRIEF DESCRIPTION OF THE DRAWINGS

FIGS. 10A and 10B are side elevational view and top perspective views of the intra-annular valve, composed of the top brim attached to transcatheter valve body with integrated valve leaflets;

FIGS. 17A-17F are perspective views of an anchor having an anchor screw and anchor cap configured for receipt of connecting ring and a tethering system illustrated in sequential steps.

FIG. 19A is a perspective view of the snare receiving the interventricular septal crossing wire;

FIG. 19B is a perspective view of the interventricular septal crossing catheter advancing across the septum;

FIG. 19C is an enlarged perspective view of the interventricular septal crossing catheter advancing across the septum;

FIG. 22A is a perspective view of the right ventricular disc of the retrograde anchor being deployed;

FIG. 22B is a perspective view of the left ventricular disc of the retrograde anchor deployed and the 0.035" rail wire being withdrawn;

FIG. 26A is a perspective view of the antegrade anchor delivery cable being unscrewed and removed;

FIG. 26B is a perspective view of the antegrade anchor delivery cable removed with the 0.035" rail wire remaining in place;

FIG. 26C is a perspective view of the trans-septal guide removed, leaving the 0.035" rail wire in place for receipt of the transcatheter valve to advance on dock onto the antegrade anchor;

FIG. 27A is a perspective view of the valve delivery system approaching the anchor;

FIG. 27B is a perspective view of the tether coupled to anchor cap of the anchor;

FIG. 28A is a perspective view of the valve delivery guide partially withdrawn, and the intra-annular portion of the valve is exposed;

FIG. 28B is a perspective view of the valve delivery guide fully withdrawn, exposing the top brim of the valve in the left atrium with the atrial positioning rods still connected to the transcatheter valve body;

FIG. 28C is an enlarged perspective view of the valve fully exposed with the atrial positioning rods still connected to the transcatheter valve body;

FIG. 29A is a perspective view of the atrial locks engaged and the atrial positioning rods withdrawn, leaving suture alone connected to the body of the transcatheter valve;

FIG. 29B is an enlarged perspective view of the atrial locks engaged and the atrial positioning rods withdrawn, leaving suture alone connected to the body of the transcatheter valve;

FIG. 29C is a perspective view of the valve deployed and the valve delivery system withdrawn from the body, leaving suture connected to the transcatheter valve body exiting the body via the valve delivery sheath;

FIG. 30A is a perspective view of the suture cutter advanced via the valve delivery sheath to just above the top brim of the transcatheter valve;

FIG. 30B is a perspective view of the valve fully deployed after suture has been cut above the top brim of the valve;

FIG. 30C is a perspective view of FIG. 30A with a mitral valve according to another aspect of the invention;

FIG. 30D is a perspective of FIG. 30B with the mitral valve shown in FIG. 30C;

DETAILED DESCRIPTION OF THE INVENTION

Figure 1:
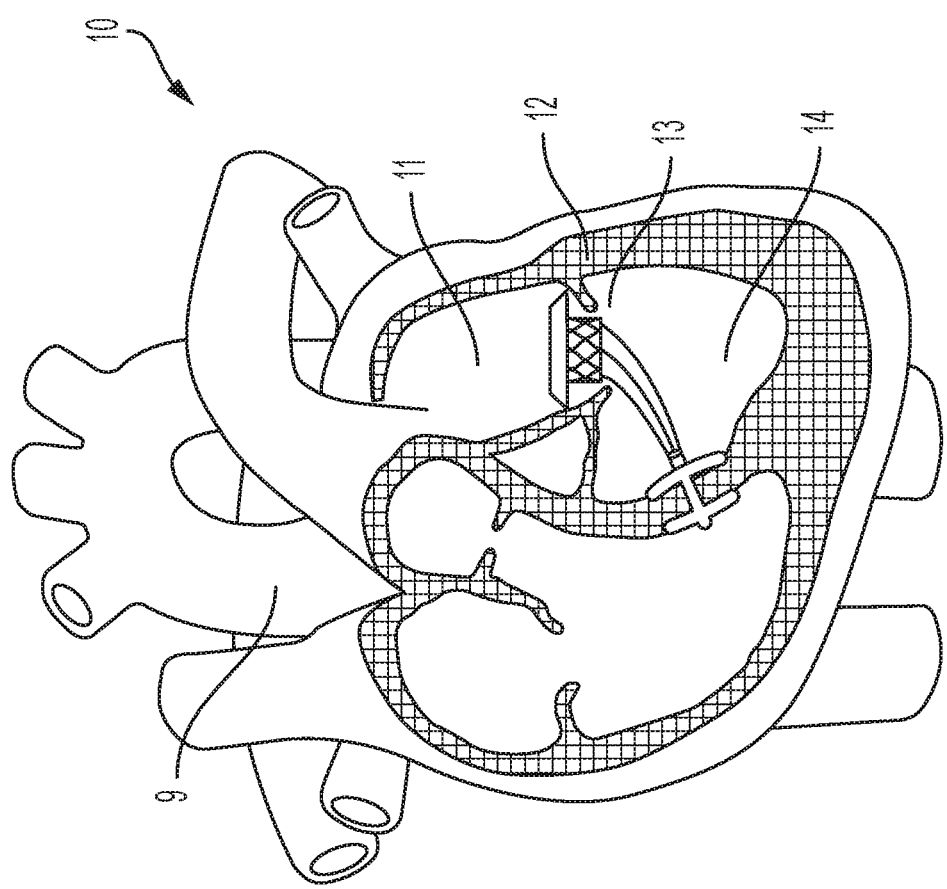
FIG. 1 is a cut-away perspective view of a heart showing the transcatheter valve system of the present application positioned in the heart, according to one aspect.

The present invention is understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes are made to the aspects described, while still obtaining the beneficial results of the present invention. It will also be apparent that some of the desired benefits of the present invention is obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges is expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. As used herein "fluid" refers to any substance that is free to flow and include liquids, gases, and plasma. "Fluid communication" as used herein refers to any connection or relative positioning permitting substances to freely flow between the relevant components. As used herein "distal" refers to the direction of application and "proximal" refers to the direction of the user of the device.

The application relates to medical devices and systems to be minimally invasively implanted in the heart and methods of implantation of these devices and systems. More specifically, the application relates to devices, methods and systems for endovascularly introducing and anchoring a retrograde or antegrade anchor 22 or 49 to the interventricular septum 20 and implanting a valve 66 (see FIGS. 10A and 10B, 11A and 11B) in the heart tethered to the retrograde or antegrade anchor 22 or 49 to replace the native mitral valve. Also, a tethering assembly cooperates with the anchor 22 or 49 connecting the valve 66 or 156 to the anchor 22 or 49. Furthermore, the valve 66 includes a top brim 67 or bottom brim 157 for connected to valve body 68 so that the valve via top brim 67 or bottom brim 157 conforms to the respective atrial floor to prevent paravalvular regurgitation of prosthesis. According to the disclosure herein, the anchor is implanted independent of the tether and the transcatheter valve.

The Retrograde Anchor Assembly

The components of retrograde anchor assembly 44 shown in FIGS. 2-5 include an anchor 22 having anchor cap 27 and a delivery cable 32 allowing delivery of a tether 36. The anchor cap 27 is coupled to the left ventricular disk 26, which is connected via the septal connector 24 to the right ventricular disk 23. The delivery cable 32 is removably connected to the anchor cap 27. The septal connector 24, as shown, is sized and configured to span the interventricular septum. Optionally, however, the septal connector 24 may be differentially sized (longer or shorter depending on the thickness of the interventricular septum) and take the shape of a cylinder whose cross-section is any portion of a circle, ellipse, parabola, or hyperbola, or take the shape of a polyhedron with a flat base and top which assume the shape of a polygon with three or more sides. The septal connector may be constructed of any known metal alloy including, but not limited to, stainless steel, nitinol, titanium, cobalt-chromium, or other metal alloys. In another aspect, the metal alloy of the septal connector 24 may be coated with biological tissue, such as bovine, ovine, porcine, or equine pericardium, or with any combination of anti-inflammatory drugs that might promote healing and limit inflammation. The right and left ventricular disks may be constructed of any known metal alloy including, but not limited to, stainless steel, nitinol, titanium, cobalt-chromium, or other metal alloys. Additionally, the right and left ventricular disks may take the shape of any portion of a circle, ellipse, parabola, or hyperbola, or take the shape of a polygon with three or more sides. The right and left ventricular disks may be covered with, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The right and left ventricular disks may also be covered with adult or juvenile bovine, ovine, equine, or porcine pericardium. In a further aspect, the anchor 22 has anchoring elements (not shown) positioned along its right and left ventricular disks. These anchoring elements allow fixation to the interventricular septum but are not necessarily used a primary fixation mechanism.

In use, the retrograde anchor 22 is secured to the interventricular septum by unsheathing the right ventricular disk 23 against the right ventricular surface 17 of the interventricular septum 20, then exposing the septal connector 24, followed by unsheathing the left ventricular disk 26 against the left ventricular surface 16 of the interventricular septum 20. By resheathing the left ventricular disk 26, then septal connector 24, and finally right ventricular disk 23, the retrograde anchor is removed safely from the cardiac wall, either to be repositioned, or to be removed entirely.

The anchor cap 27 comprises at least one locking arm 29 extending radially outwardly from the anchor cap 27. The locking arm 29 is sized and configured for releasably securing a portion of the tether 36 (described below) to the anchor cap 27. The at least one locking arm 29 moves between a first locked position, in which the locking member 29 extends a first distance away from the body of the anchor cap 27, and a second unlocked position in which the locking member 29 extends a second distance away from the anchor cap 27 that is less than the first distance. The anchor cap 27 comprises at least one biasing member (not shown), such as a spring, configured to urge each locking arm 29 to the first locked position. As shown, a plurality of locking arms 29 are provided and are spaced equally around the circumference of the anchor cap 27, though it is contemplated that the locking arms 29 need not be spaced equally.

Figure 3:
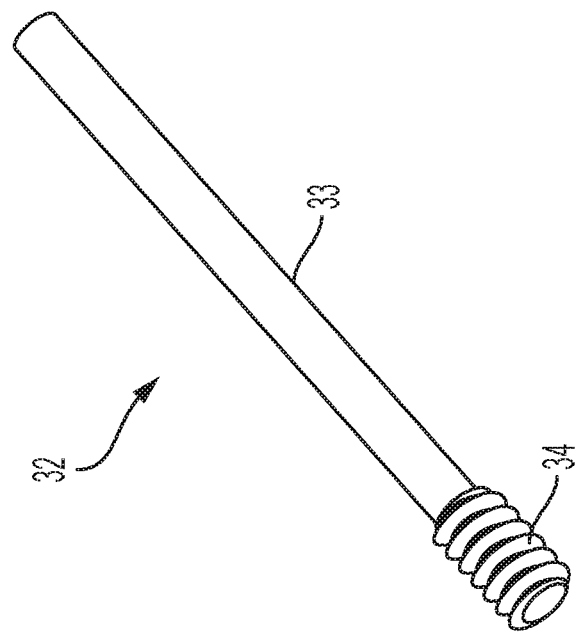
FIG. 3 is a perspective view of the delivery cable of the retrograde anchor for anchoring a tether to a cardiac wall.

Now referring to FIG. 3, the delivery cable 32 includes a flexible delivery wire 33 having a distal threaded end portion 34 positioned on or formed in the distal end of the delivery wire 33. The delivery wire is constructed of, but not limited to, stainless steel, nitinol or other metal alloys, with or without hydrophilic coatings, or with or without a polymer coating such as polytetrafluoroethylene (PTFE). The distal threaded end portion 34 is be sized and configured to selectively engage complementary threads formed in a cavity defined in a proximal end 31 of the anchor cap 27. See FIGS. 2 and 5. In use, the distal threaded end portion 34 advances, e.g., screws, into via the proximal end 31 of the anchor cap 27 to couple the anchor cap 27 to the distal end of the flexible wire 33. As described more fully below, the distal threaded end portion 34 is unscrewed from the proximal end of the anchor 22, detaching the flexible wire 33 from the anchor 22.

According to another aspect of the disclosure, as shown in FIGS. 17A-17F, an anchor assembly 91 is illustrated. The anchor 91 includes an anchor shaft 92 and an antegrade anchor 49, although a retrograde anchor 22 can be interchanged in this anchor assembly 91. As shown, the antegrade anchor 49 extends distally from an anchor base 94. The anchor base 94 defines at least one, or a plurality as shown, of anchor flanges 96 and recessed areas 97 therebetween. The anchor shaft 92 includes at least one or, as shown, a plurality of locking members 98 shown in FIG. 17B. Locking members 98 are biased, such as by a spring (not shown), radially outwardly from the anchor shaft 92. An anchor connector 99 and connector rod 101 cooperate with the anchor shaft 92 to connect to the antegrade anchor 49. The anchor connector 101 defines at least one or, as shown, a plurality of apertures 1020 configured for receipt of the anchor flanges 96. Accordingly, the anchor connector 99 and connector rod 101 are matingly connected to the anchor shaft 92, thereby urging the locking members 98 inward. The cooperating of the apertures 100 and the flanges 96 integrate the anchor connector 101 and the anchor base 94.

After the antegrade anchor 49 has been implanted, a tether ring 102 is applied over the connector rod 101 and anchor connecter 99 and abuts the proximal end of the antegrade anchor 49. The tether ring 102 includes a generally cylindrical first distal portion 103 and a second proximal portion 104 having a diameter greater than the first portion 103. The second portion 104 defines at least one or, as shown, a plurality of apertures 106 configured for receipt of tether rods 108 as shown in FIGS. 17E and 17F. As shown in FIG. 17D, the anchor connector 99 and connector rod 101 are removed. The locking members 98 are urged radially outward so as to engage the second portion 104 of the tether ring 102 to lock the tether ring 102 on the anchor base 94. Tether rods 108 are operative as described above for cooperating with transcatheter valve 66 or 156.

The Antegrade Anchor Assembly

The components of antegrade anchor assembly 63 shown in FIGS. 6-9 include an anchor 49 having anchor cap 58 and delivery cable connector 51, and a delivery cable 46 allowing delivery of a tether 36. The anchor cap 58 is coupled to the left ventricular disk 57, which is connected via the septal connector 56 to the right ventricular disk 54. The delivery cable 46 is removably connected to the delivery cable connector 51 via its threaded end 52. The septal connector 56, as shown, is sized and configured to span the interventricular septum. Optionally, however, the septal connector 56 may be differentially sized (longer or shorter depending on the thickness of the interventricular septum) and take the shape of a cylinder whose cross-section is any portion of a circle, ellipse, parabola, or hyperbola, or take the shape of a polyhedron with a flat base and top which assume the shape of a polygon with three or more sides. The septal connector may be constructed of any known metal alloy including, but not limited to, stainless steel, nitinol, titanium, cobalt-chromium, or other metal alloys. In another aspect, the metal alloy of the septal connector 56 may be coated with biological tissue, such as bovine, ovine, porcine, or equine pericardium, or with any combination of anti-inflammatory drugs that might promote healing and limit inflammation. The right and left ventricular disks may be constructed of any known metal alloy including, but not limited to, stainless steel, nitinol, titanium, cobalt-chromium, or other metal alloys. Additionally, the right and left ventricular disks may take the shape of any portion of a circle, ellipse, parabola, or hyperbola, or take the shape of a polygon with three or more sides. The right and left ventricular disks may be covered with, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The right and left ventricular disks may also be covered with adult or juvenile bovine, ovine, equine, or porcine pericardium. In a further aspect, the anchor 49 has anchoring elements (not shown) positioned along its right and left ventricular disks. These anchoring elements allow fixation to the interventricular septum but are not necessarily used a primary fixation mechanism.

In use, the antegrade anchor 49 is secured to the interventricular septum by unsheathing the left ventricular disk 57 against the left ventricular surface 16 of the interventricular septum 20, then exposing the septal connector 56, followed by unsheathing the right ventricular disk 54 against the right ventricular surface 17 of the interventricular septum 20. By resheathing the right ventricular disk 54, then septal connector 56, and finally left ventricular disk 57, the antegrade anchor is removed safely from the cardiac wall, either to be repositioned, or to be removed entirely.

The anchor cap 58 comprises at least one locking arm 61 extending radially outwardly from the anchor cap 58. The locking arm 61 is sized and configured for releasably securing a portion of the tether 36 (described below) to the anchor cap 58. The at least one locking arm 61 moves between a first locked position, in which the locking member 61 extends a first distance away from the body of the anchor cap 58, and a second unlocked position in which the locking member 61 extends a second distance away from the anchor cap 58 that is less than the first distance. The anchor cap 58 comprises at least one biasing member (not shown), such as a spring, configured to urge each locking arm 61 to the first locked position. As shown, a plurality of locking arms 61 are provided and are spaced equally around the circumference of the anchor cap 58, though it is contemplated that the locking arms 61 need not be spaced equally.

Figure 6:
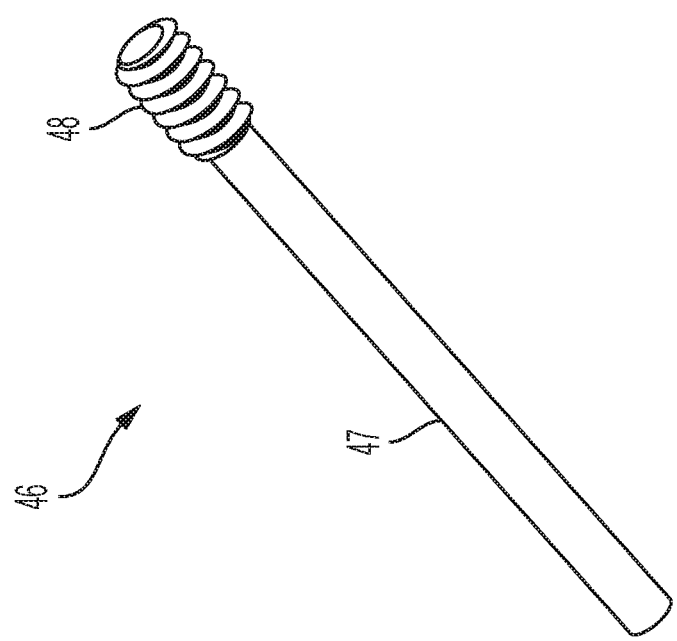
FIG. 6 is a perspective view of the delivery cable of the antegrade anchor for anchoring the transcatheter valve to the anchor.

Now referring to FIG. 6, the delivery cable 46 includes a flexible delivery wire 47 having a distal threaded end portion 48 positioned on or formed in the distal end of the delivery wire 47. Delivery cable 46 has central channel (not shown) that can accommodate the wire rail. The delivery wire is constructed of, but not limited to, stainless steel, nitinol or other metal alloys, with or without hydrophilic coatings, or with or without a polymer coating such as polytetrafluoroethylene (PTFE). The distal threaded end portion 48 is be sized and configured to selectively engage complementary threads formed in a cavity defined in a proximal end 52 of the delivery cable connector 51. See FIGS. 7 and 9. In use, the distal threaded end portion 48 advances, e.g., screws, into via the proximal end 52 of the delivery cable connector 51 to couple the delivery cable connector 51 to the distal end of the flexible wire 47. As described more fully below, the distal threaded end portion 48 is unscrewed from the proximal end of the delivery cable connector 51, detaching the flexible wire 47 from the anchor 49.

The Halo Anchor Assembly

Figure 2:
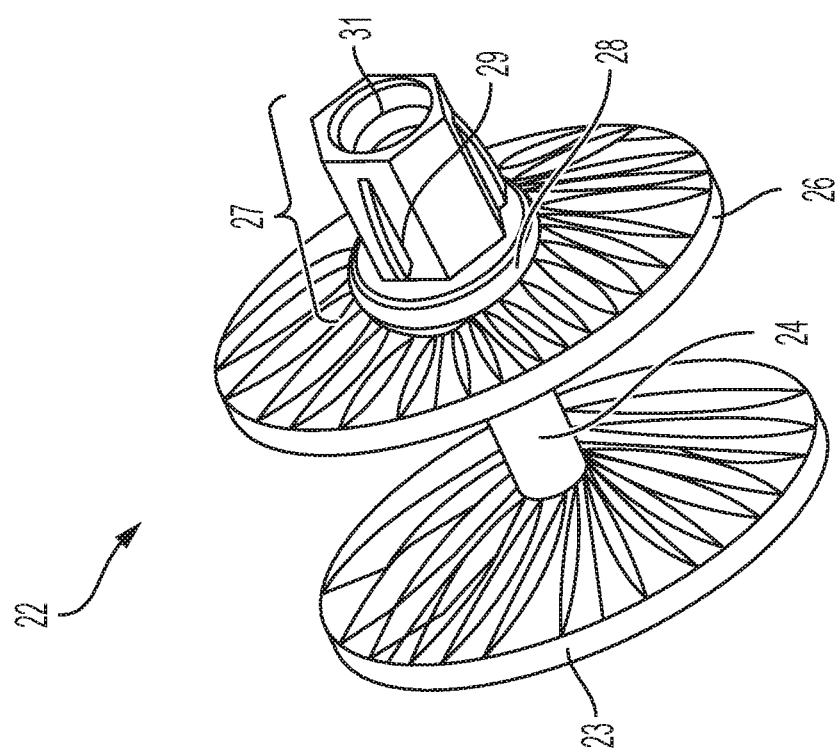
FIG. 2 is a perspective view of a retrograde anchor for anchoring a tether to the interventricular septum.
Figure 5:
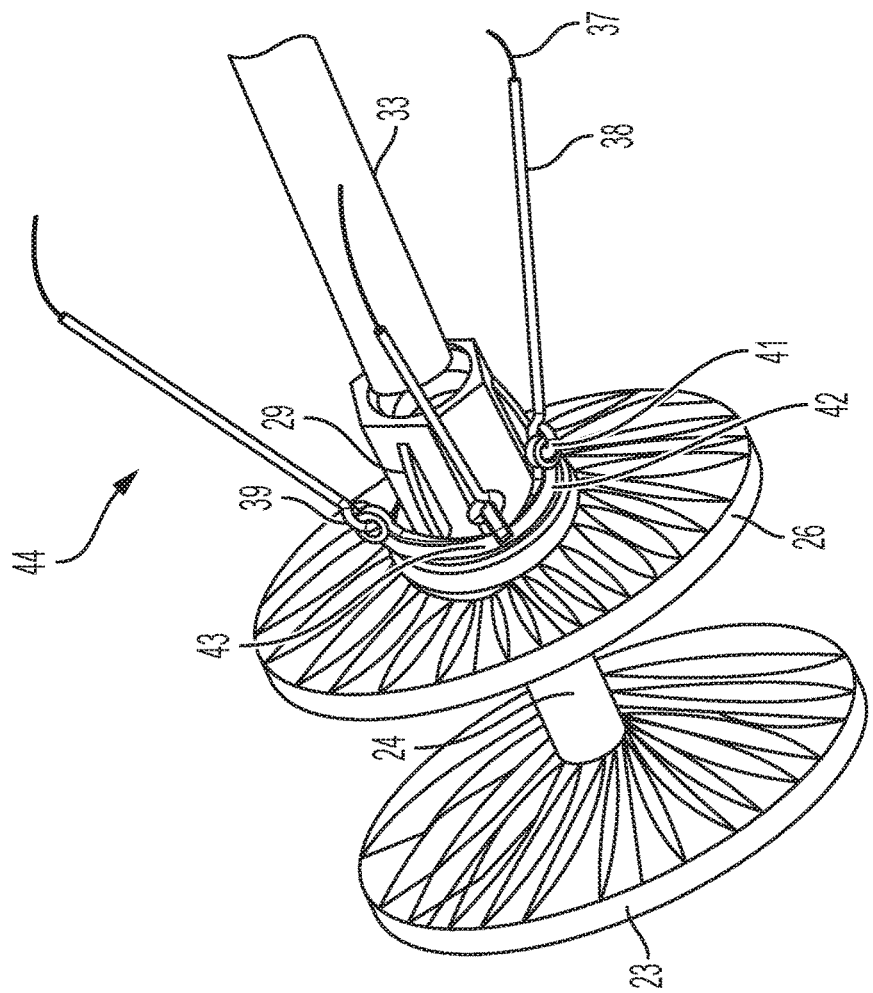
FIG. 5 is a perspective view of the retrograde anchor assembly, comprised of the tether, for connecting the transcatheter valve to the anchor, coupled to the anchor, for anchoring the tether to the interventricular septum with the LV disc of the anchor connected to the delivery cable.
Figure 9:
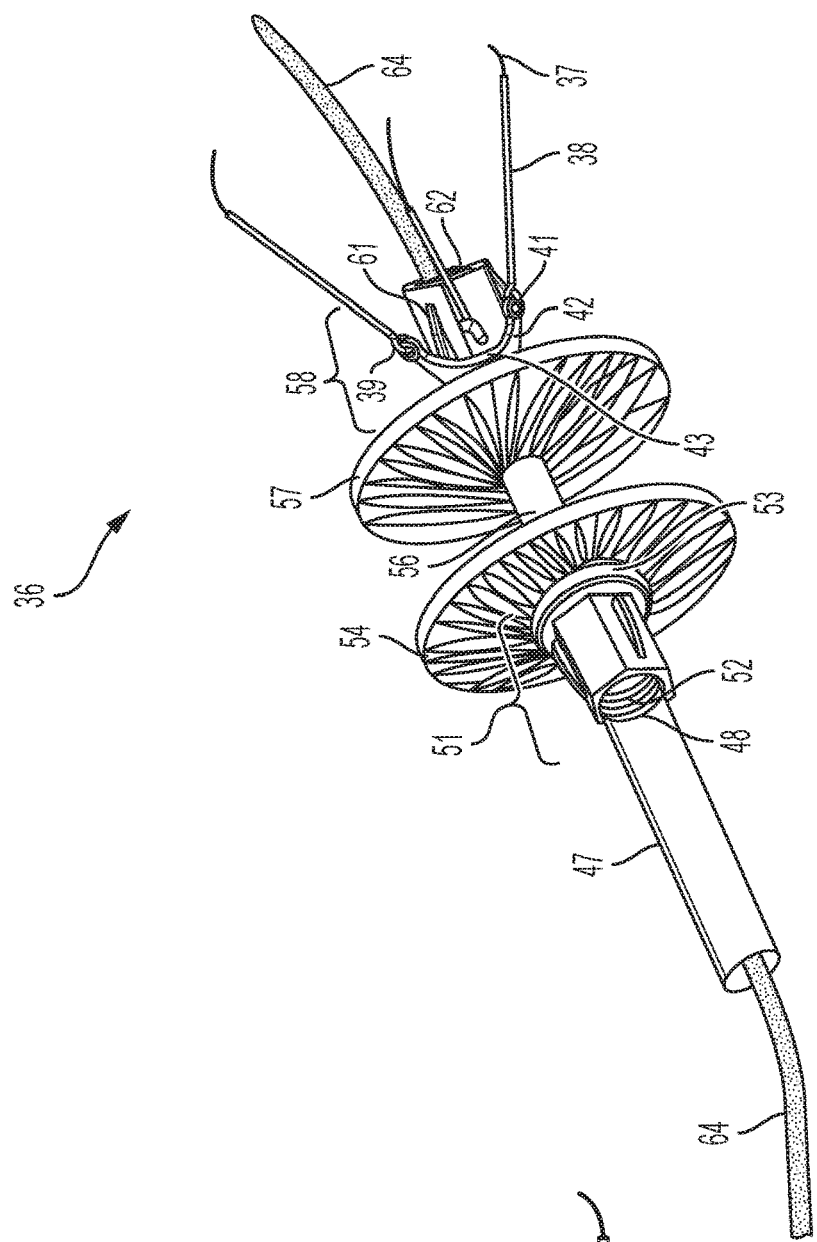
FIG. 9 is a perspective view of the antegrade anchor assembly, comprised of the tether, for connecting the transcatheter valve to the anchor, coupled to the anchor, for anchoring the tether to the interventricular septum with the RV disc of the anchor connected to the delivery cable and a guidewire going through assembly.
Figure 8:
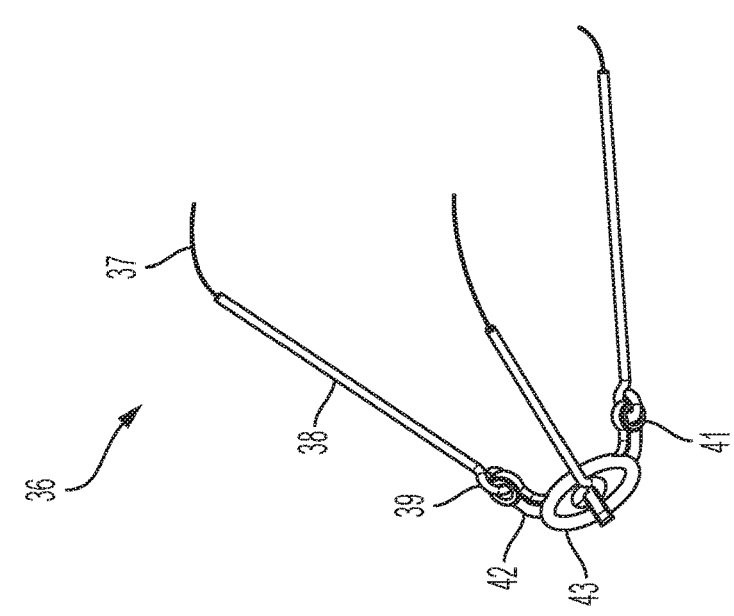
FIG. 8 is a perspective view of the tether for anchoring the transcatheter valve to the antegrade anchor.

According to another aspect of the disclosure, as shown in FIGS. 17A-F, a halo anchor assembly 91 is illustrated. The halo anchor assembly 91 includes an anchor base 94, connected to anchor shaft 92 (that takes the place of an anchor cap 58 according to other aspects) and is fused to the rest of an antegrade anchor 49, although this halo anchor assembly 91 could consist of anchor base 94, connected to anchor shaft 92, taking the place of anchor cap 27 as shown in FIG. 2, fusing to the rest of a retrograde anchor 22. As shown, the antegrade anchor 49 extends distally from an anchor base 94. The anchor base 94 defines at least one, or a plurality as shown, of anchor flanges 96 and recessed areas 97 therebetween. The anchor shaft 92 includes at least one or, as shown, a plurality of locking members 98 shown extended in FIG. 17B. Locking members 98 are biased, such as by a spring (not shown), radially outwardly from the anchor shaft 92. An anchor connector 99 and connector rod 101 travel over wire rail 64 which extends through anchor shaft 92 and threaded end 52, such as illustrated in FIG. 9) wherein anchor connector 99, which is connected to connector rod 101, cooperates with the anchor shaft 92. The anchor connector 99 defines at least one or, as shown, a plurality of apertures 100 configured for receipt of the anchor flanges 96. Accordingly, the anchor connector 99 and connector rod 101 are matingly connected to the anchor shaft 92, thereby urging the locking members 98 inward. The cooperating apertures 100 and the flanges 96 integrate the anchor connector 99 and the anchor base 94. After tether ring 102 is secured by locking members 98, anchor connector 99 and connector rod 101 are removed, leaving wire rail 64 extending through anchor shaft 92 attached to anchor base 94. Regarding the anchor assembly 91 fused to retrograde anchor 22 anchor connector 99 and connector rod 101 travel over delivery cable 32, which remains after anchor connector 99 and connector rod 101 are removed.

Figure 32A:
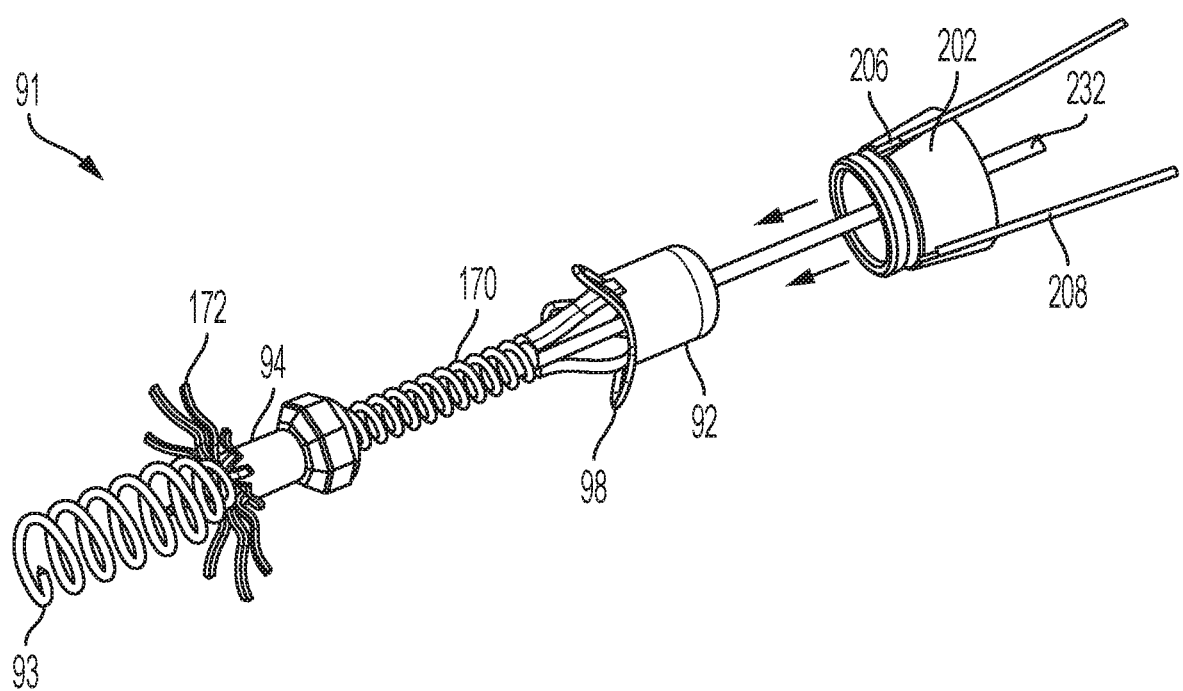
FIG. 32A is an exploded view of an anchor having an anchor screw and anchor cap configured for receipt of connecting ring and a tethering system according to another aspect of the invention.
Figure 32B:
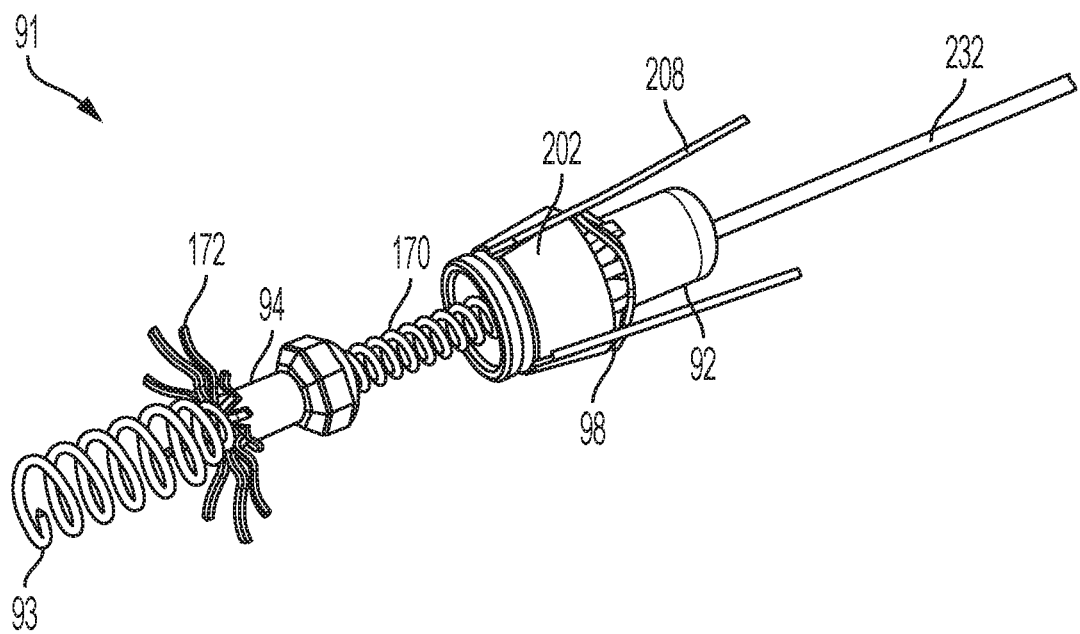
FIG. 32B is a side elevational view of anchoring system of FIG. 32A with connected ring advanced over anchor cap and locked into place.
Figure 32C:
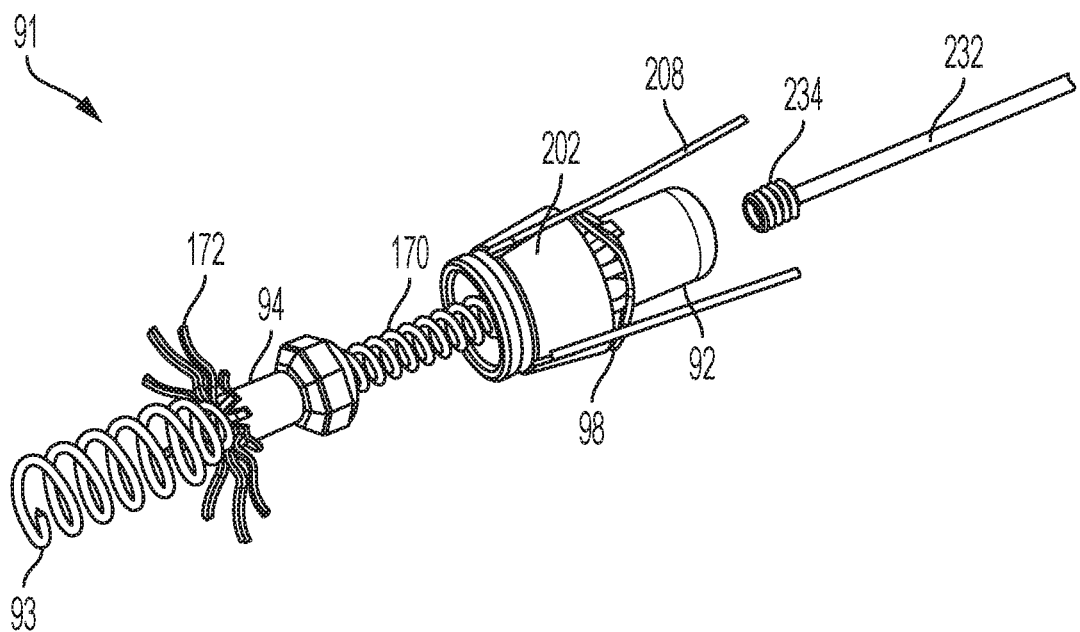
FIG. 32C is a side elevational view of FIG. 32B with the delivery cable disconnected from system.
Figure 33A:
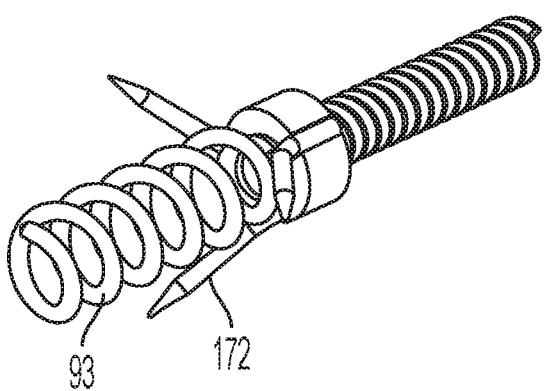
FIG. 33A is a perspective view of the anchor of FIG. 32 with stabilizers according to another aspect of the invention.
Figure 33B:
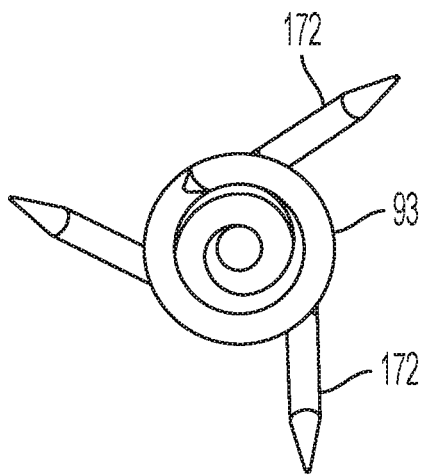
FIG. 33B is an end plan view of the anchor screw of FIG. 32.

FIGS. 32 and 33

Another aspect of the halo anchor assembly is shown in FIGS. 32A-C and 33. The anchor assembly 91 additionally includes a flex connector 170, which may be formed a suitable material such as metal or metal alloy, extending between the anchor base 94 and anchor shaft 92. As shown, the flex connector 170 is a coiled configuration, but other configurations are envisioned. Affixed to the bottom of anchor shaft 92 are at least one, or three as shown, locking arms 98 extending radially outwardly from the anchor shaft 92. Arms 98 are formed, for example, of any metal or metallic alloy. Locking arms 98 are urged radially inward but are biased to the shown. Therefore, locking members 98 cooperate with tether ring 202 when positioned to engage with the locking members 98, and the flex connector of the anchor assembly 91 enables tethers to remain axially aligned with the valve to be implanted (such as, parallel to the interventricular septum), particularly when the anchor screw 93 is implanted.

To implant anchor screw 93, a torque driver (not shown) preloaded over delivery cable 232 mates with anchor base 94 and allows the screw to be rotated and thereby driven into tissue. Once fully implanted, the torque driver is removed, leaving the anchor assembly 91 connected to delivery cable 232. Over delivery cable 232, a tether ring 202, connected to tethers via tether rods 208 (attached to tether ring 202 via apertures 206) is advanced over anchor shaft 92. The tether ring 202 advances over locking arms 98, thereby depressing them inwards. Once the proximal end of the tether ring 202 has passed beneath locking arms 98, locking arms 98 spring outward, thereby restraining the tether ring 202 in place, preventing it from unintended movement by the tethers affixed to tether rods 208. Finally, the delivery cable 232 is rotated so that the "male" threads 234 are disengaged from the threads defined by the threaded cavity of the anchor shaft 92.

The anchor assembly 91 shown in these drawings also includes stabilizers 172 to stabilize the anchor and limit or prevent movement, such as rotational movement, from tension transferred from the tethers and to provide traction to limit or prevent the screw anchor 93 from inadvertently rotating so as to uncouple from the tissue in which it was implanted. At least one stabilizer 172 may be provided. As shown in FIG. 32, eight stabilizers 172 are illustrated and FIG. 33 illustrates three. As shown in FIG. 32, the stabilizers 172 extend radially outward from the longitudinal axis of the anchor. The stabilizers 172 are configured to have a non-linear configuration. Other configurations are envisioned. The stabilizers 172 shown in FIG. 33 also extend radially outwardly form the anchor longitudinal axis and extend at an acute angle, for example 45 degrees, along the horizontal axis. The angle is generally facing the opposite direction of the screw anchor 93. The stabilizers are generally linear, but other configurations are envisioned. When inserted into the interventricular septum, for example, the stabilizers 172 will urge against and perhaps into the tissue in a direction opposite the anchor screw implantation to prevent unintentional withdrawal of the anchor screw 93.

After the halo anchor assembly, consisting of either an antegrade anchor 49 or retrograde anchor 22, has been implanted, a tether ring 102 is applied over the connector rod 101 and anchor connecter 99 and abuts the anchor base 94, fused to an antegrade anchor 49 or a retrograde anchor 22. The tether ring 102 includes a generally cylindrical first distal portion and a second proximal portion 104 having a diameter greater than the first portion 103. The second portion 104 defines at least one or, as shown, a plurality of apertures 106 configured for receipt of tether rods 108 as shown in FIGS. 17E and 17F. As shown in FIG. 17D, the anchor connector 99 and connector rod 101 are removed. The locking members 98 are urged radially outward so as to engage the second portion 104 of the tether ring 102 to lock the tether ring 102 on the anchor base 94. Tether rods 108 are operative as described above for cooperating with a transcatheter heart valve 66 or 156.

The Tether Assembly

Figure 4:
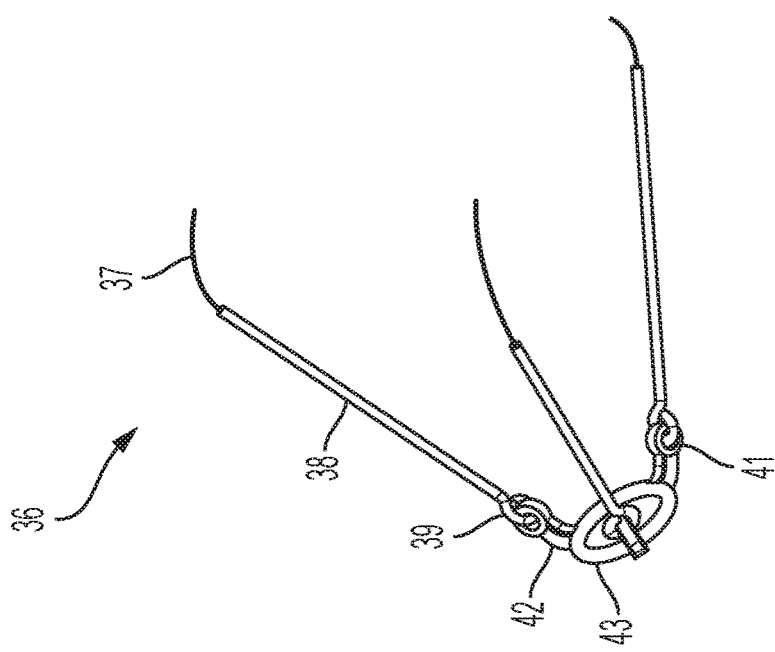
FIG. 4 is a perspective view of a tether for anchoring the transcatheter valve to the retrograde anchor.
Figure 7:
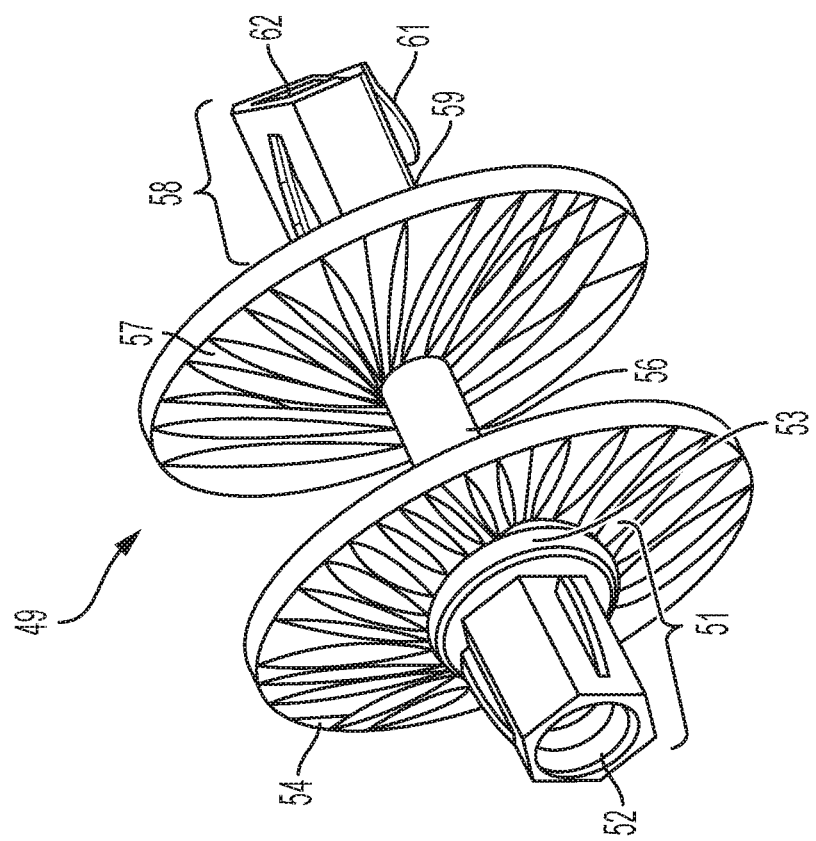
FIG. 7 is a perspective view of an antegrade anchor for anchoring a tether to the interventricular septum

When the flexible wire 33 is coupled to the retrograde anchor 22, the flexible wire serves as a guide rail for the advancement of the tether 36 to the retrograde anchor 22. For the antegrade anchor 49, the wire rail 64 serves as a guide rail of the tether 36 to the antegrade anchor 49, by entering the distal end 62 of anchor cap 58, exiting the delivery cable connector 51 via the threaded end 52 through the central channel of delivery cable 46. The tether 36 includes one or more tether rods 38 rotatably connected to a docking ring 43. The tether rods 38 are connected to an eyelet 41 defined by docking ring arms 42 as shown in FIG. 4. The tether 36 is advanced either over the flexible wire 32 of delivery cable 33 (in case of retrograde anchor) or over the wire rail 64 (in case of antegrade anchor), and the docking ring 43 of the tether 36 depresses the at least one locking arm 29 or 61 of the anchor cap 27 or 58, to the second unlocked position. With the locking arm 29 or 61 in the second position, the tether 36 advances over the locking arm 29 or 61 on the anchor cap 27 or 58, respectively, until the docking ring 43 abuts and/or is adjacent to a distal end 28 of the anchor cap 27, or to a distal end 59 of the anchor cap 58. At this point, the biasing member of the anchor cap 27 or 58 urges the at least one locking arm 29 or 61 to the first locked position, thereby releasably coupling the docking ring 43, and thus the rest of the tether 36, to the retrograde anchor 22 or to the antegrade anchor 49.

In one aspect, when coupled to the retrograde anchor 22 or to the antegrade anchor 49, the tether 36 rotates about a longitudinal axis of the anchor a full 360 degrees. Optionally, in another aspect, the tether 36 may be constrained to lesser degrees of rotation by interaction of a portion of the tether 36 with the at least one locking arm 29 or 61.

As shown in FIG. 4, in one aspect, the tether 36 comprises at least one docking ring arm 42 coupled to the docking ring 43, and at least one tether rod 38 coupled a docking ring arm 42. As shown, a distal end of the docking ring arm 42 is securely coupled to or formed monolithically with the docking ring 43. As shown, the at least one docking ring arm comprises a plurality of docking ring arms 42. As shown, the plurality of docking ring arms 42 are spaced equally around the circumference of the docking ring, though it is contemplated that the docking ring arms 42 need not need spaced equally. An eyelet 41 is defined by the docking ring arm 42. The tether rod 38 includes a tether rod hook 39 configured for cooperating with the eyelet 41.

A proximal end of each docking ring arm 42 is rotatably coupled to a distal end of a respective tether rod 38. A tether rod hook 39 is defined by the tether rod 38 as shown and is either coupled to or formed monolithically with the distal end of each tether rod 38. In another aspect, the eyelet 41 and the tether rod hook 39 are sized and configured so that the tether rod hook 39 is inserted into the eyelet 41 to securely, rotatably couple the tether rod 38 to the docking ring 43. In use, each tether rod hook 39 rotates about the circumference of the eyelet 41. As shown in FIG. 4, the proximal end of each tether rod is coupled to a cord 37. The tether rod 38 and the tether rod hook 39 may be composed of any metal alloy.

The Wire Rail Delivery System

Figure 18B:
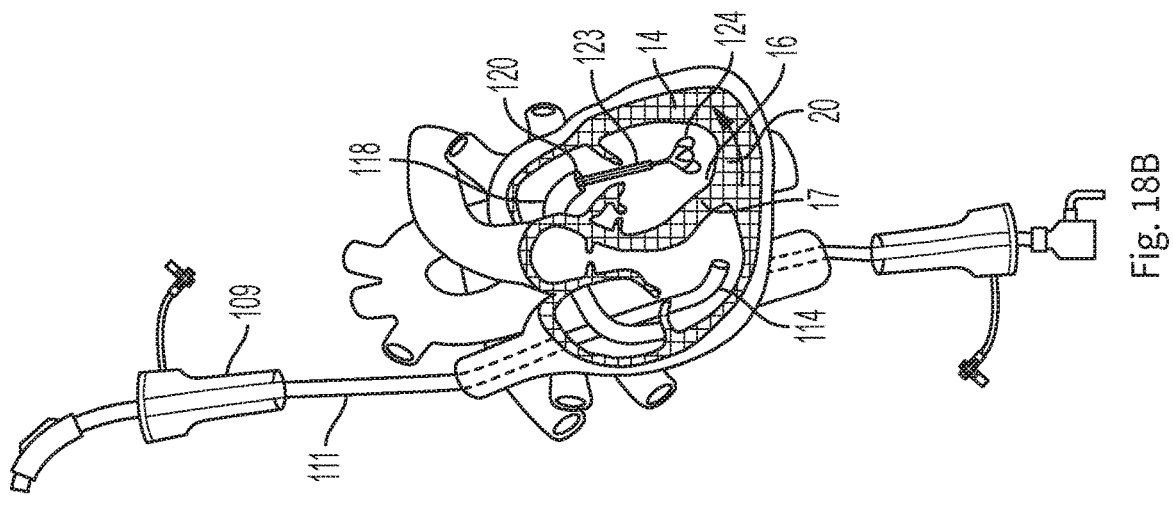
FIG. 18B is a perspective view of the snare being positioned in the left ventricle after trans-septal puncture.
Figure 18A:
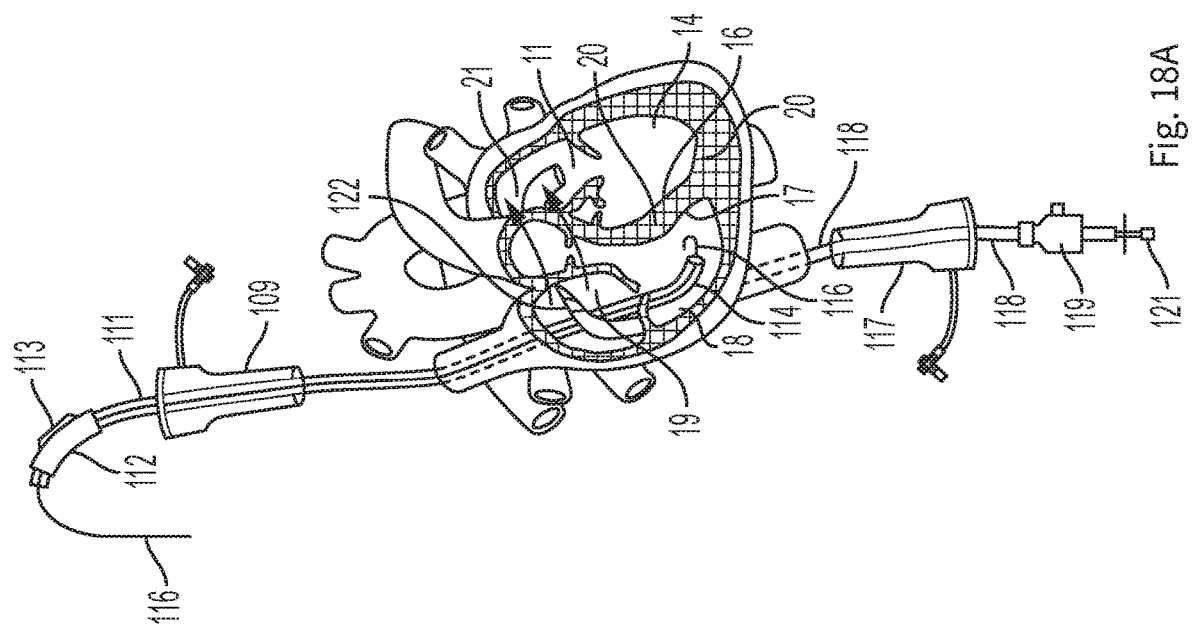
FIG. 18A is a perspective view of the trans-septal puncture being performed and the interventricular septal crossing guide in position.

Referring now to FIGS. 18A and 18B, the wire rail delivery system consists of an interatrial transseptal guide 118 and an interventricular transseptal guide 111. The interatrial transseptal guide 118 is inserted into a femoral vein via the trans-femoral sheath 117, and the guide 118 has a proximal hub 119, through which a transseptal needle 121 is introduced, and this needle 121 exits the trans-septal guide 121 though the distal dilator 122 of the guide. The interventricular transseptal guide 111 is inserted into a jugular vein via the trans jugular sheath 109 and is guided into the right ventricle 18 over a guidewire 116. The interventricular transseptal guide 111 has a deflectable distal tip 114 that is controlled by the deflection knob 113 attached to the proximal handle 112 of the guide, and the tip can be deflected toward the right ventricular surface 17 of the interventricular septum 20.

The Antegrade and Retrograde Anchor Delivery Sheaths

Figure 21A:
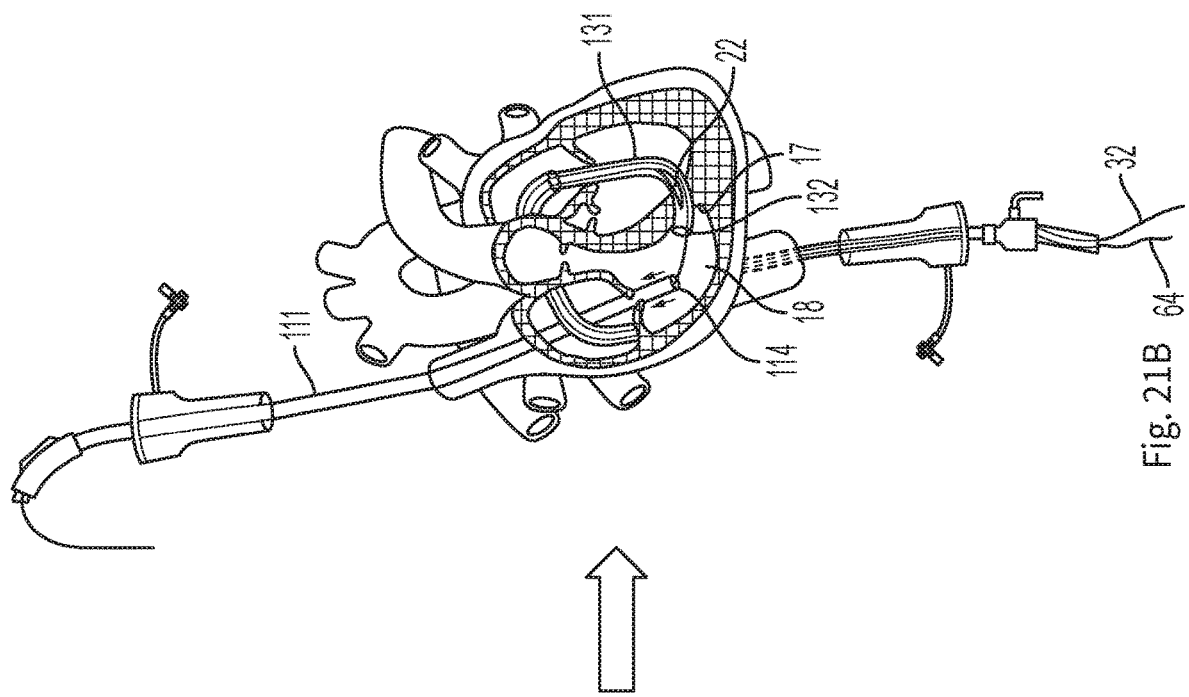
FIG. 21A is a perspective view of the retrograde anchor delivery sheath advancing over the 0.035" rail wire to the interventricular septum.
Figure 21B:
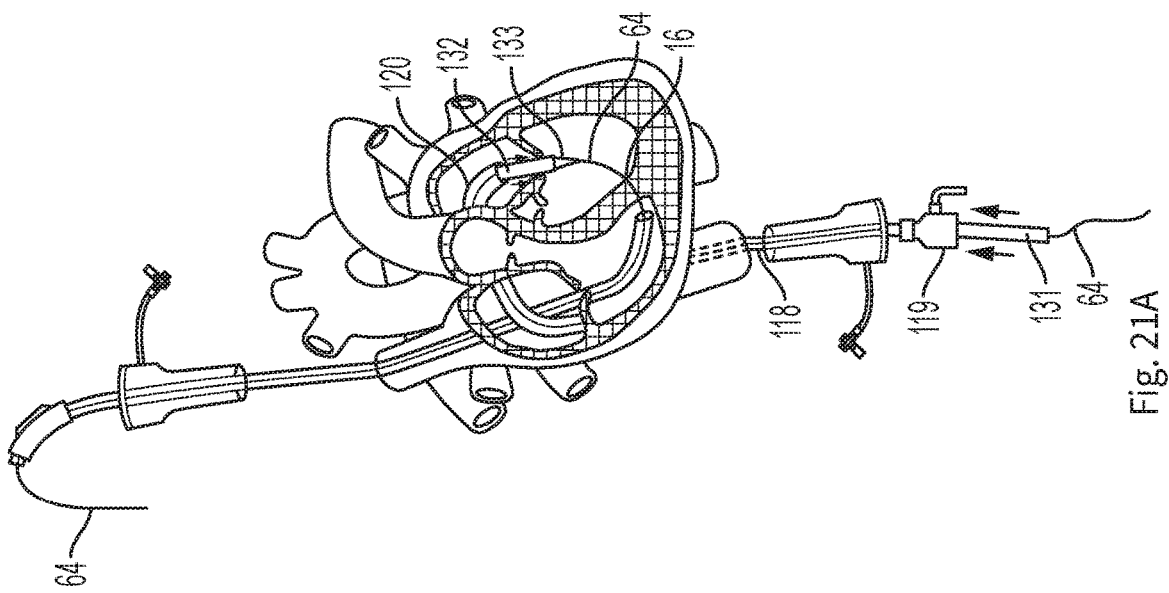
FIG. 21B is a perspective view of the retrograde anchor delivery sheath positioned across the interventricular septum with its end in the right ventricle and the retrograde anchor positioned inside the sheath.

Referring now to FIGS. 21A and 21B, the retrograde anchor delivery sheath 131 goes over wire rail 64 into the proximal hub 119 of the interatrial transseptal guide 118 and exits the distal end 120 of the transseptal guide. Through the distal end 132 of the retrograde anchor delivery sheath 131 is the dilator 133, which goes over the wire rail 64 and enters the left ventricular surface 16 of the interventricular septum 20 until it exits the right ventricular surface 17 of the interventricular septum 20. Once across, the dilator 133 is removed, leaving the distal end 132 of the retrograde anchor delivery sheath in the right ventricle 18 to allow delivery of the retrograde anchor 22.

Figure 24A:
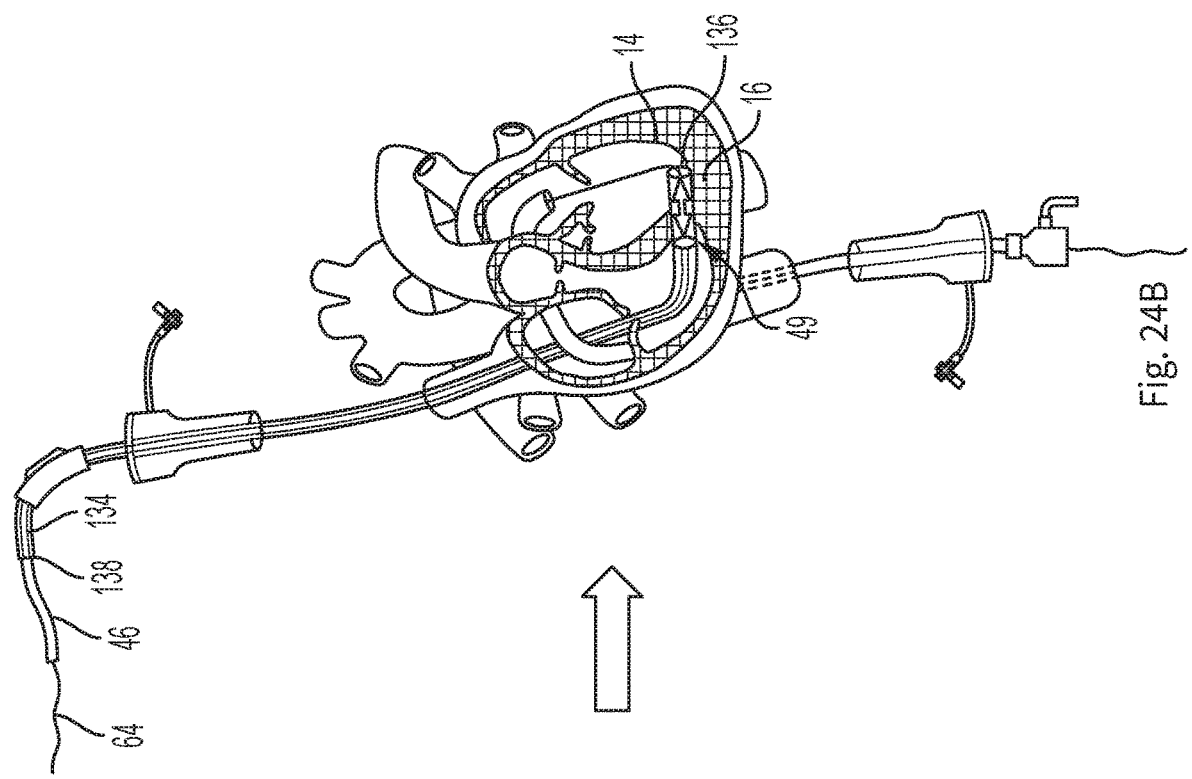
FIG. 24A is a perspective view of the antegrade anchor delivery sheath advancing through the septum over the 0.035" rail wire.
Figure 24B:
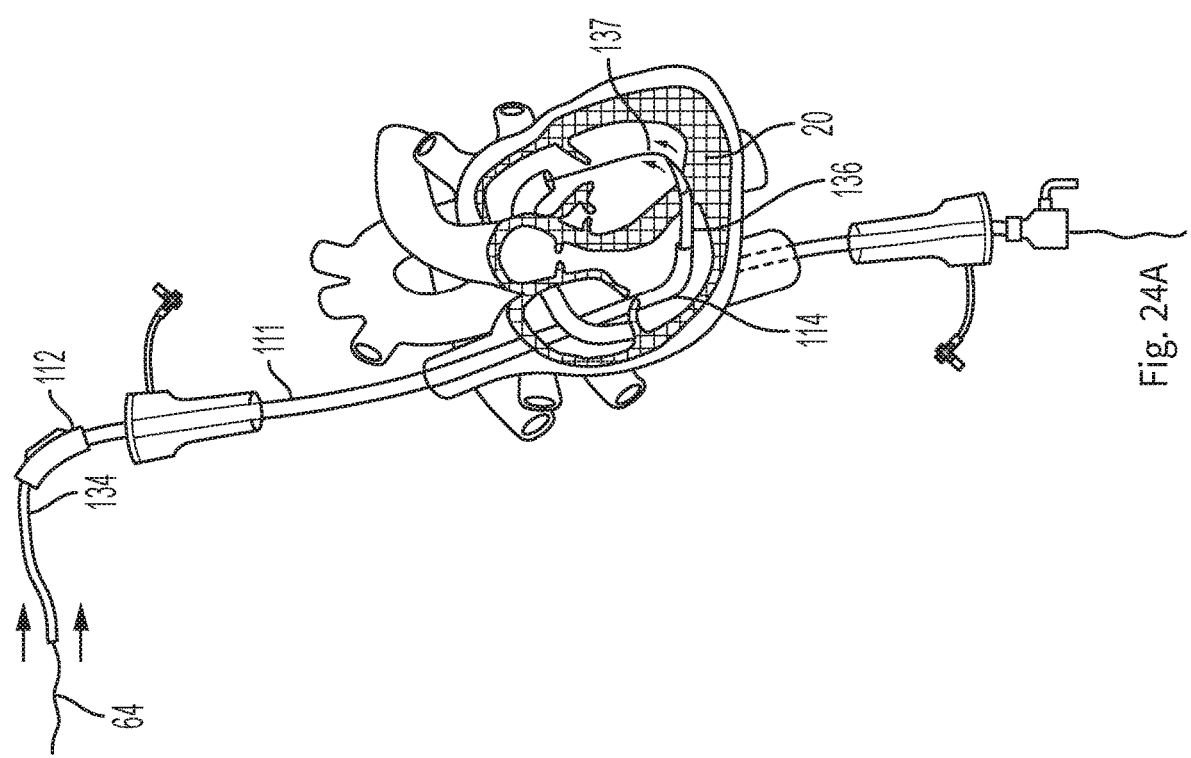
FIG. 24B is a perspective view of the antegrade anchor delivery sheath positioned across the interventricular septum with its end in the left ventricle and the antegrade anchor positioned inside the sheath.

Referring now to FIGS. 24A and 24B, the antegrade anchor delivery sheath 134 goes over wire rail 64 into the proximal handle 112 of the interventricular transseptal guide 111 and exits the distal end 114 of the transseptal guide. Through distal end 136 of the antegrade anchor delivery sheath 134 is the dilator 137, which goes over the wire rail 64 and enters the right ventricular surface 17 of the interventricular septum 20 until it exits the left ventricular surface 16 of the interventricular septum 20. Once across, the dilator 137 is removed, leaving the distal end 136 of the antegrade anchor delivery sheath in the left ventricle 14 to allow delivery of the antegrade anchor 49.

As shown, in FIG. 18A a sheath 109 is configured to receive the interventricular transseptal guide 111, and a sheath 117 is configured to receive the interatrial transseptal guide 118. The sheath 109 is in fluid communication with the interventricular transseptal guide 111, and the sheath 117 is in fluid communication with the interatrial transseptal guide 118, so that fluids, such as heparinized saline and the like surround the interventricular transseptal guide 111 through sheath 109 and surround the interatrial transseptal guide 118 through sheath 117.

The Method of Creating the Wire Rail

As shown in 18A, a J-wire 116 is introduced via sheath 109 and endovascularly guided by the user into the right ventricle 18. Over the J-wire 116, the interventricular transseptal guide 111 is advanced into the sheath 109 and endovascularly guided by the user into the right ventricle 18. Once in the right ventricle 18, J-wire 116 is removed, and the guide tip 114 is deflected by the deflection knob 113 of the proximal handle 112 of the interventricular transseptal guide 111, until the guide tip 114 is adjacent to the right ventricular surface 17 of the interventricular septum 20.

As shown in 18A, a J-wire (not shown) is introduced via sheath 117 and endovascularly guided by the user into the right atrium 19. Over this J-wire, the interatrial transseptal guide 118, with dilator 122 extending out of distal tip 120 of the guide, is endovascular guided by user until it is in right atrium 19. Then, the J-wire is removed, and a transseptal needle 121 is advanced through the proximal hub 119 of the interatrial transseptal guide 118, until the needle is close to the end of the dilator 122. Next, the proximal hub 119 of the interatrial transseptal guide 118 is withdrawn and rotated until the dilator 122, extending out of the distal tip 120, is pushing against the interatrial septum 21. Using fluoroscopic and echocardiographic guidance, the transseptal needle 121 is advanced across the interatrial septum 21 into the left atrium 11, followed by advancement of the dilator 122 and distal tip 120 of the interatrial transseptal guide 118. Once distal tip 120 is in the left atrium 11, the dilator 122 and transseptal needle 121 are both withdrawn from the proximal hub 119 of the interatrial transseptal guide 118.

As shown in FIG. 18B, a snare sheath 123 is introduced into the proximal hub 119 of the interatrial transseptal guide 118 until the snare sheath 123 exits of the distal tip 120 of the guide 118, advances from the left atrium 11 into the left ventricle 14. A snare 124 is advanced via the snare sheath 123 into the left ventricle 14 until the snare 124 is adjacent to the left ventricular surface 16 of the interventricular septum 20.

As shown in FIG. 19A, a radiofrequency wire 127, connected to a radiofrequency generator 126 or electrocautery system (not shown), is advanced via the proximal handle 112 of the interventricular transseptal guide 111, until the wire 127 exits the distal end 114 of the interventricular transseptal guide 111, and crosses the interventricular septum 20 into the left ventricle 14, followed by capture of wire 127 by snare 124. As shown in FIG. 19B, the snare 124 pulls the wire 127 into the interatrial transseptal guide 118, until the wire exits the proximal hub 119 of the guide 118. Next, over portion of wire 127 extending from the proximal handle 112 of the interventricular transseptal guide 111, a microcatheter 128 is advanced over wire 127 across the interventricular septum 120 FIG. 19C shows a magnified view of the microcatheter 128, with a distal dilator 129, advancing across the interventricular septum 20 over the wire 127.

Figure 20B:
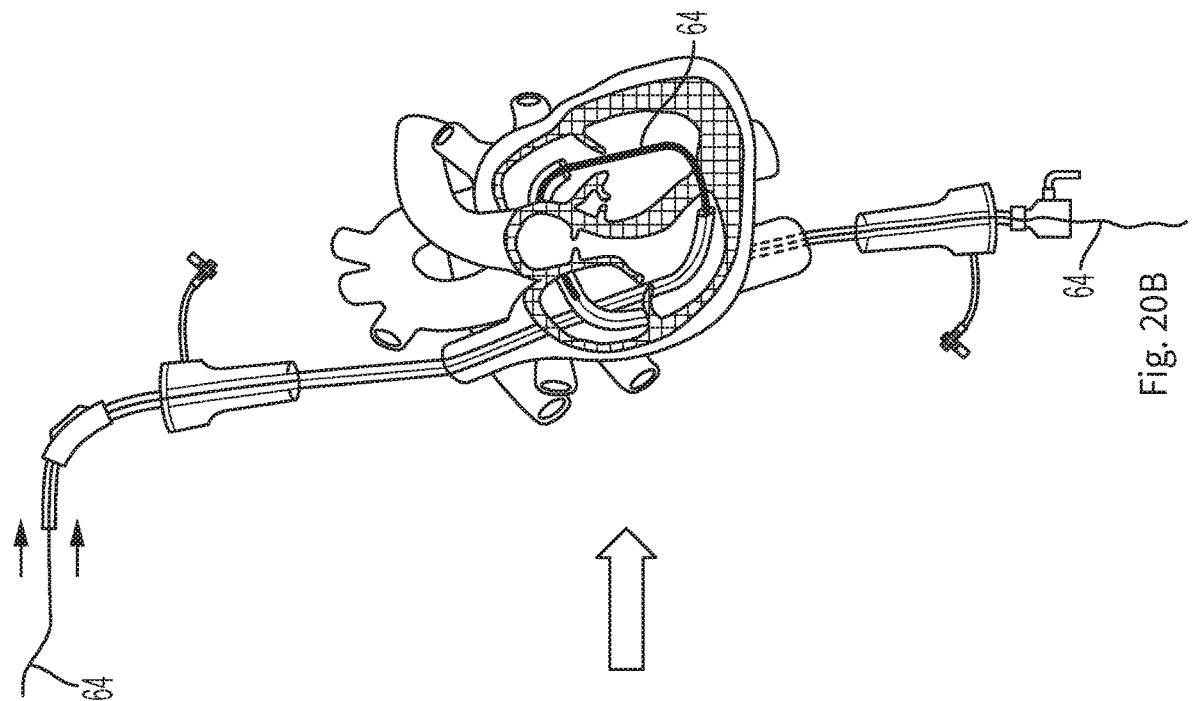
FIG. 20B is a perspective view of the interventricular septal crossing wire being exchanged to a 0.035" wire.
Figure 20A:
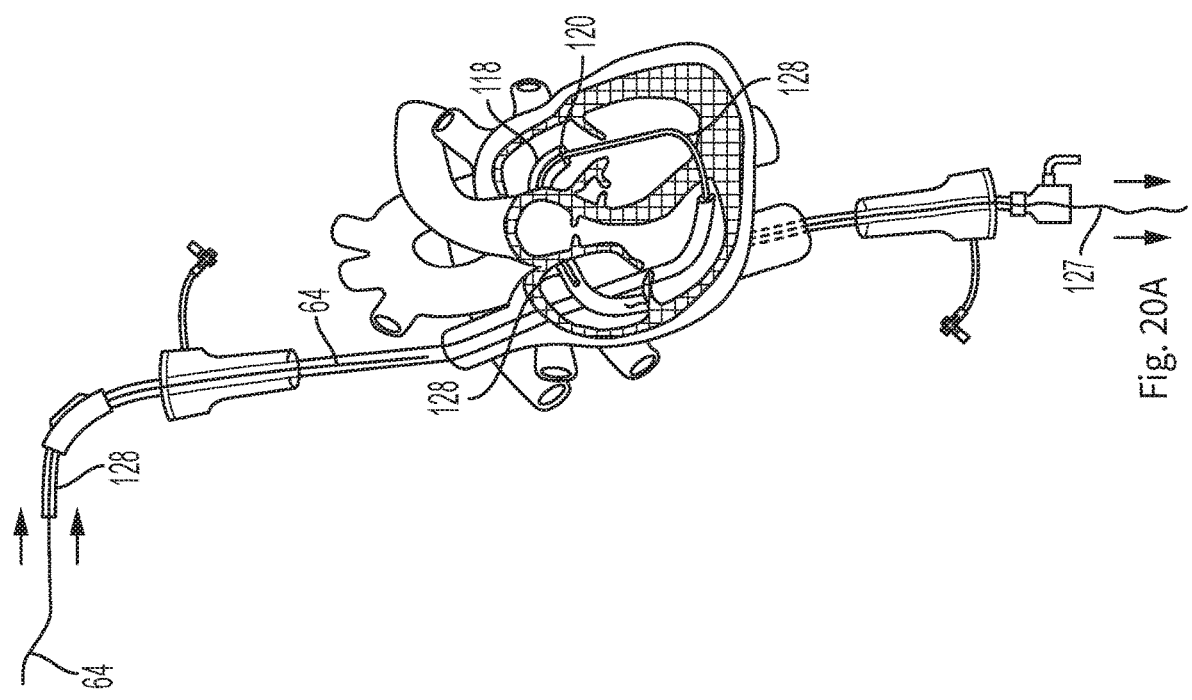
FIG. 20A is a perspective view of the interventricular septal crossing catheter advancing into the trans-septal guide.

As shown in FIG. 20A, the microcatheter 128, is advanced over wire 127 until it enters distal tip 120 of the interatrial transseptal guide 118. Once the microcatheter 128 is several or more centimeters inside the interatrial transseptal guide 118, the wire 127 is removed by pulling out of the proximal hub 119 of the interatrial transseptal guide 118. As shown in FIG. 20B, a larger and stiffer J-wire 64 is advanced through the interventricular transseptal guide 111 via microcatheter 128, until the J-wire 64 exits the microcatheter 128, positioned inside interatrial transseptal guide 118, and finally exits the proximal hub 119 of the guide 118.

The Method of Implanting the Retrograde Anchor

As described in [0018] and shown in FIGS. 21A and 21B, once the retrograde anchor sheath 131 is positioned in the right ventricle 18 adjacent the right ventricular surface 17, the retrograde anchor 22 is adjacent to wire 64 through the retrograde anchor sheath 131 and positioned at the distal tip 132.

As shown in FIG. 22A, the distal tip 132 of the retrograde anchor sheath 131 is first retracted back until it is in the left ventricle 14 adjacent to the left ventricular surface 16. As the distal tip 132 is retracted back, the self-expanding right ventricular disk 23 of the retrograde anchor 22 deploys, abutting the right ventricular surface 17 of the interventricular septum 20, and the septal connector 24 is exposed in the interventricular septum 20. As shown in FIG. 22B, as the distal tip 132 is further retracted the self-expanding left ventricular disk 26 deploys, abutting the left ventricular surface 16 of the interventricular septum 20. Next, the retrograde anchor sheath 131 is removed from the proximal hub 119 of the interatrial septal guide 118, and the J-wire 64 is removed by pulling it from the proximal handle 112 of the interventricular transseptal guide 111.

Figure 23:
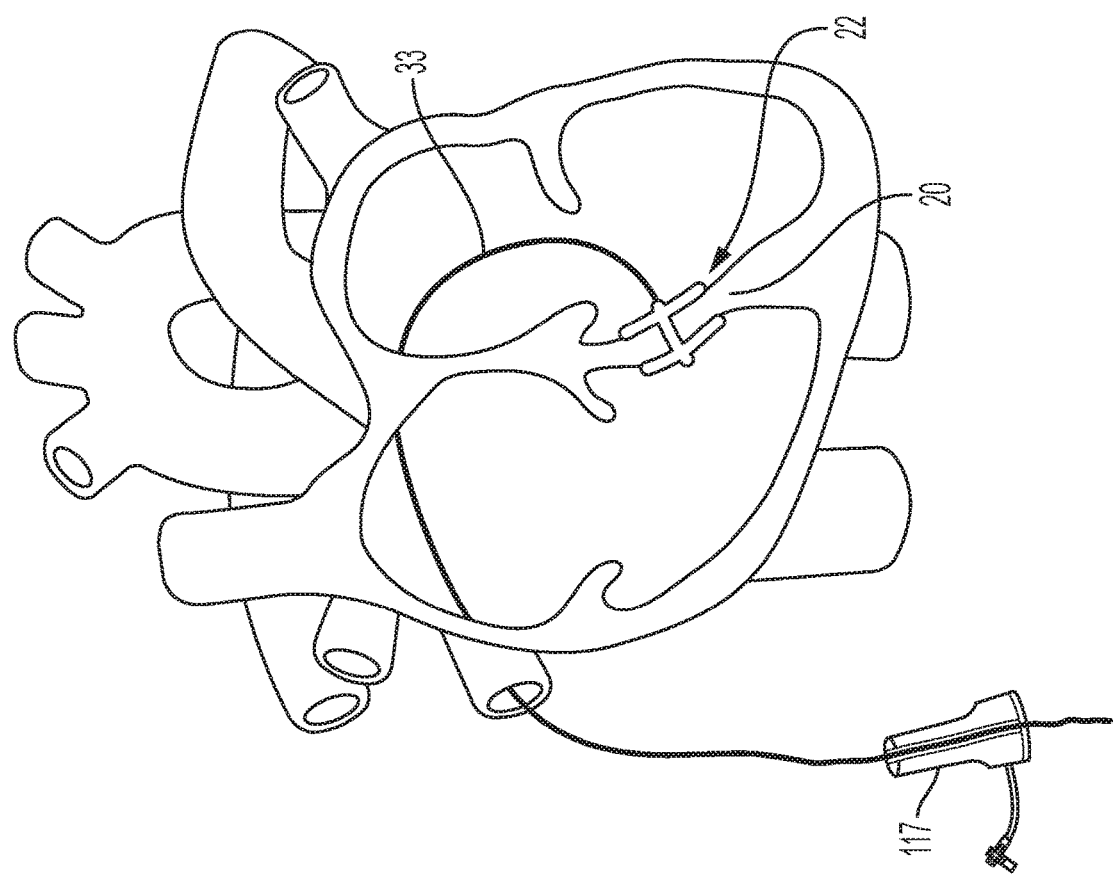
FIG. 23 is a perspective view of the retrograde anchor fully deployed ready to receive transcatheter valve.

As shown in FIG. 23, the interatrial transseptal guide 118 has been pulled out of the body via the transfemoral sheath 117, leaving the retrograde anchor 22 in position, and still connected to the flexible wire 33 of the delivery cable 32.

The Method of Implanting the Antegrade Anchor

As described in [0019] and shown in FIGS. 24A and 24B, once the antegrade anchor sheath 134 is positioned in the left ventricle 14 adjacent the left ventricular surface 16, the antegrade anchor 49 is advanced over the wire 64 through the antegrade anchor sheath 134 and positioned at the distal tip 136.

Figure 25A:
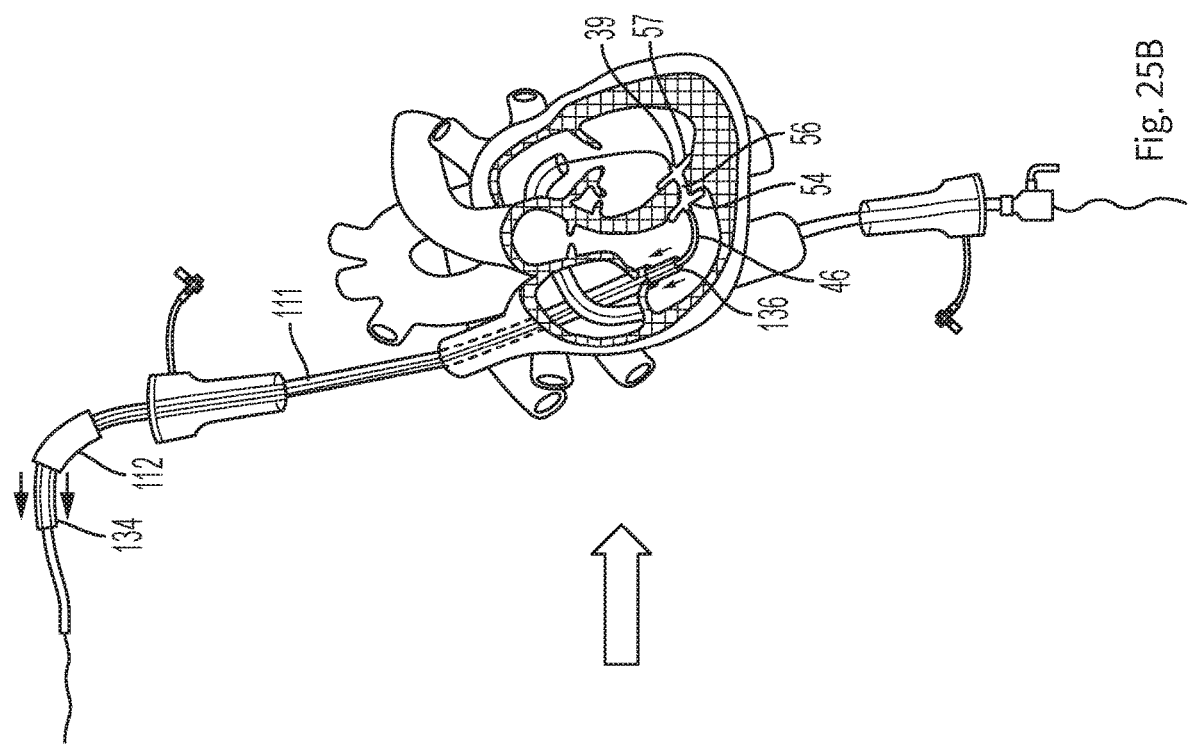
FIG. 25A is a perspective view of the left ventricular disc of the antegrade anchor being deployed.
Figure 25B:
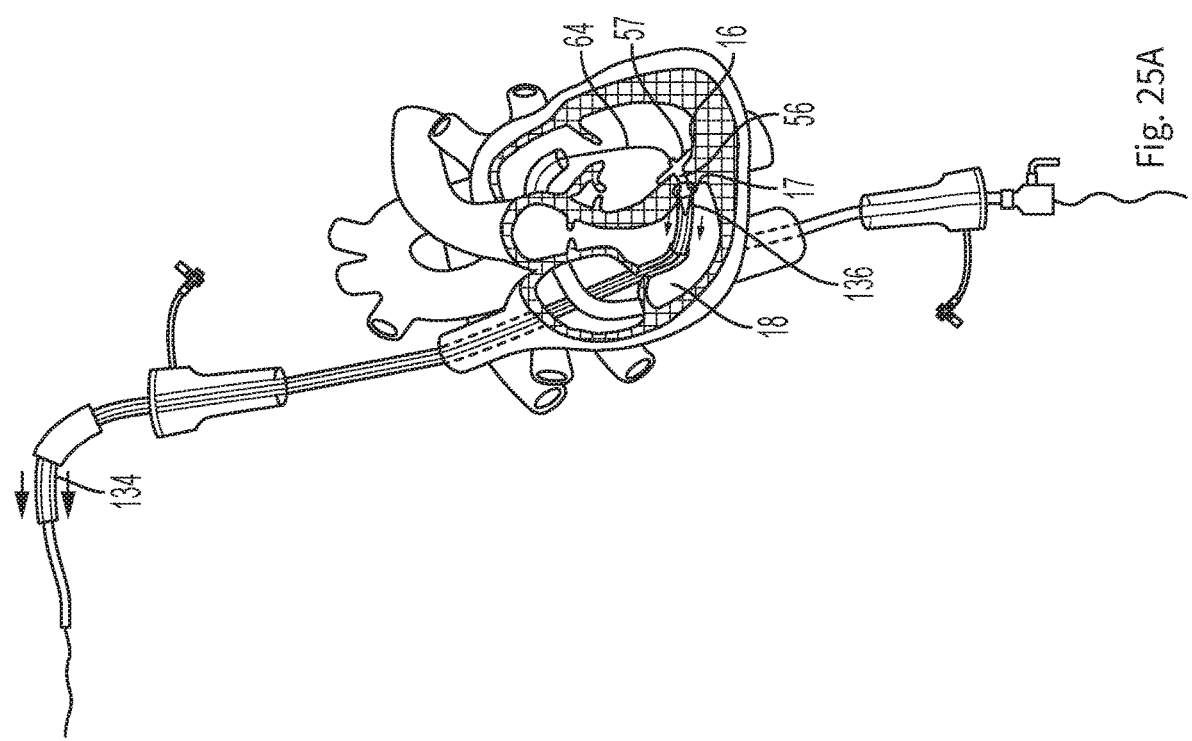
FIG. 25B is a perspective view of the right ventricular disc of the antegrade anchor being deployed.

As shown in FIG. 25A, the distal tip 136 is first retracted back until it is in the right ventricle 18 adjacent to the right ventricular surface 17. As the distal tip 136 is retracted back, the self-expanding left ventricular disk 57 of the antegrade anchor 49 deploys, abutting the left ventricular surface 16 of the interventricular septum 20, and the septal connector 56 is exposed in the interventricular septum 20. As shown in FIG. 25B, as the distal tip 136 is further retracted the self-expanding right ventricular disk 54 deploys, abutting the right ventricular surface 17 of the interventricular septum 20. Next, the antegrade anchor sheath 134 is removed from the proximal handle 112 of the interventricular septal guide 111.

As shown in FIGS. 26A-B, the delivery cable 46 is unscrewed so that its distal thread end 48 detaches from delivery connector 51, allowing flexible wire 47 of the delivery cable 46 to be removed. As shown in FIG. 26C, the interatrial transseptal guide 118 has been pulled out of the body via the transfemoral sheath 117, leaving antegrade anchor 49 in position, with wire 64 running through it.

The Transcatheter Valve

As shown in FIG. 10A, 10B, 11A, 11B, the system 10 comprises a transcatheter heart valve 66 having an atrial sealing skirt top brim 67 extending circumferentially along the upper end of the transcatheter heart valve 66. The transcatheter heart valve 66 includes a transcatheter valve body 68, shown substantially cylindrical, and the atrial sealing skirt top brim 67 which is configured to conform to the left atrial floor 12, as shown. The transcatheter heart valve 66 is coupled to the retrograde anchor 22 or the antegrade anchor 49 by the tether 36 as described herein. The cord 37, fused or otherwise coupled to the tether rod 38 of tether 36, connects the transcatheter heart valve 66 to the anchor 22 or 49 when the anchor 22 or 49 is fixated to the interventricular septum 20.

Figure 11B:
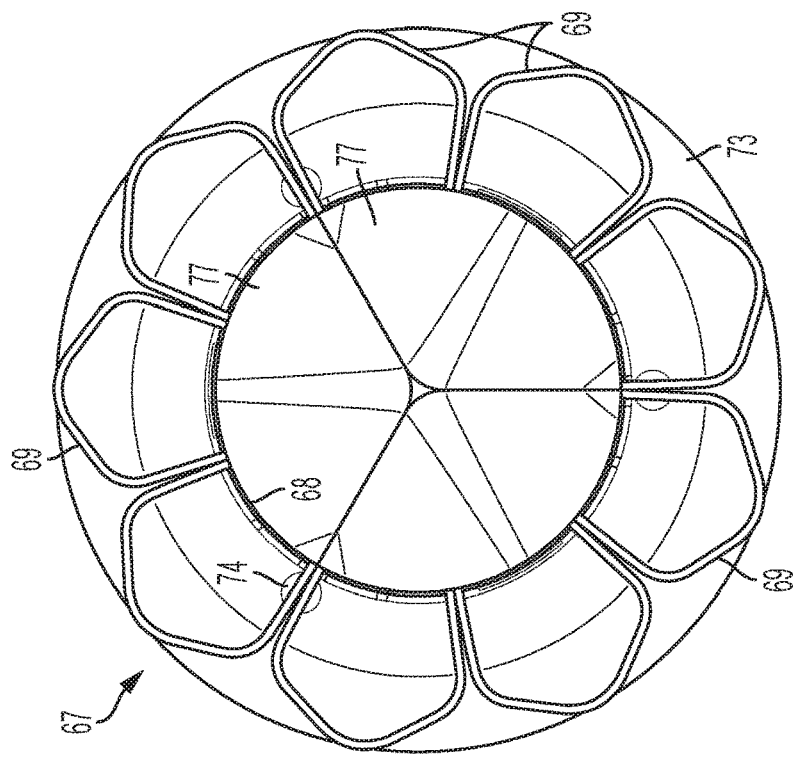
FIGS. 11A and 11B are perspective and top plan views of the valve, composed of the top brim attached to the transcatheter valve body with integrated valve leaflets.
Figure 11A:
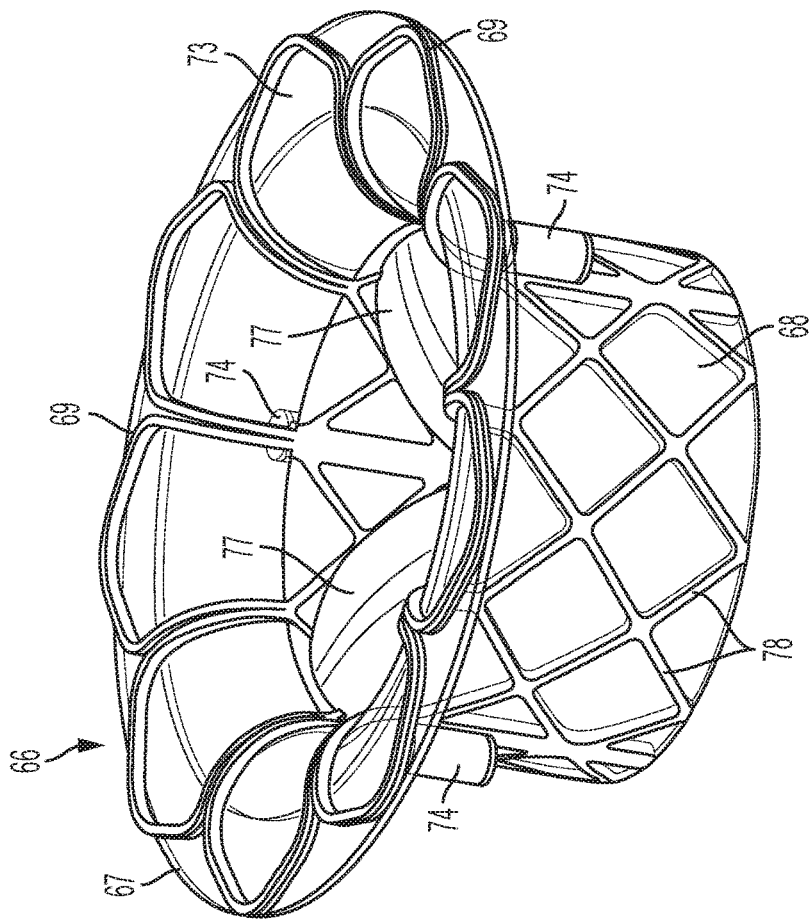

The transcatheter heart valve 66 is sized and configured to sit in the mitral valve between the left atrium 11 and the left ventricle 14 as illustrated in FIG. 1. The transcatheter heart valve 66 is pre-assembled with valve leaflets 77 (FIG. 11A, 11B). This is by way of example. Accordingly, then, with slight variations, these devices, systems, and methods may be endovascularly placed by a venous structure including, but not limited to, either internal jugular vein, either subclavian vein, either subclavian vein or either femoral vein.

The transcatheter heart valve 66 is self-expanding (i.e. the valve is compressible so that it fits through a catheter of system 1) and composed of nitinol, but may also contain elements made of, but not limited to, stainless steel, nitinol or other metal alloys. In another aspect, the transcatheter heart valve has a lower diameter that is smaller than or approximately equal to the annulus at the site deployment 13 of the mitral annulus thereby reducing constraint of the mitral annulus.

Figure 31B:
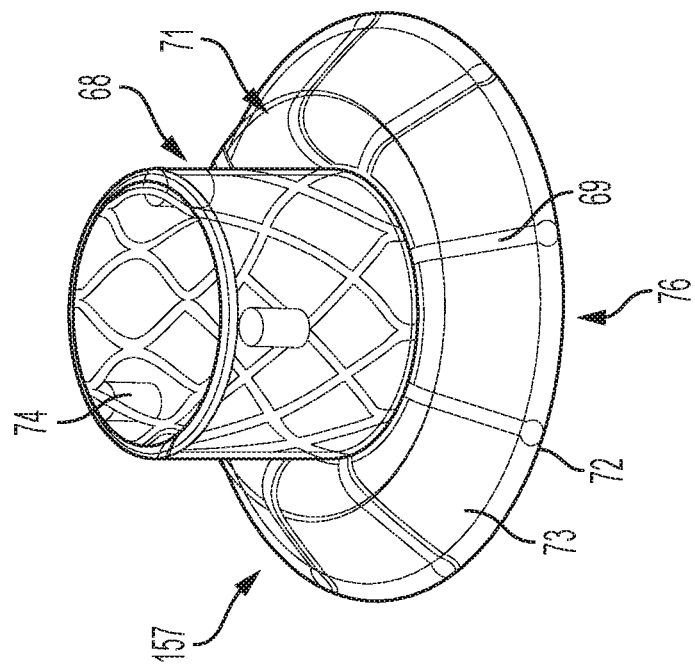
FIGS. 31A and 31B are side elevational view and top perspective views of the supra-annular valve, composed of the top brim attached to transcatheter valve body with integrated valve leaflets.
Figure 31A:
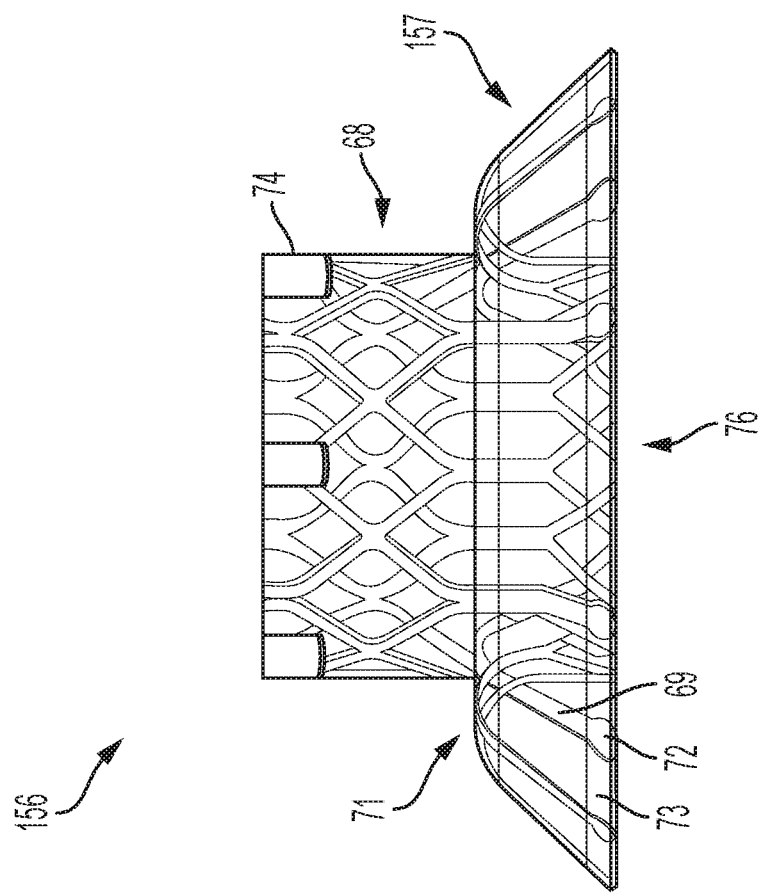

As shown in FIGS. 31A and 31B, an alternative embodiment of transcatheter heart valve 66 is transcatheter heart valve 156. In contrast to the transcatheter heart valve 66, which has an atrial sealing skirt top brim 67, transcatheter heart valve 156 has an atrial sealing skirt bottom brim 157, which is connected to the bottom of the transcatheter valve body 68, instead of the top, as in the transcatheter heart valve 66. The atrial sealing skirt bottom brim 157 conforms to the atrial floor 12, and the transcatheter valve body 68 of the transcatheter heart valve 157 extends into the left atrium 11, thereby minimizing interaction with the native mitral leaflets, further reducing the risk of LVOT obstruction.

At least one conduit 74 is defined in the transcatheter heart valve 66 or 156 as illustrated in FIGS. 10A and 10B, 11A and 11B, and 31A and 31B. Each conduit is sized and shaped so that a portion of the cord 37 (attached at the proximal end to suture 148) extends through the conduit 74, thereby connecting the tether 36 to the transcatheter heart valve 66 or 156, allowing free movement until the valve 66 or 156 is locked in place. In a further aspect, the transcatheter valve 66 or 156 has anchoring elements (not shown) positioned along its outer diameter. These anchoring elements allow fixation to the mitral annulus and/or leaflets but are not necessarily used a primary fixation mechanism.

The at least one cord 37 is coupled to the tether rod 38 of the tether 36, and the proximal portion of cord 37 is coupled to suture 148. In one aspect, the cord may be a strong yet flexible cord such as, for example and without limitation, an expanded polytetrafluoroethylene (ePTFE) or ultra-high-molecular-weight polyethylene (UHMWPE, UHMW) cord. In use, described more fully below, a central portion of the cord 37 (between the distal end and the proximal end) extends through and/or be coupled to the transcatheter valve 66 or 156 to hold the skirt in the desired position relative to the mitral annulus.

FIGS. 11A and 11B also illustrate the transcatheter valve 66. The transcatheter valve 66 has leaflets 77 extending radially inwardly from the transcatheter valve body 68. The leaflets 77 are composed of bovine, equine, or porcine pericardial leaflets. Like the functioning of any conventional valve, the leaflets 77, sewn to the interior of the transcatheter valve body 68, open during diastole (relaxation of the heart) allowing blood to enter from the left atrium 11 into the left ventricle 14, and closing during systole (contraction of the heart), preventing blood from regurgitating from either the right or left ventricle back into the right or left atrium, respectively.

As shown in FIGS. 10A and 10B, 11A and 11B, and 31A and 31B, the transcatheter heart valve 66 or 156, defined by transcatheter valve body 68 and atrial sealing skirt top brim 67 or atrial sealing skirt bottom brim 157, includes a membrane-like material and the atrial sealing skirt top brim 67 or bottom brim 157 has a diameter greater than the annulus at the site of deployment. For example, the atrial sealing skirt top brim 67 or bottom brim 157 may have a diameter greater than the diameter of the mitral annulus. In another aspect, the transcatheter heart valve is formed by, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The transcatheter heart valve 66 or 156 may also be covered with adult or juvenile bovine, ovine, equine, or porcine pericardium. Optionally, at least a portion of the atrial sealing skirt top brim 67 or bottom brim 157 may be formed from alternative materials, such as, for example and without limitation, polyurethane foam or other polymers.

In another aspect, at least a portion of the transcatheter heart valve 66 or 156 has one or more fixation members (not shown) along its length, allowing further anchoring to the left atrial floor and/or other portions on the atrial side of the mitral annulus, preventing migration of the transcatheter heart valve 66 or 156 into the proximal left atrium 11, thereby preventing instability (e.g. rocking) and paravalvular regurgitation of prosthesis.

The transcatheter heart valve 66 or 156 comprises at least a transcatheter valve body 68 and an atrial sealing skirt top brim 67 or bottom brim 157. As shown, the transcatheter valve body 68 is a cylinder and has a variable length and diameter. It is selectively composed of either laser-cut or molded nitinol, but also may contain elements of any other metallic alloy and may be covered along any portion of its circumference or length with either biological membranes or synthetic materials mentioned above. As shown, the top brim 67 or bottom brim 157 extends radially outwardly from the transcatheter valve body 68 and downwardly, forming a substantially concave top brim with the concavity facing the left atrial floor 11. The top brim 67 or bottom brim 157 extends circumferentially around the upper end of the transcatheter valve body 68, in the case of transcatheter heart valve 66, or extends circumferentially around the bottom end of the transcatheter valve body 68, in the case of the transcatheter heart valve 156.

At least one, or shown a plurality of, flexible extension members 69 are provided and which may, for example, be composed of, but not limited to, laser-cut or molded nitinol attached to the top of the skirt body by the extension member base 71 and terminating in the extension member tip 72. Between one or more extension members 69 is an elastic sealing membrane 73 extending perpendicular to adjacent extension members 69. As shown in FIGS. 10A and 10B, the extension member 69 may extend radially outwardly and substantially linearly, but this is exemplary. As shown in FIGS. 11A, 11B, 31A and 31B, the extension members may be nonlinear and generally U-shaped. As shown, the sealing membrane 73 extends circumferentially around the top brim 67 or bottom brim 157. It may extend only a portion of the circumference as well. The transcatheter valve body 68 includes a plurality of supports 78 which, like the extensions members 69 of the top brim 67 or bottom brim 157, may, for example, be composed of, but not limited to, laser-cut or molded nitinol. As shown, the supports 78 form a lattice-like configuration, but other configurations are contemplated including, but not limited to, vertically extending supports.

The sealing member 73 is composed of either biological tissues or synthetic fabrics as mentioned above. In one aspect, the synthetic fabric is either braided or knit, allowing the "stretchability" required to conform to atrial floor topography. In FIGS. 10A and 10B, 31A and 31B, the extension member 69 is attached to the transcatheter valve body 68 via the extension member base 71, and the extension member tip 72 is bending downwards, thereby preventing regurgitation around mitral annulus. This conformation requires downward force applied via one or more atrial positioning rods 147, attached to one or more conduits 74, and locked into place via one or more detachable locks 83 (FIG. 14A-B, 15A-B, 16A-B) integrated inside the atrial end of the conduits 74 as described herein.

FIGS. 30A-30D illustrate the placement of the valve as replacement for a native mitral valve. FIGS. 30A and B illustrate the valve having an atrial sealing skirt top brim 67 and FIGS. 30C and D illustrate the valve having an atrial sealing skirt bottom brim 157. The mitral valve with a bottom sealing skirt 157 is positioned above atrial floor 12 shown in these figures. Use of this valve with the aforementioned tethers prevents substantial vertical or floating movement of the valve.

The Tether and Transcatheter Valve Delivery Assemblies

According to the method described above, the retrograde anchor 22 or antegrade anchor 49 is introduced by the retrograde anchor delivery sheath 131 or the antegrade anchor delivery sheath 134 and secured to the interventricular septum 20. Anchor cap 27 or 58 and either delivery cable 33 (for retrograde anchor) or wire rail 64 (for antegrade anchor) remain within the heart and are ready to receive the tether 36 described above.

Referring now to FIGS. 27A and 27B, and as described above, the tether 36 is advanced over the wire rail 64 or delivery wire 33 of the delivery cable 32 (not illustrated) through the transcatheter heart valve delivery system shown in the form of delivery guide 141. The tether 36 locks onto anchor cap 27 or 58 by coupling the docking ring 43 to the anchor cap 27 or 58. Coupled to at least one tether rod 38 is at least one cord 37 that extends from the tether rod 38. The at least one cord 37 is connected proximally to at least one suture 148, which extends outside the body via the central lumen 151 of the delivery guide 141. Once the tether is locked to the anchor cap 27 or 58, the guide 141 is retracted as shown in FIG. 27B, leaving the implanted anchor 22 or 49, tether 36, cords 37 and suture extending from the implantation site. As shown in FIGS. 27A-B, 28A-B, the same guide 141 delivers both the tether 36 and transcatheter heart valve 66 or 156.

Referring now to FIGS. 27A-B and 28A-B, the transcatheter heart valve delivery system 139 for positioning and deploying the transcatheter heart valve 66 or 156 at the desired deployment sites 13 is illustrated. The transcatheter valve delivery system 139 comprises a transcatheter valve delivery guide 141, a nosecone 146, a transcatheter valve deployment knob 142 and at least one atrial positioning rod 147. The transcatheter valve delivery guide 141 has a distal end 144, an opposed proximal valve deployment knob 142 and an inner guide lumen 143 extending therebetween. The inner guide lumen 143 is sized and configured so that the transcatheter valve 66 or 156 and other system components are selectively and removably inserted therethrough. At least a portion of the transcatheter valve delivery guide 141 is flexible so that a tip 144 at the distal end of the transcatheter valve guide 141 are positioned past the deployment site 13 and into the left ventricle 14.

The transcatheter valve deployment knob 142 is coupled to the proximal end of the transcatheter valve delivery guide 141. The transcatheter valve deployment knob 142 defines a central channel 151 which is in fluid communication with the inner guide lumen 143. Accordingly, the atrial positioning rod 147, the guide wire 64 and/or the at least one suture 148 may extend through the central channel 151 and into the inner guide lumen 143. As shown, the transcatheter deployment knob 142 is rotatable and configured such that rotation of the knob 142 in a first direction causes distal tip 144 of the transcatheter valve delivery guide 141 around the transcatheter valve 66 or 156 to be retracted, allowing transcatheter valve 66 or 156 to expand. The nosecone 146 may be any conventional nosecone coupled to the transcatheter valve delivery guide 141 and configured to guide the transcatheter valve 66 or 156 to the deployment site 13.

The Locking System

With reference to FIGS. 27A-B, 28B-C, and 29A, the at least one atrial positioning rod 147 has a distal end 153, a proximal end 150 and an inner rod lumen 149 extending there between, the inner rod lumen being sized and configured so that a portion of a suture 148 and/or a cord 37 is inserted therethrough. At least a portion of the atrial positioning rod 147 is flexible so that the distal end 153 of the atrial positioning rod may be positioned at or adjacent to the deployment site 13.

Figure 13B:
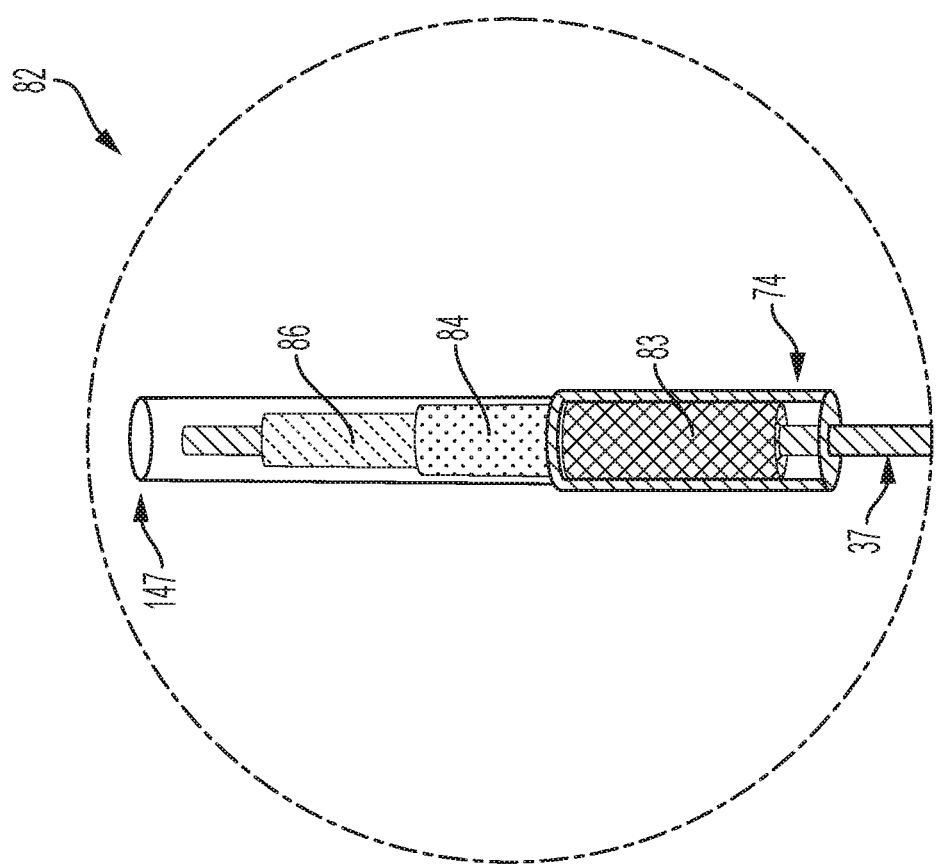
FIG. 13B is an enlarged side elevational view of the locking system.
Figure 13A:
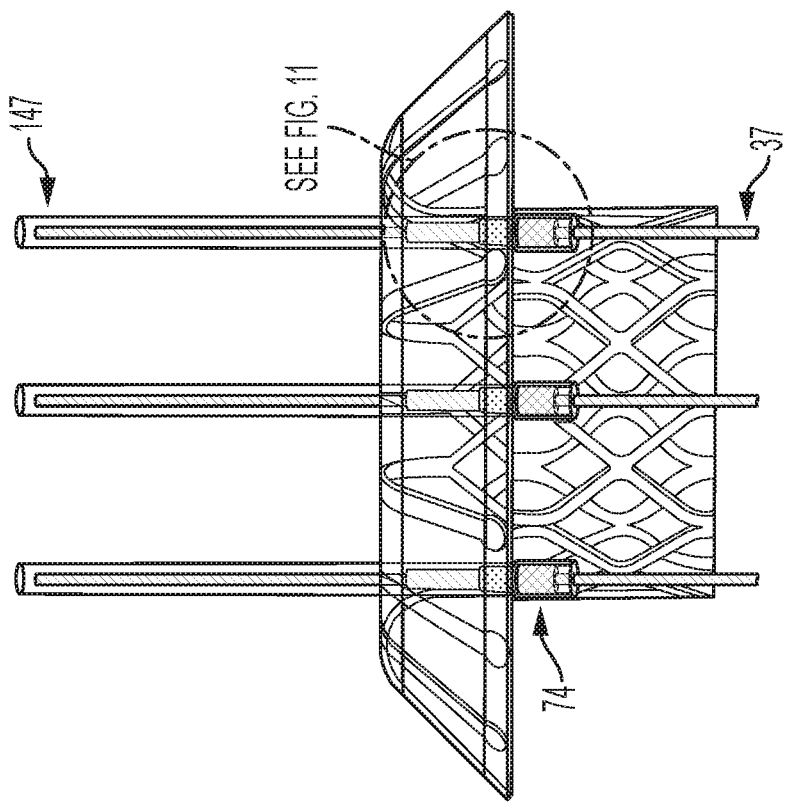
FIG. 13A is an enlarged side elevational view of the transcatheter valve body coupled to atrial positioning rods and cords.
Figure 14A:
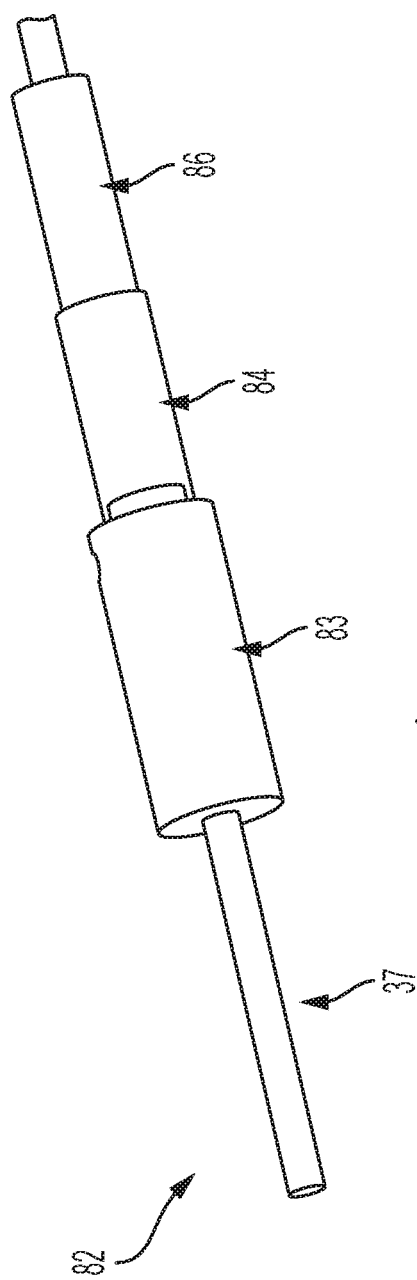
FIG. 14A is a perspective view of the locking system.
Figure 14B:
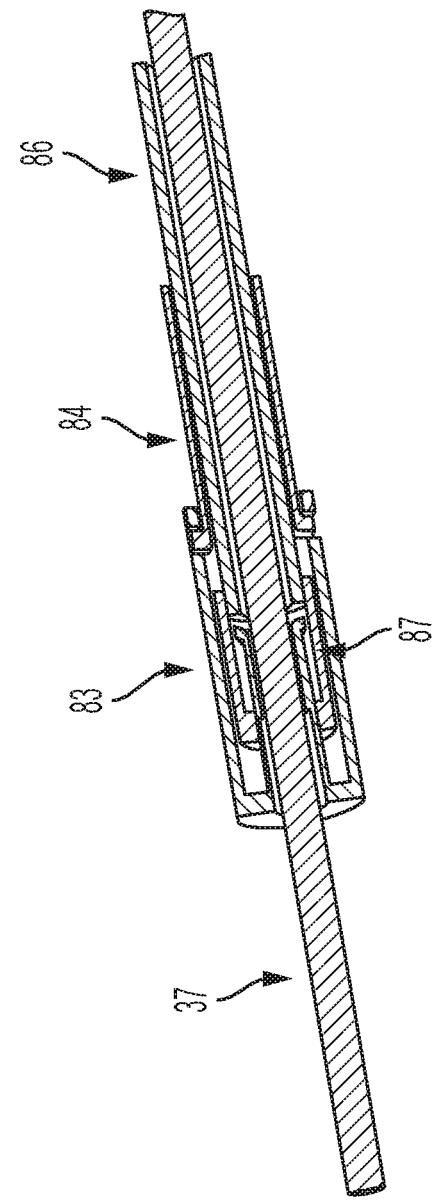
FIG. 14B is a perspective cut-away view of the locking system.

The at least one positioning rod 147 is coupled to the conduit 74. As illustrated FIGS. 13A and 13B, each conduit 74 contains a detachable lock 83, which is configured to securely attach at least one cord 37. Thus, the cord 37 is securely attached to the tether rod 38 of the tether 36, which is coupled to anchor cap 27 or 58, secured to interventricular septum 20 via the ventricular disks and septal connectors of either the retrograde anchor 22 or the antegrade anchor 49, and the detachable lock 83 securely attaches the cord 37 in the left atrium, for example.

Referring to FIGS. 13A, 13B, 14A, 14B, 15A, 15B, 16A and 16B, the locking system 82 consists of a detachable lock 83, integrated inside conduit 74, attached to first gateway hypotube 84 and second retracting hypotube 86. Inside the detachable lock 83 is a locking clip 87. With reference now to FIG. 30A, the system 10 further comprises a suture cutter 154 sized and configured to pass through the delivery sheath 117 to cut the at least one suture 148 (as shown in FIG. 30B).

The Method of Implanting, Positioning and Locking the Atrial Skirt

In use, the system 10 implants the transcatheter heart valve 66 or 156 utilizing a transcatheter approach by placing interventricular anchor 22 or 49 and docking a tether 36 to the anchor 22 or 49. As shown in FIG. 27A, the transcatheter valve system 139 is inserted over either wire 64 or the flexible wire 33 of the delivery cable 32 and into a portion of the heart 9. As the transcatheter valve delivery guide 141, with the transcatheter valve 66 or 156 preloaded into distal end 144, is inserted into the heart, at least a portion of the suture 148 is also preloaded and threaded through the at least one conduit 74, and as transcatheter valve delivery guide 141 advances, at least a portion of suture 148 and cord 37 extend along and proximally beyond the inner guide lumen 143 of the transcatheter valve delivery guide 141. Thus, a portion of the at least one cord 37 extends through and beyond the distal end 144 of the transcatheter valve delivery guide 141, and a portion of the at least one suture 148 extends through and beyond the transcatheter valve delivery guide 141. The transcatheter valve delivery guide 141 is positioned so that the distal end 144 of the transcatheter valve delivery guide 141, with the transcatheter valve 66 or 156 preloaded into distal end 144, is passed through the deployment site 13 and into the left ventricle 14.

The transcatheter valve 66 or 156 is preloaded into distal end 144 of the transcatheter valve delivery guide 141 for positioning at the deployment site 13. As shown, the suture 148 is pre-assembled with the transcatheter valve 66 or 156 such that each suture 148 is threaded through the at least one conduit 74 of the transcatheter valve 66 or 156, illustrated in FIGS. 11A-B, and FIGS. 31A-B. As the transcatheter valve 66 or 156 and distal end 144 of transcatheter valve delivery guide 141 advance as a unit and approach the deployment site, the end of the suture 148 and a portion of the cord 37 will become threaded through the conduit 74 defined in the transcatheter valve 66 or 156. As such, the transcatheter valve 66 or 156 is moveable along the length of the at least one cord until the desired deployment site 13 has been reached. That is, the transcatheter valve is free floating on the cord 37 until locked in placed by the detachable lock 83.

When the transcatheter valve 66 or 156 is in the desired deployment site 13, the transcatheter valve deployment knob 142 is utilized to at least partially withdraw the delivery guide 141 around the transcatheter valve 66 or 156. With the guide 141 free of the transcatheter valve 66 or 156, the valve 66 or 156 expands to its full, unrestrained size. Optionally, because the transcatheter valve's position is adjustable, the transcatheter valve deployment knob 142 can be used to collapse the transcatheter valve 66 or 156, allowing repositioning to the desired deployment site.

An atrial positioning rod 147, preloaded in the transcatheter delivery guide 141, is then advanced over each suture 148 such that a portion of each suture extends within inner rod lumen 149 and a portion of each suture extends beyond the proximal end 150 of the positioning rod 147. With reference to FIGS. 28B and 29A, the positioning rod 147 is then advanced through the transcatheter valve guide 141 and a portion of the cord 37 is received by the inner rod lumen 149 of the rod 147 and the distal end 153 of the positioning rod (with the detachable lock 83 attached thereto) is adjacent to the transcatheter valve 66 or 156. The positioning rods 147 are pushed down by the user until the sealing skirt is in a desired position relative to the mitral annulus.

The transcatheter valve 66 or 156 over the tether 36 until the desired valve 66 or 156 position is achieved. After the desired valve position is achieved, the at least one atrial positioning rod 147 urges the transcatheter valve 66 or 156 into position and is locked into place via a detachable lock 83 nestled within each conduit 74 and connected to the end of each positioning rod 147. The transcatheter valve 66 or 156 may be repositioned or retrieved until release of the sutures 148 that extend through each atrial positioning rod 147.

As shown in FIG. 28B, the positioning of the transcatheter valve 66 or 156 inside the left atrium 11 so that the transcatheter valve 66 top brim 67 or the transcatheter valve 156 bottom brim 157 conforms to the topography of the left atrial floor 12 is shown. Via the transcatheter valve delivery system end 144, the practitioner advances one or more atrial positioning rods 147 so that the transcatheter valve 66 or 156 translates over one or more cords 37, which extend through one or more conduits 74, defined by the transcatheter valve body 68. As shown in FIG. 28B, once the transcatheter top brim 67 or bottom brim 157 contacts the atrial floor 12, and the one or more extension members 69 flex differentially according to the local anatomy. Because each atrial positioning rod 147 is pushed with differential force, precise tension amounts are achievable, and therefore more or less flexion of the extensions members 69 to facilitate conformation of the transcatheter valve top brim 67 or bottom brim 157 around the entire perimeter of the atrial floor 12 to limit regurgitation through the mitral valve orifice.

Figure 12:
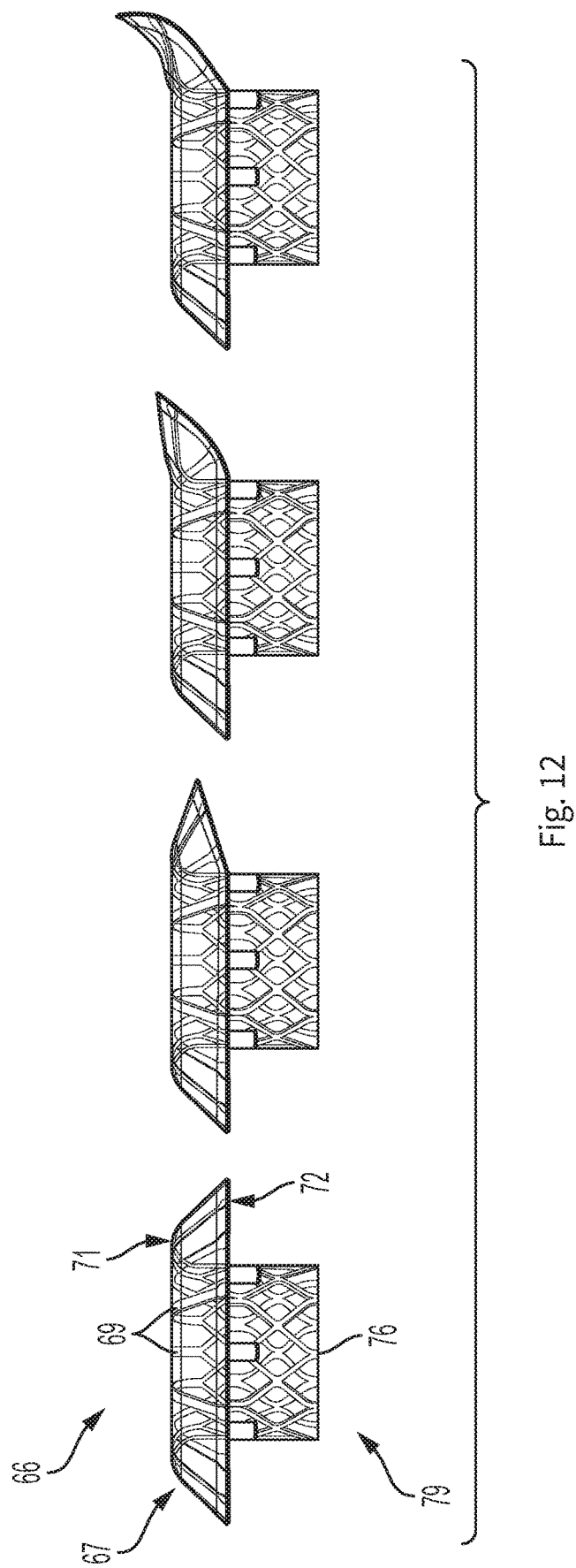
FIG. 12 is a side elevational view of the transcatheter valve with valve with one edge of the top brim transitioning from a concave to a convex configuration.

FIG. 12 illustrates the conversion of the transcatheter valve top brim 67 from concave to convex (the same conformational change can occur with the bottom brim 157). As the valve is pushed down to the atrial floor 12 by atrial positioning rod 147, which is attached to the extension member base 71 of the extension member 69, the extension member tip 72 flexes upward, conforming to the convex atrial floor anatomy. Further distal movement of the transcatheter valve 66 (shown left to right in FIG. 12) or transcatheter valve 156 (not shown) further modifies the shape of the top brim 67 or bottom brim 157 as it confirms to the atrial floor and as the extension member base 71 are urged downward by atrial positioning rod 147 (FIG. 28B).

Figure 15A:
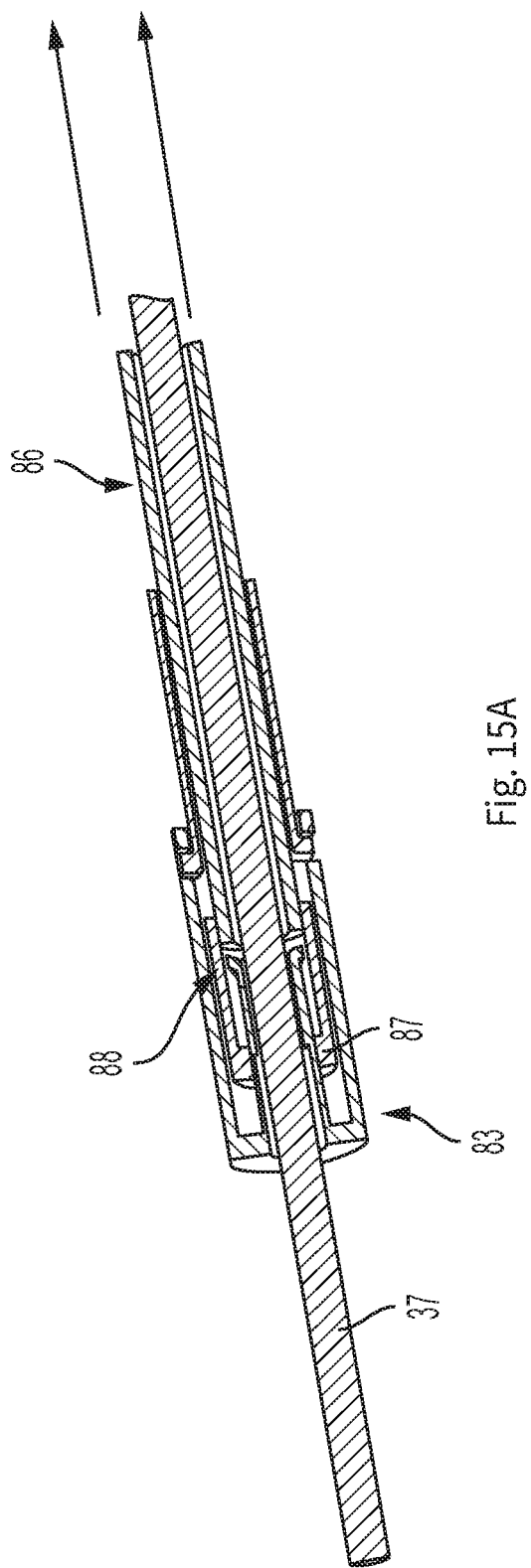
FIG. 15A is a cross-sectional side view of the locking system for transcatheter valve body positioning in an unlocked position.
Figure 15B:
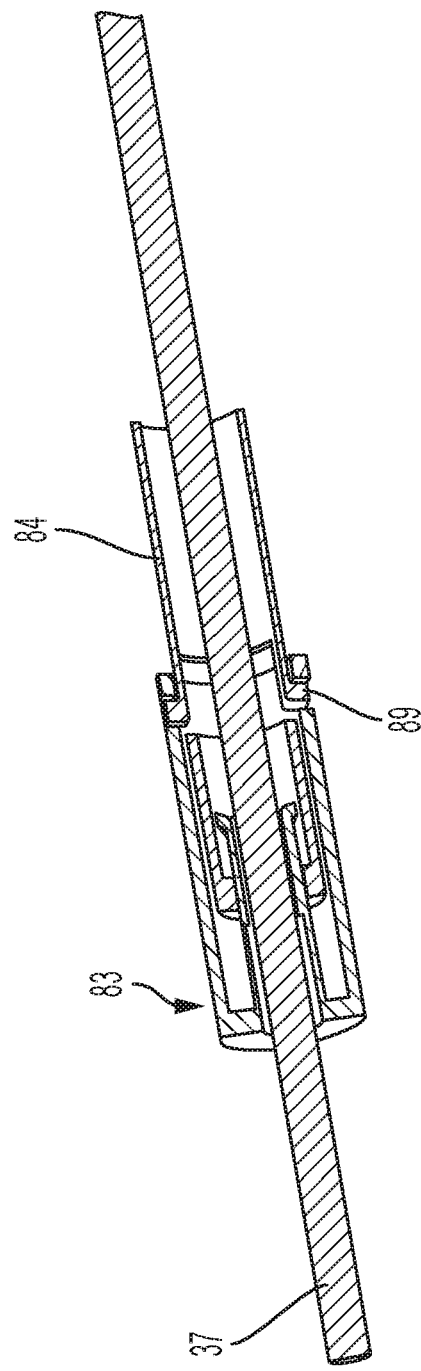
FIG. 15B is a cross-sectional side view of the locking system for transcatheter valve body positioning in a locked position.
Figure 16A:
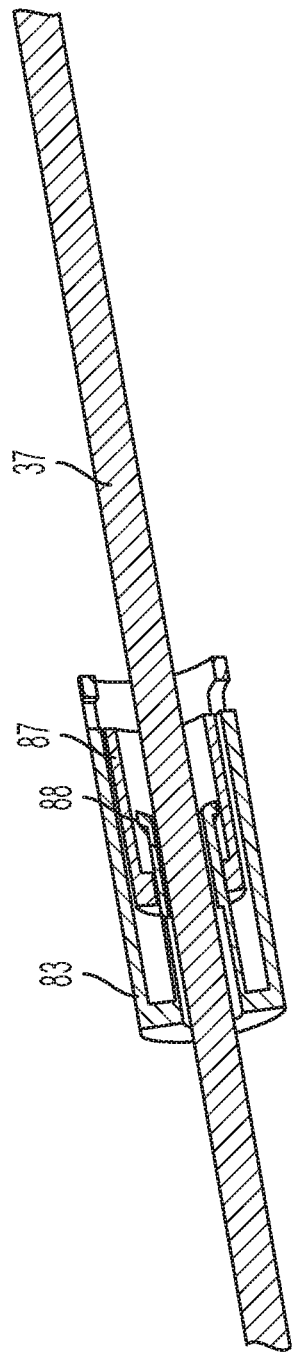
FIG. 16A is a partially cut away view of the locking system in the locked position.
Figure 16B:
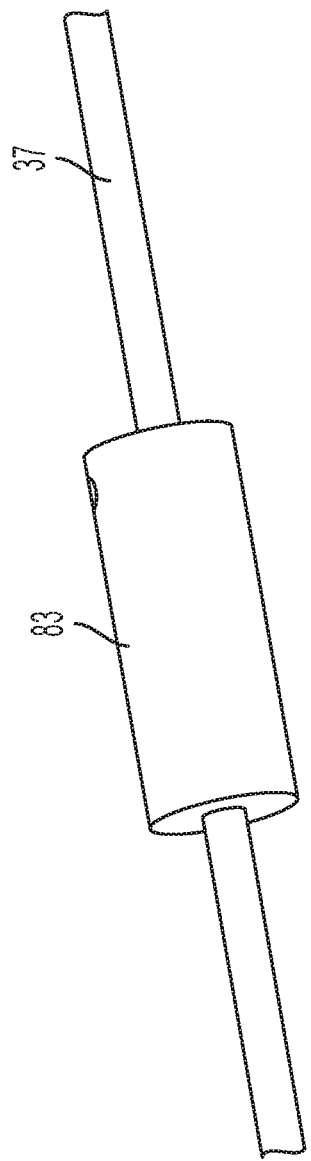
FIG. 16B is a perspective view of the locking system.

Now referring to FIGS. 15A and 15B, pulling of the retracting hypotube 86 causes retraction of locking clip 87, which pushes down on locking tabs 88, and engaging cord 37. More specifically, the second hypotube 86 is retracted and due to its connection to the locking clip 87, it also retracts the locking clip 87. The locking clip 87, upon retraction, contacts the contact points 89 of the first gateway hypotube 84, disconnecting the clip 87 permitting the second hypotube 86 to be removed. Once retracting hypotube 86 is pulled, the inner arms of gateway hypotube 84 spring inward, allowing gateway hypotube to be removed. The first gateway hypotube 84 is beneficial as it enables the cord 37 to be locked while the second hypotube 86 is being retracted. The gateway hypotube 84 is then removed, leaving the clip 87 within the conduit 74 of the transcatheter valve 66 or 156. FIG. 16A shows a cut-away view of a lock fully engaged. According to one aspect, the positioning rod 147 may be integrated with the gateway hypotube or removably connected thereto. FIG. 16B shows an intact view of a fully engaged lock.

As illustrated in FIG. 30A, with the transcatheter valve securely conforming to atrial floor 12, the suture cutter 154 is advanced over the sutures 148 and to the transcatheter valve top brim 67. The suture cutter 154 cuts and releases the distal end of each suture 148 above the detachable lock 83. The sutures 148 and the suture cutter 154 are then be removed from the heart 9.

In one aspect, prior to cutting of the sutures 148, the transcatheter valve 66 or 156 may be retrieved or repositioned. For example, if it is determined that the transcatheter valve is to be removed or repositioned, an atrial positioning rod 147 is positioned over each suture so that a portion of the suture is in the inner rod lumen 149. When the distal end 153 of the positioning rod is adjacent to or in contract with the detachable lock 83, advancing the gateway hypotube 84 and the retracting hypotube 86 attaches the detachable lock to the distal end of the positioning rod, thereby unlocking the lock from the cord 37. With each cord unlocked, the valve may be removed from and/or repositioned in the deployment site 13.

In another aspect, the transcatheter valve 66 or 156 repositioned and/or removed days to weeks after valve deployment. In this aspect, the sutures are not cut, but wrapped around a spool or other wrapping device. This device is then attached to the transcatheter valve top brim 67 of valve 66, or to the transcatheter valve body 68 of valve 156. Days after deployment of the valve and completion of the procedure, the spool/wrapping device may be re-captured, allowing un-wrapping and retrieval of the sutures. An atrial positioning rod 147 is then positioned over each suture so that a portion of the suture is in the inner rod lumen 149. When the distal end 153 of the positioning rod is adjacent to or in contract with the detachable lock 83, advancing the gateway hypotube 84 and the retracting hypotube 86 attaches the detachable lock to the distal end of the positioning rod, thereby unlocking the lock from the cord 37. With each cord unlocked, the valve is removed from and/or repositioned in the deployment site 13.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An anchor assembly for implanting an anchor to an interventricular septum of a heart for minimally invasively securing a mitral valve to replace the native mitral valve comprising:
   the anchor configured and sized for endovascular introduction for anchoring to an anchoring site on the interventricular septum comprising an anchor cap, a left ventricular disc, a right ventricular disc, and a septal connector, wherein the anchor cap extends proximally from the left ventricular disc and wherein the septal connector extends between said left ventricular disc and said right ventricular disc wherein said septal connector is sized and configured to extend through the interventricular septum wherein said left ventricular disc and said right ventricular disc are positioned on opposing sides of the interventricular septum;
   an anchor delivery system comprising a delivery cable having a distal end portion defined by a first surface configuration and wherein said anchor comprises a mating portion having a second configuration so as to mate with said delivery cable distal end portion first surface configuration; and a tether assembly comprising a docking ring and at least one tether rod connected to said docking ring wherein said docking ring defines a central aperture configured to be positioned on said anchor cap.

2. The anchor assembly according to claim 1 wherein said second configuration is defined by a proximal end of said anchor cap and defines a threaded cavity and said delivery cable distal end portion is threaded so as to matingly engage said anchor cap threaded cavity to position said anchor cap.

3. The anchor assembly according to claim 1 wherein said anchor further comprises a delivery cable connector extending distally from said right ventricular disc wherein said delivery cable connector defines a threaded cavity and said delivery cable first surface defines a threaded distal end so as to matingly engage said connector threaded cavity.

4. The anchor assembly according to claim 3 wherein said delivery cable defines a longitudinally extending lumen, said anchor cap defines a longitudinally extending lumen, said septal connector defines a longitudinally extending lumen and said delivery cable connector defines a longitudinally extending lumen and said anchor deliver systems further comprises a delivery wire which extends through said lumens of said anchor cap, said septal connector, said delivery cable connector and said delivery cable.

5. The anchor assembly according to claim 1 wherein said anchor cap comprises at least one locking member extending radially outwardly from said anchor cap.

6. The anchor assembly according to claim 5 wherein said at least one locking member moves between a first locked position wherein the at least one locking member extends a first distance from an outer surface of said anchor cap to a second position wherein said at least one locking member extends a second distance from said outer surface wherein said first distance is greater than said second distance.

7. The anchor assembly according to claim 6 wherein said tether docking ring urges said at least one locking member from said first locked position to said second position when it is positioned over said at least one locking member and said at least one locking member, in said first locked position, engages said docking ring when the docking ring is positioned distal of said at least one locking arm on said anchor cap.

8. The anchor assembly according to claim 1 wherein said left and right ventricular discs are formed of a material selected to enable sheathing and unsheathing of said discs.

9. The anchor assembly according to claim 1 wherein said anchor mating portion second configuration is defined by said anchor cap and said anchor assembly further comprises an anchor shaft and at least one locking member on said anchor shaft and wherein said delivery cable distal end portion is an anchor connector configured to removably mate with said anchor shaft.

10. The anchor assembly according to claim 9 wherein said at least one locking member is biased outwardly from said anchor shaft and wherein said anchor connector defines a distal cavity and a proximal portion of said anchor shaft is selectively housed within said cavity to connect said anchor and said anchor delivery system.

11. The anchor assembly according to claim 10 wherein an anchor base defines at least one anchor flange and said anchor connector defines at least one aperture configured for receipt of said anchor flange.

\* \* \* \* \*